US012324807B2

(12) United States Patent
Cantley et al.

(10) Patent No.: US 12,324,807 B2
(45) Date of Patent: Jun. 10, 2025

(54) COMBINATION THERAPY FOR PI3K-ASSOCIATED DISEASE OR DISORDER

(71) Applicants: Cornell University, Ithaca, NY (US); The Trustees of Columbia University, New York, NY (US)

(72) Inventors: Lewis C. Cantley, Cambridge, MA (US); Benjamin Hopkins, Larchmont, NY (US); Marcus Goncalves, Garden City, NY (US); Siddhartha Mukherjee, New York, NY (US)

(73) Assignees: Cornell University, Ithaca, NY (US); The Trustees of Columbia University, New York, NY (US)

( * ) Notice: Subject to any disclaimer, the term of this patent is extended or adjusted under 35 U.S.C. 154(b) by 0 days.

(21) Appl. No.: 15/733,852

(22) PCT Filed: May 31, 2019

(86) PCT No.: PCT/US2019/034949
§ 371 (c)(1),
(2) Date: Nov. 30, 2020

(87) PCT Pub. No.: WO2019/232403
PCT Pub. Date: Dec. 5, 2019

(65) Prior Publication Data
US 2021/0236501 A1 Aug. 5, 2021

Related U.S. Application Data

(60) Provisional application No. 62/679,329, filed on Jun. 1, 2018.

(51) Int. Cl.
| *A61K 31/5377* | (2006.01) |
| *A61K 31/155* | (2006.01) |
| *A61K 31/4375* | (2006.01) |
| *A61K 31/4439* | (2006.01) |
| *A61K 31/4745* | (2006.01) |
| *A61K 31/4985* | (2006.01) |
| *A61K 31/553* | (2006.01) |
| *A61P 35/00* | (2006.01) |

(52) U.S. Cl.
CPC ........ *A61K 31/5377* (2013.01); *A61K 31/155* (2013.01); *A61K 31/4375* (2013.01); *A61K 31/4439* (2013.01); *A61K 31/4745* (2013.01); *A61K 31/4985* (2013.01); *A61K 31/553* (2013.01); *A61P 35/00* (2018.01)

(58) Field of Classification Search
CPC .............. A61K 31/5377; A61K 31/155; A61K 31/4375; A61K 31/4439; A61K 31/4745; A61K 31/4985; A61K 31/553; A61P 35/00
See application file for complete search history.

(56) References Cited

U.S. PATENT DOCUMENTS

| 2,313,993 | A | 3/1943 | Bela |
| 4,450,164 | A | 5/1984 | Bristol et al. |
| 5,262,564 | A | 11/1993 | Kun et al. |
| 5,593,997 | A | 1/1997 | Dow et al. |
| 5,770,599 | A | 6/1998 | Gibson |
| 6,057,320 | A | 5/2000 | Spada et al. |
| 6,140,332 | A | 10/2000 | Traxler et al. |
| 6,251,911 | B1 | 6/2001 | Bold et al. |
| 6,268,391 | B1 | 7/2001 | Dickerson et al. |
| 6,350,735 | B1 | 2/2002 | Monaghan |
| 6,390,821 | B1 | 5/2002 | Shokat |
| 6,407,076 | B1 | 6/2002 | Box et al. |
| 6,448,236 | B1 | 9/2002 | Monaghan |
| 6,455,510 | B1 | 9/2002 | Charles et al. |
| 6,472,153 | B1 | 10/2002 | Dempcy et al. |
| 6,525,032 | B2 | 2/2003 | Mantell et al. |
| 6,544,960 | B1 | 4/2003 | Eldred et al. |
| 6,624,119 | B1 | 9/2003 | Reinhard et al. |
| 6,632,809 | B2 | 10/2003 | Grillot et al. |
| 6,660,744 | B1 | 12/2003 | Hirst et al. |
| 6,900,309 | B1 | 5/2005 | Mantell et al. |
| 6,916,828 | B2 | 7/2005 | Farrerons Gallemi et al. |
| 7,026,461 | B1 | 4/2006 | Shokat |
| 7,148,228 | B2 | 12/2006 | Kasibhatla et al. |
| 7,217,722 | B2 | 5/2007 | Takami et al. |
| 7,271,262 | B2 | 9/2007 | La Greca et al. |

(Continued)

FOREIGN PATENT DOCUMENTS

| CN | 105147696 A | 12/2015 |
| CN | 113194752 A | 7/2021 |

(Continued)

OTHER PUBLICATIONS

English Translation of CN 105147696 (Li, Rongqin). Published on Dec. 16, 2015. Retrieved from Dialog on Jan. 24, 2022. (Year: 2015).*

Ciaraldi, et al. Length of Acute Exposure to Insulin Regulates the Rate of Deactivation of STimulated Glucose Transport in Insolated Rate Adipocytes. Endocrinoly, vol. 113, Issue 5, 1983. (Year: 1983).*

Oleksyszyn, Jozef. The complete control of glucose level utilizing the composition of ketogenic diet with the anti-diabetic drug metformin, as a potential anti-cancer therapy. Med Hypotheses. Aug. 2011; 77(2). (Year: 2011).*

(Continued)

*Primary Examiner* — James H Alstrum-Acevedo
*Assistant Examiner* — Lauren Wells
(74) *Attorney, Agent, or Firm* — Schwegman Lundberg & Woessner, P.A.

(57) ABSTRACT

Described herein are compositions and methods for treating a disease or disorder associated with PI3K signaling. For example, such compositions can include use of modulators of glucose metabolism, use of at least one kinase in the insulin-receptor/PI3K/AKT/mTOR pathway, and/or use of diet that influences the subject's metabolic state.

40 Claims, 60 Drawing Sheets
Specification includes a Sequence Listing.

(56) References Cited

U.S. PATENT DOCUMENTS

| | | | |
|---|---|---|---|
| 7,332,497 B2 | 2/2008 | Hirst et al. | |
| RE40,245 E | 4/2008 | Grillot et al. | |
| 7,435,739 B2 | 10/2008 | Chen et al. | |
| 7,452,880 B2 | 11/2008 | Arora et al. | |
| 7,534,797 B2 | 5/2009 | Arnold et al. | |
| 7,585,868 B2 | 9/2009 | Knight et al. | |
| 7,608,603 B2 | 10/2009 | Dewdney et al. | |
| 7,615,552 B2 | 11/2009 | Ono et al. | |
| 7,651,687 B2 | 1/2010 | Buck et al. | |
| 7,678,803 B2 | 3/2010 | Huang et al. | |
| 7,723,330 B2 | 5/2010 | Blake et al. | |
| 7,745,428 B2 | 6/2010 | Andrews et al. | |
| 7,872,014 B2 | 1/2011 | Anand et al. | |
| 7,932,260 B2 | 4/2011 | Fowler et al. | |
| 7,994,181 B2 | 8/2011 | Giordani et al. | |
| 8,404,694 B2 | 3/2013 | White et al. | |
| 8,637,542 B2 | 1/2014 | Liu et al. | |
| 8,653,127 B2 | 2/2014 | Luo | |
| 8,697,709 B2 | 4/2014 | Dar et al. | |
| 8,703,778 B2 | 4/2014 | Ren et al. | |
| 8,865,699 B2 | 10/2014 | Ramsden et al. | |
| 8,883,820 B2 | 11/2014 | Wilson et al. | |
| 8,987,280 B2 | 3/2015 | Dotson et al. | |
| 8,993,580 B2 | 3/2015 | Ren et al. | |
| 9,085,560 B2 | 7/2015 | Ren et al. | |
| 9,096,590 B2 | 8/2015 | Ren et al. | |
| 9,096,611 B2 | 8/2015 | Ren et al. | |
| 9,127,000 B2 | 9/2015 | Ren et al. | |
| 9,295,673 B2 | 3/2016 | Ren et al. | |
| 9,682,141 B2 | 6/2017 | Jessen et al. | |
| 10,973,251 B1 | 4/2021 | Li et al. | |
| 11,000,513 B2 | 5/2021 | Kaupinen et al. | |
| 11,241,407 B2 | 2/2022 | Li et al. | |
| 11,547,697 B2 | 1/2023 | Ren et al. | |
| 2001/0024833 A1 | 9/2001 | Laborde et al. | |
| 2002/0013460 A1 | 1/2002 | Ueno et al. | |
| 2002/0156081 A1 | 10/2002 | Hirst et al. | |
| 2003/0073218 A1 | 4/2003 | Shokat | |
| 2003/0114467 A1 | 6/2003 | Shakespeare et al. | |
| 2003/0180924 A1 | 9/2003 | DeSimone | |
| 2003/0187001 A1 | 10/2003 | Calderwood et al. | |
| 2004/0023972 A1 | 2/2004 | Sundermann et al. | |
| 2005/0085472 A1 | 4/2005 | Tanaka et al. | |
| 2005/0197340 A1 | 9/2005 | Arora et al. | |
| 2006/0025383 A1 | 2/2006 | Wishart et al. | |
| 2006/0036061 A1 | 2/2006 | Shin et al. | |
| 2006/0106013 A1 | 5/2006 | Breitfelder et al. | |
| 2006/0246551 A1 | 11/2006 | Stack et al. | |
| 2007/0049591 A1 | 3/2007 | Pinkerton et al. | |
| 2007/0054915 A1 | 3/2007 | Arora et al. | |
| 2007/0072897 A1 | 3/2007 | Mahaney et al. | |
| 2007/0099871 A1 | 5/2007 | Davis et al. | |
| 2007/0112005 A1 | 5/2007 | Chen et al. | |
| 2007/0149521 A1 | 6/2007 | Crew et al. | |
| 2007/0213355 A1 | 9/2007 | Capraro et al. | |
| 2007/0224672 A1 | 9/2007 | Leban et al. | |
| 2007/0249598 A1 | 10/2007 | Wang et al. | |
| 2008/0003254 A1 | 1/2008 | Mack et al. | |
| 2008/0014200 A1 | 1/2008 | Arnold et al. | |
| 2008/0039459 A1 | 2/2008 | Folkes et al. | |
| 2008/0076758 A1 | 3/2008 | Folkes et al. | |
| 2008/0096868 A1 | 4/2008 | Schmiedeberg et al. | |
| 2008/0234262 A1 | 9/2008 | Zask et al. | |
| 2008/0293674 A1 | 11/2008 | Schwarz et al. | |
| 2009/0054405 A1 | 2/2009 | Booker et al. | |
| 2009/0124638 A1 | 5/2009 | Shokat et al. | |
| 2009/0192176 A1 | 7/2009 | Zask et al. | |
| 2009/0274698 A1 | 11/2009 | Bhagwat et al. | |
| 2009/0286779 A1 | 11/2009 | Imbach et al. | |
| 2009/0325967 A1 | 12/2009 | Fairhurst et al. | |
| 2010/0029693 A1 | 2/2010 | Douangpanya et al. | |
| 2010/0056494 A1 | 3/2010 | Winzeler et al. | |
| 2010/0075965 A1 | 3/2010 | Ni et al. | |
| 2010/0184760 A1 | 7/2010 | Ren et al. | |
| 2010/0215751 A1 | 8/2010 | Desai et al. | |
| 2011/0021541 A1 | 1/2011 | White et al. | |
| 2011/0178070 A1 | 7/2011 | Gong et al. | |
| 2011/0224223 A1 | 9/2011 | Shokat et al. | |
| 2012/0059005 A1* | 3/2012 | Baselga | A61K 31/5377 514/235.8 |
| 2012/0294930 A1 | 11/2012 | Ren et al. | |
| 2013/0261102 A1 | 10/2013 | Ren et al. | |
| 2014/0072654 A1 | 3/2014 | D'Agostino et al. | |
| 2015/0290300 A1 | 10/2015 | Kaur et al. | |
| 2015/0291576 A1 | 10/2015 | Lemieux et al. | |
| 2015/0320727 A1 | 11/2015 | Ren et al. | |
| 2016/0089371 A1 | 3/2016 | Liu et al. | |
| 2016/0266129 A1 | 9/2016 | Janetopoulos | |
| 2016/0287601 A1 | 10/2016 | Zohren et al. | |
| 2016/0303056 A1 | 10/2016 | Longo et al. | |
| 2017/0100354 A1 | 4/2017 | Bjornsson et al. | |
| 2017/0273964 A1 | 9/2017 | Heuer | |
| 2018/0042902 A1 | 2/2018 | Ren et al. | |
| 2018/0050997 A1 | 2/2018 | Bair et al. | |
| 2018/0280370 A1 | 10/2018 | Schnell et al. | |
| 2019/0049436 A1 | 2/2019 | Ramaswamy | |
| 2019/0231761 A1 | 8/2019 | Shen | |
| 2020/0339589 A1* | 10/2020 | Blake | C07D 487/04 |
| 2021/0252013 A1 | 8/2021 | Greene et al. | |
| 2021/0322426 A1* | 10/2021 | Greene | A61K 31/437 |
| 2022/0313694 A1 | 10/2022 | Longo et al. | |
| 2022/0400730 A1 | 12/2022 | Li et al. | |
| 2022/0400732 A1 | 12/2022 | Goncalves et al. | |
| 2023/0321050 A1 | 10/2023 | Ren et al. | |
| 2023/0364063 A1 | 11/2023 | Tanaka et al. | |
| 2024/0165122 A1 | 5/2024 | Cantley et al. | |

FOREIGN PATENT DOCUMENTS

| | | |
|---|---|---|
| EP | 0773023 A1 | 5/1997 |
| EP | 1241176 A1 | 9/2002 |
| EP | 1488792 A2 | 12/2004 |
| EP | 0871448 B1 | 3/2005 |
| EP | 1052264 B1 | 3/2005 |
| EP | 1341769 B1 | 10/2007 |
| EP | 1880723 A1 | 1/2008 |
| EP | 1557410 B1 | 9/2009 |
| GB | 1323210 A | 7/1973 |
| JP | 2000072773 A | 3/2000 |
| JP | 2002037787 A | 2/2002 |
| JP | 2012526772 A | 11/2012 |
| JP | 2021525802 A | 9/2021 |
| JP | 2022504388 | 1/2022 |
| WO | WO-9631510 A1 | 10/1996 |
| WO | WO-9640706 A1 | 12/1996 |
| WO | WO-9715658 A1 | 5/1997 |
| WO | WO-0123399 A1 | 4/2001 |
| WO | WO-0194368 A1 | 12/2001 |
| WO | WO-0200676 A1 | 1/2002 |
| WO | WO-0222630 A1 | 3/2002 |
| WO | WO-02060879 A2 | 8/2002 |
| WO | WO-2004031177 A1 | 4/2004 |
| WO | WO-2005009389 A2 | 2/2005 |
| WO | WO-2005097800 A1 | 10/2005 |
| WO | WO-2006089106 A2 | 8/2006 |
| WO | WO-2006100119 A1 | 9/2006 |
| WO | WO-2006114180 A1 | 11/2006 |
| WO | WO-2007095588 A1 | 8/2007 |
| WO | WO-2008025821 A1 | 3/2008 |
| WO | WO-2008068470 A1 | 6/2008 |
| WO | WO-2008078091 A1 | 7/2008 |
| WO | WO-2008083070 A1 | 7/2008 |
| WO | 2008115974 | 9/2008 |
| WO | WO-2008118486 A1 | 10/2008 |
| WO | WO-2008144463 A1 | 11/2008 |
| WO | WO-2008144464 A1 | 11/2008 |
| WO | WO-2008152394 A1 | 12/2008 |
| WO | WO-2009008992 A2 | 1/2009 |
| WO | WO-2009017822 A2 | 2/2009 |
| WO | WO-2009021990 A1 | 2/2009 |
| WO | WO-2009023179 A2 | 2/2009 |
| WO | WO-2009055418 A1 | 4/2009 |
| WO | WO-2009060197 A1 | 5/2009 |
| WO | WO-2009068482 A1 | 6/2009 |

(56) References Cited

FOREIGN PATENT DOCUMENTS

| WO | WO-2009085945 A1 | 7/2009 |
|---|---|---|
| WO | WO-2009088986 A1 | 7/2009 |
| WO | WO-2009088990 A1 | 7/2009 |
| WO | 2009097490 | 8/2009 |
| WO | WO-2010036380 A1 | 4/2010 |
| WO | WO-2010039186 A2 | 4/2010 |
| WO | WO-2010051042 A1 | 5/2010 |
| WO | WO-2010051043 A1 | 5/2010 |
| WO | WO-2010068257 A1 | 6/2010 |
| WO | WO-2010130779 A2 | 11/2010 |
| WO | WO-2011022439 A1 | 2/2011 |
| WO | WO-2015051252 A1 | 4/2015 |
| WO | WO-2017144877 A1 | 8/2017 |
| WO | WO-2017161205 A1 | 9/2017 |
| WO | 2017180565 A1 | 10/2017 |
| WO | WO-2018027084 A2 | 2/2018 |
| WO | WO-2018052758 A1 | 3/2018 |
| WO | WO-2018170485 A1 | 9/2018 |
| WO | WO-2018170517 A1 | 9/2018 |
| WO | WO-2019232403 A1 | 12/2019 |
| WO | WO-2020073033 A1 | 4/2020 |
| WO | WO-2020076432 A1 | 4/2020 |
| WO | WO-2020191356 A1 | 9/2020 |
| WO | 2022015951 | 1/2022 |
| WO | WO-2015134837 A2 | 1/2022 |
| WO | WO-2022004859 A1 | 1/2022 |
| WO | WO-2023070023 A1 | 4/2023 |
| WO | WO-2023158783 A2 | 8/2023 |

OTHER PUBLICATIONS

Costa et al. Targeting the PI3K/AKT/mTOR pathway in triple-negative breast cancer: a review. Breast Cancer Research and Treatment 169, 397-406. Feb. 7, 2018. (Year: 2018).*

Carnero et al. The PTEN/PI3K/AKT pathway in vivo, cancer mouse models. Frontiers in Oncology. Published 2014. (Year: 2014).*

Heyduk et al. Homogeneous Insulin and C-Peptide Sensors for Rapid Assessment of Insulin and C-Peptide Secretion by Islets. Diabetes. Published 2010. (Year: 2010).*

Stephen L. Aronoff, Kathy Berkowitz, Barb Shreiner, Laura Want; Glucose Metabolism and Regulation: Beyond Insulin and Glucagon. Diabetes Spectr Jul. 1, 2004; 17 (3): 183-190. (Year: 2001).*

CDC. Diabetes. Retrieved from the internet on Oct. 5, 2023, https://www.cdc.gov/diabetes/basics/insulin-resistance.html#:~:text=Insulin%20also%20signals%20the%20liver,t%20eaten%20for%20a%20while. (Year: 2023).*

"International Application Serial No. PCT/US2019/034949, International Search Report mailed Oct. 10, 2019", 4 pgs.

"International Application Serial No. PCT/US2019/034949, Written Opinion mailed Oct. 10, 2019", 7 pgs.

Allen, BG, et al., "Ketogenic diets as an adjuvant cancer therapy: History and potential mechanism. Redox Biology", vol. 2, (Aug. 7, 2014), 963-970.

Bowman, C, et al., "Ketoacidosis with Canagliflozin Prescribed for Phosphoinositide 3-Kinase Inhibitor-Induced Hyperglycemia: A Case Report", Journal of Investigative Medicine High Impact Case Reports, vol. 5, No. 3, (Aug. 23, 2017), 1-4.

Hopkins, BD, et al., "Obesity and Cancer Mechanisms: Cancer Metabolism. Journal of Clinical Oncology", vol. 34, No. 35, (Nov. 7, 2016), 4277-4283.

Oleksyszyn, J, "The complete control of glucose level utilizing the composition of ketogenic diet with the gluconeogenesis inhibitor, the anti-diabetic drug metformin, as a potential anti-cancer therapy", Medical Hypotheses, vol. 77, No. 2, (May 6, 2011), 171-173, Abstract Only.

"Chinese Application No. 201980051319.8, Voluntary Amendment filed Nov. 18, 2021", (w/ English Translation of Claims), 10 pgs, Claims Only in English.

"European Application Serial No. 19810231.1, Extended European Search Report mailed Feb. 14, 2022", 17 pgs.

Crouthamel, Ming-Chih, et al., "Mechanism and Management of AKT Inhibitor-Induced Hyperglycemia", Clinical Cancer Research, 15(1), (Dec. 31, 2008), 217-225.

Hopkins, Benjamin D, et al., "Suppression of insulin feedback enhances the efficacy of PI3K inhibitors", Nature, 560(7719), (Jul. 4, 2018), 499-503.

Janku, Filip, et al., "Phosphoinositide 3-kinase (PI3K) pathway inhibitors in solid tumors : From laboratory to patients", Cancer Treatment Reviews, 59, (2017), 93-101.

Lei, Yong, et al., "Metformin targets multiple signaling pathways in cancer", Chinese Journal of Cancer, 36(1): 17, (Dec. 1, 2017), 9 pgs.

Yap, Timothy A., et al., "Targeting the PI3K-AKT-mTOR pathway: progress, pitfalls, and promises", Current Opinion in Pharmacology, 8(4), (2008), 393-412.

"European Application Serial No. 19810231.1, Response filed Jul. 15, 2021 to Office Action mailed Jan. 19, 2021", 2 pgs.

"European Application Serial No. 19810231.1, Response filed Jul. 30, 2021 to Office Action mailed Jan. 19, 2021", 8 pgs.

"International Application Serial No. PCT/US2019/034949, International Preliminary Report on Patentability mailed Dec. 10, 2020", 9 pgs.

Fassnacht, Martin, et al., "Linsitinib (OSI-906) versus placebo for patients with locally advanced or metastatic adrenocortical carcinoma: a double-blind, randomised, phase 3 study", *The Lancet Oncology* 16(4), (Mar. 2015), 1-10.

Gallo, Linda A., et al., "Probing SGLT2 as a therapeutic target for diabetes: Basic physiology and consequences", *Diabetes & Vascular Disease Research*, 12(2), (2015), 78-89.

Harada, Norio, "Role of sodium-glucose transporters in glucose uptake of the intestine and kidney", *Journal of Diabetes Investigation*, 3(4), (Aug. 2012), 352-353.

Kandoth, Cyriac, et al., "Mutational landscape and significance across 12 major cancer types", *Nature*, vol. 502, (2013), 333-339.

Massacesi, Cristian, et al., "PI3K inhibitors as new cancer therapeutics: implications for clinical trial design", *Onco Targets and Therapy*, 9, (2016), 203-210.

Mayer, Ingrid A., et al., "A Phase Ib Study of Alpelisib (BYL719), a PI3Kα-Specific Inhibitor, with Letrozole in ER$^+$/HER2$^−$ Metastatic Breast Cancer", *Clin Cancer Res*, 23(1) (2017), 26-34.

Millis, Sheri Z., et al., "Landscape of Phosphatidylinositol-3-Kinase Pathway Alterations Across 19784 Diverse Solid Tumors", *JAMA Oncology*, 2(12), (2016), 1565-1573.

Wright, Ernest M., et al., "Biology of Human Sodium Glucose", *Physiol Rev*, 91, (2011), 733-794.

"European Application Serial No. 19810231.1, Response Filed Sep. 12, 2022 to Extended European Search Report mailed Feb. 14, 2022", 12 pgs.

"Chinese Application Serial No. 201980051319.8, Office Action mailed Apr. 17, 2023", (w/ English Translation), 17 pgs.

3rd party observation dated Oct. 5, 2012 against Patent Application No. P2012-0042 in Domican Republic. 15 pages.

3rd party observation dated Oct. 5, 2012 against Patent Application No. P2012-0I 10 in Costa Rica. 6 pages.

Abdel-Mohsen, "Synthesis, Reactions and Antimicrobial Activity of 2-Amino-4-(8-quinolinol-5-yl)-1-(p-toly-l)-pyrrole-3-carbonitrile," Bull. Korean Chem. Soc. 26(5):719-728 (2005).

Aissat, Nasredine et al., "Anti proliferative effects of rapamycin as a single agent 132 and in combination with carboplatin and paclitaxel in head and neck cancer cell lines", Cancer Chemother. Pharmacol., 2008, vol. 62, p. 305-313.

Belardi et al., "Insulin and IGFs in obesity-related breast cancer" J Mammary Gland Biol Neoplasia 18, 277-289, doi:10.1007 /s10911-013-9303-7 (2013).

Bendell, J. C. et al., "Phase I, dose-escalation study of BKM120, an oral pan-Class I PI3K inhibitor, in patients with advanced solid tumors" J Clin Oncol. 30, 282-290, doi:10.1200/JCO.2011.36.1360 (2012).

Berndt et al., "The pl 110 crystal structure uncovers mechanisms for selectivity and potency of novel PI3K inhibitors," Nat. Chem. Biol. 6(2):117-124 (2010).

Bhat et al., "Pyrazolopyrimidine nucleosides. 12. Synthesis and biological activity of certain pyrazolo[3,4-d]pyrimidine nucleosides related to adenosine," J. Med. Chem. 24(10): 1165-1172 (1981).

(56) References Cited

OTHER PUBLICATIONS

Billingsley, et al. "Highly efficient moNphosphine-based catalyst for the palladiumcatalyzed suzuki-miyaura reaction ofheteroaryt halides and heteroaryt boronic acids and esters." J Am Chem Soc. 2007, 129(11), p. 3358-66.
Bishop, Anthony C. et al., "Design of allele-specific inhibitors to probe protein kinase signaling". Current Biology 8, p. 257-266, 1996.
Blethrow, Justin et al., "Design and Use of Analog-Sensitive Protein Kinases", Current Protocols in Molecular Biology 18.11.1-18.11.19, 2004.
Cameron, et al. "Metal-metal interactions in a Novel hybrid metallopolymer", Journal of the American Chemical Society, 1999; 121(50), p. 11773-11779.
Demin et al., "Analysis of the efficacy of SGLT2 inhibitors using semi-mechanistic model" Front Pharmacol. 5,218, doi:10.3389/fphar.2014.00218 (2014).
Di Marzo et al. "Palmitoylethanolamide Inhibits the Expression of Fatty Acid Amide Hydrolase and Enhances the Anti-proliferative Effect of Anandamide in Human Breast Cancer Cells," The Biochemical Journal, 2001, vol. 358, pp. 249-255.
Ding et al., "A combinatorial scaffold approach toward kinase-directed heterocycle libraries," J. Am. Chem. Soc. 124 (8): 1594-1596 (2002).
Douris et al., "Adaptive changes in amino acid metabolism permit normal longevity in mice consuming a low-carbohydrate ketogenic diet" Biochim Biophys Acta 1852, 2056-2065, doi:10.1016/j.bbadis.2015.07.009 (2015).
Edgar, et al., "Isoform-specific phosphoiNsitide 3-kinase inhibitors exert distinct effects in solid tumors" Cancer Res. Feb. 1, 2010;70(3):1164-72.
Extended European Search Report mailed on Dec. 20, 2012, for EP Application No. 10810518.0, 8 pages.
Fajans et al., "Maturity onset diabetes of the young (MODY)," Diabet. Med. 13(9 Suppl 6): S90-S95 (1996).
Farag, et al. Synthesis and reactivity of 2-(benzothiazol-2-y 1 )-1-bromo-1,2-ethanedlone-1-arvlhvdrazones. Heteroatom Chemistry. 1997; 8(1):45-50.
Fellmann et al., "An Optimized microRNA Backbone for Effective Single-Copy RNAi," Cell Reports, vol. 5, Issue 6, pp. 1704-1713 (Dec. 2013).
Final Office Action for U.S. Appl. No. 16/211,803 mailed on Apr. 6, 2022, 16 pages.
Final Office Action for U.S. Appl. No. 16/211,803 mailed on Oct. 9, 2020, 12 pages.
Fruman et al., "The PI3K Pathway in Human Disease" Cell 170, 605-635, doi:10.1016/j.cell.2017.07.029 (2017).
Gaestel et al., "Protein kinases as small molecule inhibitor targets in inflammation," Curr. Med. Chem. 14(21):2214-2234 (2007).
Gallagher et al., "IGF, Insulin, and Cancer" Endocrinology 152, 2546-2551, doi:10.1210/en.2011-0231 (2011).
Gallagher et al., "Inhibiting PI3K reduces mammary tumor growth and induces hyperglycemia in a mouse model of insulin resistance and hyperinsulinemia" Oncogene 31, 3213-3222, doi:10.1038/onc.2011.495 (2012).
Garin, et al. "Diheterocyclic compounds from dithiocarbamates and derivatives thereof. II. 2,2'-diamino-6,6'-bibenzoazoles" Journal of Heterocyclic Chemistry, 1990, 27, p. 321-326.
International Search Report and Written Opinion dated Aug. 20, 2012 for PCT Application No. US2012/026406. 13 pages.
International Search Report and Written Opinion dated Aug. 22, 2011 for PCT Application No. PCT/US11/37742, 10 pages.
International Search Report and Written Opinion mailed on Feb. 2, 2023, for PCT Application No. PCT/US2022/078418, filed on Oct. 20, 2022, 11 pages.
International Search Report and Written Opinion mailed on Nov. 16, 2010, for PCT Application No. PCT/US2010/045816, filed on Aug. 17, 2021, 11 pages.

Juric et al., "A First-in-Human, Phase I, Dose-Escalation Study of TAK-117, a Selective PI3Kα Isoform Inhibitor, in Patients with Advanced Solid Malignancies" Clin Cancer Res. (2017) 23(17):5015-5023.
Juric et al., "Phase I Dose-Escalation Study of Taselisib, an Oral PI3K Inhibitor, in Patients with Advanced Solid Tumors" Cancer Discov. 7, 704-715, doi: 10.1158/2159-8290.CD-16-1080 (2017).
Juvekar et al., "Combining a PI3K inhibitor with a PARP inhibitor provides an effective therapy for BRCAI-related breast cancer" Cancer Discov. 2, 1048-1063, doi:10.1158/2159-8290.CD-I 1-0336 (2012).
Knight, et al. "A Pharmacological Map of the PI3-K Family Defines a Role for p110a in Insulin Sianalina". Cell (2006) 125:733-747.
Koch, et al. "N-{ 443-( 4-Fluorophenyl)pyrido(2,3-b )-pyrazin-2-y 1 )-2-pyridyl}isopropylamine" Acta Crystallogr Sect E Struct Rep Online. Oct. 1, 2009 ; 65(Pt 10): 02557.
Komoroski et al., "Dapagliflozin, a novel, selective SGLT2 inhibitor, improved glycemic control over 2 weeks in patients with type 2 diabetes mellitus" Clin Pharmacol Ther. 85, 513-519, doi:10.1038/clpt.2008.250 (2009).
Kraybill, B.C. et al. "Inhibitor scaffolds as new allele specific kinase substrates", Journal of the American Chemical Society, American Chemical Society, Washington, DC. US, vol. 124, No. 41, Oct. 16, 2002, p. 12118-28.
Kreutzberger, et al. "5-Substituierte 4-AmiNpyrimidine durch AmiNmethinylierung von Acetonitrilen" Liebigs Ann. Chem. 1977:537-544, Abstract Only.
Ma et al., "Prediagnostic body-mass index, plasma C-peptide concentration, and prostate cancer-specific mortality in men with prostate cancer: a long-term survival analysis" Lancet Oncol. 9, 1039-1047, doi:10.1016/S1470-2045(08)70235-3 (2008).
McConechy et al., "Ovarian and endometrial endometrioid carcinomas have distinct CTNNB1 and PTEN mutation profiles" Jan. 2014 (Jan. 2014), Mod Pathol.; 27(1): 128-134. doi:10.1038/modpathol.2013.107.
Namatame et al. "Antitumor profile of the PI3K inhibitor ZSTK474 in human sarcoma cell lines," Oncotarget, 2018, vol. 9(80), pp. 35141-35161.
Niswender et al., "Protein engineering of protein kinase A catalytic subunits results in the acquisition of novel inhibitor sensitivity," J. Biol Chem 277 (:12) 28916-28922 (2002).
Non-Final Office Action for U.S. Appl. No. 13/391,254 mailed on Nov. 17, 2014, 6 pages.
Non-Final Office Action for U.S. Appl. No. 16/211,803 mailed on Jul. 21, 2021, 16 pages.
Non-Final Office Action for U.S. Appl. No. 16/211,803 mailed on Jan. 23, 2020, 15 pages.
Notice of Allowance for U.S. Appl. No. 13/391,254 mailed on Apr. 8, 2015, 8 pages.
Notice of Allowance for U.S. Appl. No. 16/211,803 mailed on Aug. 10, 2022, 16 pages.
Olive et al., "Inhibition of Hedgehog signaling enhances delivery of chemotherapy in a mouse model of pancreatic cancer" Science 324, 1457-1461, doi:10.1126/science.1171362 (2009).
Patnaik et al., First-in-human phase I study of copanlisib (BAY 80-6946), an intravenous pan-class I phosphatidylinositol 3-kinase inhibitor, in patients with advanced solid tumors and non-Hodgkin's lymphomas. Ann Oncol. 27, 1928-1940, doi:10.1093/annonc/mdw282 (2016).
Pauli et al., "An emerging role for cytopathology in precision oncology" Cancer Cytopathol 124, 167-173, doi:10.1002/cncy.21647 (2016).
Pelossof et al., "Prediction of potent shRNAs with a sequential classification algorithm" Nat Biotechnol. 35, 350-353, doi:10.1038/nbt.3807 (2017).
Pollak, "Metformin and other biguanides in oncology: advancing the research agenda" Cancer prevention research 3, 1060-1065, doi:10.1158/1940-6207.CAPR-10-0175 (2010).
Pollak, "Potential applications for biguanides in oncology" J Clin Invest. 123, 3693-3700, doi:10.1172/JCI67232 (2013).
Puchalska, et al., "Multi-dimensional Roles of Ketone Bodies in Fuel Metabolism, Signaling, and Therapeutics," Cell Metabolism, Feb. 7, 2017, 25, 262-284.

(56) References Cited

OTHER PUBLICATIONS

Sam, et al. Benzoxazoles: Potent Skeletal Muscle Relaxants. J Pharm Sci. May 1964; 53:538-44.
Sampaio, "Ketogenic diet for epilepsy treatment" Arq Neuropsiquiatr. Oct. 2016; 74(10):842-848.
Saura et al., "Phase 1b study of Buparlisib plus Trastuzumab in patients with HER2-positive advanced or metastatic breast cancer that has progressed on Trastuzumab-based therapy" Clin Cancer Res. 20, 1935-1945, doi:10.1158/1078-0432.CCR-13-1070 (2014).
Singh, M.P. et al. (2000) "Synthetic Utility of Catalytic Fe(III)/Fe(II) Redox Cycling Towards Fused Heterocycles: A Facile Access to Substituted Benzimidazole, Bisbenzimidazole and Imidazopyridine Derivatives" Synthesis, 10:1380-1390.
Tanaka et al., "An unbiased cell morphology-based screen for new, biologically active small molecules," PLoS Biol. 3(5):0764-0776 (2005).
Walker et al., "Structural determinants of phosphoinositide 3-kinase inhibition by wortmannin, LY294002, quercetin, myricetin, and staurosporine" Molecular Cell, 2000, 6(4), p. 909-919.
Wikipedia "Clear-cell ovarian carcinoma", May 21, 2020 (May 21, 2020), retrieved on Dec. 28, 2022 from https://en.wikipedia.org/w/index.php?title=Clear-cell_ovarian_carcinoma&oldid=958054133.
Wu et al, "One-pot two-step microwave-assisted reaction in constructing 4,5-disubstituted pyrazolopyrimidines" Organic Letters (2003), 5(20), p. 3587-3590, Abstract Only.
Xia et al., "MetaboAnalyst 3.0—making metabolomics more meaningful" Nucleic Acids Res. 43, W251-257, doi:10.1093/nar/gkv380 (2015).
Xia et al., "Metabolomic data processing, analysis, and interpretation using MetaboAnalyst" Curr Protoc Bioinfomatics Chapter 14, Unit 14 10, doi:10.1002/0471250953.bi1410s34 (2011).
Xia et al., "MetPA: a web-based metabolomics tool for pathway analysis and visualization" Bioinformatics 26, 2342-2344, doi:10.1093/bioinformatics/btq418 (2010).
Xia et al., "Using MetaboAnalyst 3.0 for Comprehensive Metabolomics Data Analysis" Curr Protoc Bioinformatics 55, 14 10 11-14 10 91, doi:10.1002/cpbi.11 (2016).
Xu et al., "Association between markers of glucose metabolism and risk of colorectal cancer" BMJ Open 6, e011430, doi:10.1136/bmjopen-2016-011430 (2016).
Yaguchi et al., "Antitumor activity of ZSTK474, a new phosphatidylinositol 3-kinase inhibitor," J. Nall. Cancer Inst. 98 )8):545-556 (2006).
Zubarovski, et al. "BenzothiazolylqiNlines," Soviet Progress in Chemistry, 1977; 43(9), p. 62-67.
"Japanese Application Serial No. 2021-516856, Notification of Reasons for Rejection mailed May 17, 2023", W English Translation, 17 pgs.
Hopkins, B D. "Suppression of insulin feedback enhances the efficacy of PI3K inhibitors", Springer Nature Limited, vol. 560, (Aug. 23, 2018), 26 pgs.
Starks, D.C. "Phase I dose escalation study of dual PI3K mTOR inhibition by Sapanisertib and Serabelisib in combination with paclitaxel in patients with advanced solid tumors", Gynecologic Oncology 166, 3, 2022, 403-409., (Jul. 15, 2022), 7 pgs.
U.S. Appl. No. 18/300,312, filed Apr. 13, 2023, Combination Therapy for PI3K-Associated Disease or Disorder.
"Japanese Application Serial No. 2021-516856, Notification of Reasons for Refusal mailed Dec. 4, 2023", w english translation, 8 pgs.
"U.S. Appl. No. 18/300,312, Restriction Requirement mailed Jan. 23, 2024", 6 pgs.
Cockcroft et al., "Prediction of creatinine clearance from serum creatinine" Nephron. (1976) 16(1):31-41.
Dong et al., "Activation of PI3K/AKT/mTOR Pathway Causes Drug Resistance in Breast Cancer" Front Pharmacol. Mar. 15, 2021:12:628690.
Longo et al., "Nutrition, longevity and disease: From molecular mechanisms to interventions" Cell. Apr. 28, 2022; 185(9):1455-1470.

Non-Final Office Action for U.S. Appl. No. 17/983,735 dated Mar. 28, 2024, 9 pages.
Ollikainen et al., "Patterns of PIK3CA alterations in familial colorectal and endometrial carcinoma" Int J Cancer. Aug. 15, 2007; 121(4):915-920.
Patel et al., "Characterizing the Sources of Pharmacokinetic Variability for TAK-117 (Serabelisib), an Investigational Phosphoinositide 3-Kinase Alpha Inhibitor: A Clinical Biopharmaceutics Study to Inform Development Strategy" Clin Pharmacol Drug Dev. Jul. 2019; 8(5):637-646.
Sarker et al., "First-in-human phase I study of pictilisib (GDC-0941), a potent pan-class I phosphatidylinositol-3-kinase (PI3K) inhibitor, in patients with advanced solid tumors" Clin Cancer Res. Jan. 1, 2014; 21(1):77-86.
Stemke-Hale et al., "An integrative genomic and proteomic analysis of PIK3CA, PTEN, and AKT mutations in breast cancer" Cancer Res. Aug. 1, 2008; 68(15):6084-6091.
U.S. Department of Health and Human Services National Cancer Institute, "Common Terminology Criteria for Adverse Events (CTCAE)" Version 5.0, Nov. 27, 2017, 155 pages.
Xie et al., "Effects of dietary calorie restriction or exercise on the PI3K and Ras signaling pathways in the skin of mice" J Biol Chem. Sep. 21, 2007; 282(38):28025-28035.
Yuan et al., "PI3K pathway alterations in cancer: variations on a theme" Oncogene. Sep. 18, 2008; 27(41):5497-5510.
Zhao et al., "Fasting promotes acute hypoxic adaptation by suppressing mTOR-mediated pathways" Cell Death Dis. Nov 3, 2021; 12(11):1045. 13 pages.
Klil-Drori et al., "Cancer, obesity, diabetes, and antidiabetic drugs: is the fog clearing?" Nat Rev Clin Oncol. (2017) 14:85-99.
Lee et al., "PTEN gene targeting reveals a radiation-induced size checkpoint in human cancer cells" Cancer Res. (2004) 64:6906-6914.
Ma et al., "A prospective study of plasma C-peptide and colorectal cancer risk in men" J Natl Cancer Inst. (2004) 96:546-553.
Pauli et al., "Personalized In Vitro and In Vivo Cancer Models to Guide Precision Medicine," Cancer Discovery (2017) 7(5):462-477.
Starks et al., "Phase I dose escalation study of dual PI3K/mTOR inhibition by Sapanisertib and Serabelisib in combination with paclitaxel in patients with advanced solid tumors" Gynecol Oncol. (2022) Sep; 166(3):403-409.
Burris et al., "TAK-228 (formerly MLN0128), an investigational dual TORC1/2 inhibitor plus paclitaxel, with/without trastuzumab, in patients with advanced solid malignancies" Cancer Chemother Pharmacol. Aug. 2017;80(2):261-273.
Chandarlapaty et al., "AKT inhibition relieves feedback suppression of receptor tyrosine kinase expression and activity" Cancer Cell. Jan. 18, 2011; 19(1):58-71.
Cheung et al., "High frequency of PIK3R1 and PIK3R2 mutations in endometrial cancer elucidates a novel mechanism for regulation of PTEN protein stability" Cancer Discov. Jul. 2011; 1(2):170-185.
Dowling et al., "mTORC1-mediated cell proliferation, but not cell growth, controlled by the 4E-BPs" Science. May 28, 2010; 328(5982):1172-1176.
Grilley-Olson et al., "A phase Ib dose-escalation study of the MEK inhibitor trametinib in combination with the PI3K/mTOR inhibitor GSK2126458 in patients with advanced solid tumors" Invest New Drugs. Dec. 2016;34(6):740-749.
Hernandez-Prat et al., "Novel Oral mTORC1/2 Inhibitor TAK-228 Has Synergistic Antitumor Effects When Combined with Paclitaxel or PI3Ka Inhibitor TAK-117 in Preclinical Bladder Cancer Models" Mol Cancer Res. Sep. 2019;17(9):1931-1944.
Juric et al., "Convergent loss of PTEN leads to clinical resistance to a PI(3)Kα inhibitor" Nature. Feb. 12, 2015; 518(7538):240-244.
Le et al., "Systematic Functional Characterization of Resistance to PI3K Inhibition in Breast Cancer" Cancer Discov. Oct. 2016; 6(10):1134-1147.
O'Reilly et al., "mTOR inhibition induces upstream receptor tyrosine kinase signaling and activates Akt" Cancer Res. Feb. 1, 2006; 66(3):1500-1508.
Ray-Coquard et al., "Everolimus as second- or third-line treatment of advanced endometrial cancer: ENDORAD, a phase II trial of GINECO" Br J Cancer. May 14, 2013; 108(9):1771-1777.

(56) References Cited

OTHER PUBLICATIONS

Rodrik-Outmezguine et al., "mTOR kinase inhibition causes feedback-dependent biphasic regulation of AKT signaling" Cancer Discov. Aug. 2011; 1(3):248-259.

Ruvinsky et al., "Ribosomal protein S6 phosphorylation: from protein synthesis to cell size" Trends Biochem Sci. Jun. 2006;31(6):342-348.

Sanchez-Vega et al., "Oncogenic Signaling Pathways in The Cancer Genome Atlas" Cell. Apr. 5, 2018; 173(2):321-337. e10.

Schram et al., "A phase Ib dose-escalation and expansion study of the oral MEK inhibitor pimasertib and PI3K/MTOR inhibitor voxtalisib in patients with advanced solid tumours" Br J Cancer. Dec. 2018; 119(12):1471-1476.

Serra et al., "PI3K inhibition results in enhanced HER signaling and acquired ERK dependency in HER2-overexpressing breast cancer" Oncogene. Jun. 2, 2011; 30(22):2547-2557.

Shi et al., "Mammalian target of rapamycin inhibitors activate the AKT kinase in multiple myeloma cells by up-regulating the insulin-like growth factor receptor/insulin receptor substrate-1/phosphatidylinositol 3-kinase cascade" Mol Cancer Ther. Oct. 2005; 4(10):1533-1540.

So et al., "Selective inhibition of phosphoinositide 3-kinase p110α preserves lymphocyte function" J Biol Chem. Feb. 22, 2013; 288(8):5718-5731.

Sun et al., "Activation of Akt and eIF4E survival pathways by rapamycin-mediated mammalian target of rapamycin inhibition" Cancer Res. Aug. 15, 2005; 65(16):7052-7058.

Woolf et al., "Tumor Metabolism, the Ketogenic Diet and β-Hydroxybutyrate: Novel Approaches to Adjuvant Brain Tumor Therapy" Front Mol Neurosci. Nov. 16, 2016; 9:122. 11 pages.

Zhang et al., "A Pan-Cancer Proteogenomic Atlas of PI3K/AKT/mTOR Pathway Alterations" Cancer Cell. Jun. 12, 2017; 31(6):820-832. e3.

Zhang et al., "Meta-analysis of the prognostic value of p-4EBP1 in human malignancies" Oncotarget. Dec. 7, 2017; 9(2):2761-2769.

Cantley, "Abstract KN01: Keynote Lecture: PI 3-kinase links obesity, insulin resistance, and cancer" Mol Cancer Ther (2018) 17(S1):KN01, 2 pages.

Final Office Action for U.S. Appl. No. 17/983,735 mailed Oct. 17, 2024, 16 pages.

* cited by examiner

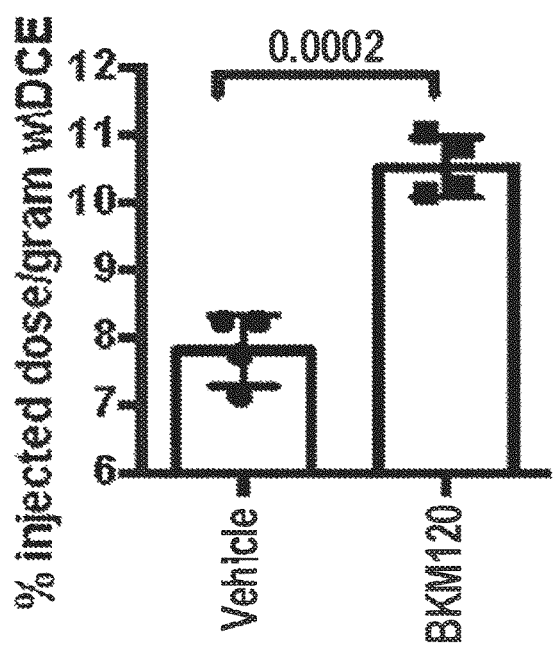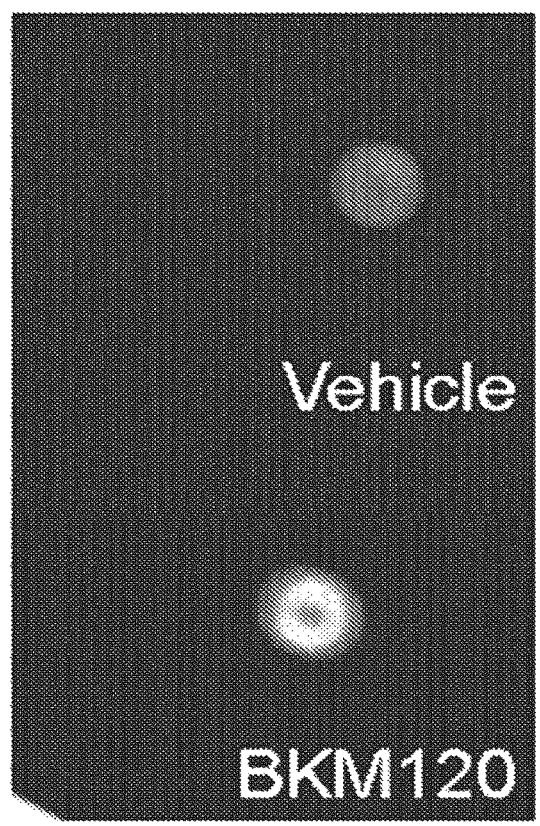
FIG. 1D-1         FIG. 1D-2

SEQUENCE LISTING

```
<160> NUMBER OF SEQ ID NOS: 5

<210> SEQ ID NO 1
<211> LENGTH: 37
<212> TYPE: DNA
<213> ORGANISM: Artificial Sequence
<220> FEATURE:
<223> OTHER INFORMATION: A synthetic oligonucleotide primer

<400> SEQUENCE: 1
tgaactcgag aaggtatatt gctgttgaca gtgagcg                             37

<210> SEQ ID NO 2
<211> LENGTH: 37
<212> TYPE: DNA
<213> ORGANISM: Artificial Sequence
<220> FEATURE:
<223> OTHER INFORMATION: A synthetic oligonucleotide primer

<400> SEQUENCE: 2
tgaactcgag aaggtatatt gctgttgaca gtgagcg                             37

<210> SEQ ID NO 3
<211> LENGTH: 22
<212> TYPE: DNA
<213> ORGANISM: Artificial Sequence
```

```
<220> FEATURE:
<223> OTHER INFORMATION: A synthetic oligonucleotide primer

<400> SEQUENCE: 3
tgtttgaatg aggcttcagt ac                                              22

<210> SEQ ID NO 4
<211> LENGTH: 97
<212> TYPE: DNA
<213> ORGANISM: Artificial Sequence
<220> FEATURE:
<223> OTHER INFORMATION: A synthetic oligonucleotide primer

<400> SEQUENCE: 4
tgctgttgac agtgagcgca ggaattataa tgcttatcta tagtgaagcc acagatgtat     60
agataagcat tataattcct atgcctactg cctcgga                             97

<210> SEQ ID NO 5
<211> LENGTH: 97
<212> TYPE: DNA
<213> ORGANISM: Artificial Sequence
<220> FEATURE:
<223> OTHER INFORMATION: A synthetic oligonucleotide primer

<400> SEQUENCE: 5
tgctgttgac agtgagcgcg gggttcatgc tgttctacaa tagtgaagcc acagatgtat     60
tgtagaacag catgaacccc atgcctactg cctcgga                             97
```

COMBINATION THERAPY FOR PI3K-ASSOCIATED DISEASE OR DISORDER

This application is a U.S. national stage filing under 35 U.S.C. § 371 from International Application No. PCT/US2019/034949, filed on May 31, 2019, and published as WO2019/232403 A1 on Dec. 5, 2019, which claims benefit of priority to the filing date of U.S. Provisional Application Ser. No. 62/679,329, filed Jun. 1, 2018, the contents of which are specifically incorporated by reference herein in their entirety.

FIELD OF THE DISCLOSURE

The present disclosure relates generally to methods of treating diseases or disorders associated with insulin-receptor/PI3K/AKT/mTOR pathway signaling, including hematologic malignancies and solid tumors. In particular, the disclosure relates to increasing the efficacy of an insulin-receptor/PI3K/AKT/mTOR pathway inhibitor by modulation of glucose metabolism either pharmacologically or with diet.

BACKGROUND

An association exists between some diseases and disorders and the insulin-receptor phosphatidylinositol kinase (phosphoinositide 3-kinase (PI3K)), protein kinase B (AKT) and mammalian target of rapamycin (mTOR) signaling pathway (called the insulin-receptor/PI3K/AKT/mTOR pathway). In cancer, mutations in PIK3CA are observed at similar frequency to mutations in KRAS (Kandoth, C. et al. Mutational landscape and significance across 12 major cancer types. *Nature* 502, 333-339, doi:10.1038/nature12634 (2013); Millis, S. Z., Ikeda, S., Reddy, S., Gatalica, Z. & Kurzrock, R. Landscape of Phosphatidylinositol-3-Kinase Pathway Alterations Across 19784 Diverse Solid Tumors. *JAMA Oncol* 2, 1565-1573, doi:10.1001/jamaoncol.2016.0891 (2016).)

Even though therapies targeting the insulin-receptor/PI3K/AKT/mTOR pathway are desirable, the medical community has struggled to identify effective compositions and methods for targeting PI3K as well as upstream and downstream regulators of insulin-receptor/PI3K/AKT/mTOR signalling. Thus, there exists a long-felt and unmet need for compositions and method for treating a disease or disorder associated with PI3K signaling. The present disclosure provides such compositions and methods, and more.

SUMMARY OF THE DISCLOSURE

The present disclosure relates generally to compositions and methods for treating a disease or disorder associated with PI3K signaling that can include administration of a modulator of glucose metabolism with or without a diet that influences the subject's metabolic state. In some cases, the method can include administering an inhibitor of at least one kinase in the insulin-receptor/PI3K/AKT/mTOR pathway and administering a modulator of glucose metabolism. In some cases, the method includes administering the pathway inhibitor and/or a modulator of glucose metabolism to a subject who consumes a ketogenic diet during treatment. The disclosure further relates to pharmaceutical compositions that can include a pathway inhibitor, modulator of glucose metabolism, or a combination thereof.

The disclosure provides a method of treating a disease or disorder associated with PI3K signaling, that includes administering to a subject in need thereof an effective amount of a modulator of glucose metabolism; and administering to the subject an effective amount of a pathway inhibitor of the insulin-receptor/PI3K/AKT/mTOR pathway.

The disclosure also provides a method of treating a disease or disorder associated with PI3K signaling, that includes administering an effective amount of a pathway inhibitor, wherein optionally the pathway inhibitor is capable of inhibiting at least one kinase in the insulin-receptor/PI3K/AKT/mTOR pathway.

The subject can consume or be administered a ketogenic diet during any of these treatments.

The disclosure also provides a pharmaceutical composition that includes a modulator of glucose metabolism and a pathway inhibitor, wherein optionally the pathway inhibitor is capable of inhibiting at least one kinase in the insulin-receptor/PI3K/AKT/mTOR pathway.

The disclosure also provides a method of inhibiting cell proliferation or cell-proliferative disease, that includes administering to a subject an effective amount of a glucose-uptake inhibitor; and administering to the subject an effective amount of a PI3K inhibitor.

The subject can be in need of treatment or the treatment can be performed to inhibit the onset of a disease or condition.

The disclosure also provides a method of inhibiting cell proliferation or a cell-proliferative disease, that involves administering to a subject an effective amount of a PI3K inhibitor, wherein the subject consumes a ketogenic diet during treatment. In some embodiments, the modulator of glucose metabolism is a glucose-uptake inhibitor. For example, such a glucose-uptake inhibitor can be a sodium-glucose-linked transport protein 1 (SGLT1) inhibitor, a sodium-glucose-linked transport protein 2 (SGLT2) inhibitor, a dual SGLT1/SGLT2 inhibitor, or a combination thereof.

In some embodiments, the glucose-uptake inhibitor is selected from dapagliflozin, empagliflozin, canagliflozin, ipragliflozin, tofogliflozin, sergliflozin etabonate, remogliflozin etabonate, ertugliflozin, sotagliflozin, conagliflozin, or a combination thereof.

In some embodiments, the modulator of glucose metabolism is metformin.

In some embodiments, the modulator of glucose metabolism is an insulin receptor/insulin like growth factor 1 (IGF1) receptor inhibitor, wherein optionally the insulin receptor/IGF1 receptor inhibitor is linsitinib (OSI-906).

In some embodiments, the pathway inhibitor is selected from idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, apelisib, MK2206, linsitinib (OSI-906), or a combination thereof.

In some embodiments, the PI3K inhibitor is selected from the group consisting of idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, and apelisib.

In some embodiments, the disease or disorder associated with PI3K signaling is a cancer or cell-proliferative disorder, a metabolic disorder, a neurodegenerative disease, an inflammatory disease, or a combination thereof.

In some embodiments, disruption of systemic glucose homeostasis improves efficacy of pathway-inhibitor treatment compared to pathway inhibitor alone.

In some embodiments, the inhibition of cell proliferation or cell-proliferative disease is enhanced compared to administration of the PI3K inhibitor without a glucose-uptake inhibitor.

BRIEF DESCRIPTION OF THE FIGURES

FIG. 1A-1D demonstrate that treatment with PI3K inhibitors causes systemic feedback resulting in increases in blood glucose and insulin. FIG. 1A graphically illustrates blood glucose levels measured over time in mice treated with the indicated PI3K inhibitor compounds (N=5/arm, p-value<0.0001 by Two-Way ANOVA for all blood glucose curves of mice in treatment cohorts as compared to vehicle). To mimic clinical treatment these mice were not starved for this assay. FIG. 1B graphically illustrates insulin levels, measured over time in mice treated with the indicated PI3K inhibitor compounds (N=5/arm, p-value<0.0001 by Two-Way ANOVA for all blood glucose curves of mice in treatment cohorts as compared to vehicle). To mimic clinical treatment these mice were not starved for this assay. FIG. 1C graphically illustrates c-Peptide levels accessed from serum samples taken from the same animals as used for FIG. 1A-1B at the end of the time course, 240 min, as a representative of area under the curve insulin release. p-values comparing vehicle treatment to buparlisib (BKM120), Alpelisib (BYL719), and taselisib (GDC-0032), by t-test were 0.017, <0.0001, and 0.007 respectively. FIG. 1D-1 graphically illustrates the quantity of fluorodeoxyglucose tracer detected via fluorodeoxyglucose-Positron Emission Tomography (FDG-PET) scans (shown in FIG. 1D-2) of orthotopically implanted Kras-Tp53-Pdx-Cre (KPC) tumors imaged 90 minutes after a single treatment with buparlisib (BKM120) (N=4/arm). These result demonstrate that PI3K inhibitor-induced spikes in insulin caused an increase in glucose uptake in the tumors of these animals in the acute setting after a single dose of BKM120 (p-value=0.0002, by t-test).

FIG. 2A shows a Western blot of proteins from orthotopic Kras-Tp53-Pdx-Cre (KPC) cell lines K8484 and K8082 treated with or without the PI3K inhibitor BKM120 (1 uM) and/or insulin (10 ng/ml), further illustrating the physiologic responses to insulin as observed in FIG. 1A-1D. FIG. 2B graphically illustrates results of a proliferation assay of the KPC cell line K8484 grown in the presence or absence of insulin (10 ng/ml) and BKM120 (1 uM). p-values determined by ANOVA comparing conditions+/−insulin are shown. FIG. 2C graphically illustrates results of a proliferation assay of KPC cell lines K8082 grown in the presence or absence of insulin (10 ng/ml) and BKM120 (1 uM). p-values determined by ANOVA comparing conditions+/−insulin are shown.

FIG. 3A-3G demonstrate that targeting the PI3K inhibitor induces glucose/insulin feedback in vivo. FIG. 3A graphically illustrates blood glucose levels over time of wildtype c57/b16 mice baring syngeneic K8484 KPC allografted tumors after treatment with a single dose of BKM120 with metformin pretreatment, SGLT2-inhibitor (SGLT2i) pretreatment, or a ketogenic diet (N=4/arm). p-values calculated by Two-way repeated measures ANOVA for metformin, SGLT2i, and the ketogenic diet were 0.2136 (not significant), <0.0001, and 0.007 respectively. FIG. 3B graphically illustrates blood levels of c-peptide of the same mice as for FIG. 3A taken 180 minutes after treatment with BKM120. p-values calculated by unpaired t-test for metformin, SGLT2i, and ketogenic diet were 0.7566 (not significant), 0.0386, and 0.0117 respectively. FIG. 3C shows immunohistochemical images illustrating pS6 (ser-235) expression to observe the level of active PI3K signaling in these tumors.

FIG. 3D graphically illustrates quantification of the staining observed in FIG. 3C shown as positive cells per high power field (20 fields/arm taken as 5 high power images averaged for each of the 4 mice). p-values comparing pS6 positive cells in BKM120 alone treated tumors as compared to those treated with BKM120 in combination with metformin, SGLT2i, or the ketogenic diet were 0.6186, <0.0001, and <0.0001 respectively. FIG. 3E-1 to FIG. 3E-4 show IVIS images of luciferase reporter luminescence in mice with KPC K8484 tumors after 12 days of treatment with PI3Kα specific inhibitor BYL-719 alone or in combination with other agents.

FIG. 3E-1 shows IVIS images of luciferase reporter luminescence in mice with KPC K8484 tumors after 12 days of treatment with PI3Kα specific inhibitor BYL-719 alone. FIG. 3E-2 shows IVIS images of luciferase reporter luminescence in mice with KPC K8484 tumors after 12 days of treatment with PI3Kα specific inhibitor BYL-719 combined with metformin for ten days prior to BYL-719 treatment (N=10 tumors/arm). FIG. 3E-3 shows IVIS images of luciferase reporter luminescence in mice with KPC K8484 tumors after 12 days of treatment with PI3Kα specific inhibitor BYL-719 combined with a ketogenic diet for ten days prior to BYL-719 treatment (N=10 tumors/arm). FIG. 3E-4 shows IVIS images of luciferase reporter luminescence in mice with KPC K8484 tumors after 12 days of treatment with PI3Kα specific inhibitor BYL-719 combined with canagliflozin (SGLT2i) for ten days prior to BYL-719 treatment (N=10 tumors/arm). Dietary interventions in this study were initiated at time of tumor implantation, BYL-719 treatment was initiated nine days after implantation. FIG. 3F graphically illustrates quantification of luminescence from the images of these tumors. FIG. 3G graphically illustrates survival of these animals showing that the addition of either SGLT2 inhibitor or administration of ketogenic diet to treatment with BYL-719 increases overall survival of these animals as determined by Log-rank (Mantel-Cox) test, p-value=0.0019 and <0.0001 respectively.

FIG. 4A graphically illustrates K8484 KPC tumor volume (where the tumor cells express doxycycline inducible hairpins targeting Renilla (ShRenilla) or Insulin Receptor (ShIR)) in mice treated with doxycycline and with the PI3K inhibitor BYL-719 and/or with a ketogenic diet. Tumors in this experiment were allowed to grow for fourteen days reaching an average size greater than 1 cm$^3$ at which point diet, doxycycline induction of hairpin expression, and PI3K inhibitor treatments were initiated (N>5 tumors/arm as indicated). FIG. 4B graphically illustrates ES272 Pik3ca mutant breast cancer allograft tumor volume treated with BYL-719 and/or insulin along with the ketogenic (keto) as indicated. Tumors in this experiment were allowed to grow for 10 days after implantation into mice prior to the initiation of diet and indicated treatments. FIG. 4C graphically illustrates tumor volume of subject-derived endometrial xenografts (PDX) treated with BKM120 and/or while having a ketogenic diet (N=5/arm). ANOVA comparison between the BKM120 alone and BKM120 plus ketogenic diet treated mice indicates that the addition of ketogenic diet significantly enhances treatment efficacy in this model (p-value=0.0028). FIG. 4D illustrates the histology of phospho-Insulin Receptor (pINSR), phospho-AKT (pAKT), phospho-S6 (pS6), cleaved caspase 3 (Cl. Casp 3), and Ki67 of tumors taken 4 hours after the last treatment with Vehicle, ketogenic diet, BKM120, or the combination of the ketogenic diet with BKM120 (BKM120/Keto). FIG. 4E graphically illustrates the quantification of phospho-Insulin Receptor (pINSR), phospho-AKT (pAKT), phospho-S6 (pS6), cleaved caspase 3 (Cl. Casp 3), and ki67 of the tumors shown in FIG. 4D taken 4 hours after the last treatment with Vehicle, ketogenic diet, BKM120, or the combination of the ketogenic diet with BKM120 (BKM120/Keto). Quantification is depicted as score per high powered field, four images were taken for each of the five mice. p-values from t-tests comparing the blinded scoring in BKM120 treated tumors as compared to those treated with BKM120 with the ketogenic diet were 0.005, 0.005, 0.017 and 0.028 and for pINSR, pAKT, pS6 and Cl. Casp 3 respectively.

FIG. 5A graphically illustrates blood glucose levels over time where time 0 is the time of treatment with the indicated inhibitor. FIG. 5B graphically illustrates blood glucose levels over time where time 0 is the time of treatment with additional inhibitors as indicated. FIG. 5C graphically illustrates c-peptide levels from mice in FIG. 5A taken 240 and 180 minutes after treatment with inhibitors, as a surrogate for total insulin release in these animals, showing that the PI3K inhibitors and IGFR/INSR inhibitors dramatically increase insulin release in these animals. In all cases compounds that caused acute increases in blood glucose levels also increased serum insulin levels. FIG. 5D graphically illustrates c-peptide levels from the mice described in FIG. 5B taken 240 and 180 minutes after treatment with inhibitors, as a surrogate for total insulin release in these animals, showing that the PI3K inhibitors and IGFR/INSR inhibitors dramatically increase insulin release in these animals. In all cases compounds that caused acute increases in blood glucose levels also increased serum insulin levels.

FIG. 6A-6G demonstrate the impact of the feedback levels of insulin observed in FIG. 1A-D upon BKM120 efficacy in vitro. FIG. 6A-1 graphically illustrates cellular proliferation in minimal growth media of MDA-MB-468 breast cancer cells whose growth is partially rescued by the addition of the observed feedback levels of insulin (10 ng/ml) induced by BKM120 in mice. FIG. 6A-2 graphically illustrates proliferation in minimal growth media of BT-549 breast cancer cells whose growth is partially rescued by the addition of the observed feedback levels of insulin (10 ng/ml) induced by BKM120 in mice. FIG. 6A-3 graphically illustrates proliferation in minimal growth media of PC-3 prostate adenocarcinoma cells whose growth is partially rescued by the addition of the observed feedback levels of insulin (10 ng/ml) induced by BKM120 in mice. FIG. 6B graphically illustrates cell viability assay demonstrating the effects that these feedback levels of insulin have upon 2 subject (Pt)-derived organoid cultures (Pt A and Pt B) being treated in a dose response with BKM120 as measured by cell titer-glo at 96 hours. FIG. 6C graphically illustrates proliferation (percent confluence) in minimal growth media partially rescued by the addition of the observed feedback levels of insulin induced by BKM120 in mice as observed in FIG. 1A-D. FIG. 6D shows proliferation (percent confluence) of HCT116-neo cells with and without treatment with the physiologically observed levels of insulin (10 ng/ml) and treatment with clinically relevant PI3K inhibitors GDC-0032 and BYL-719. FIG. 6E graphically illustrates proliferation (percent confluence) of HCT116 PTEN knockout (KO) cells with and without treatment with the physiologically observed levels of insulin (10 ng/ml) and treatment with clinically relevant PI3K inhibitors GDC-0032 and BYL-719. FIG. 6F shows proliferation (percent confluence) of DLD1-Neo under the indicated treatment conditions, which were the same as in FIG. 6G. FIG. 6G graphically illustrates proliferation (percent confluence) DLD-1 PTEN Knockout cells under the same treatment conditions as in FIG. 6F. Of note, the loss of PTEN in the isogenic sets of colon cancer lines does not uniformly alter the response to insulin in the setting of PI3K inhibition. In the context of PTEN loss, physiologic levels of insulin can restore normal proliferation in HCT116s despite the presence of PI3K inhibitors.

FIG. 7A graphically illustrates blood glucose curves of mice from FIG. 3E-3G treated with control diet, ketogenic diet, metformin (250 mg/kg), or canagliflozin (SGLT2i) (6 mg/kg), after the first dose of BYL-719 (45 mg/kg). FIG. 7B graphically illustrates tumor volumes of mice treated with the metabolic modifying agents as shown in FIG. 3A-3G without PI3K inhibitors. FIG. 7C graphically illustrates average tumor volume (lines) with scatter (points) for each of the indicated treatment cohorts. FIG. 7D graphically illustrates tumor volumes from an independent experiment of mice treated daily with BKM120 with or without 6 mg/kg of Canagliflozin administered 60 minutes prior to the PI3K treatment so that peak SGLT2 inhibition is aligned with peak blood glucose levels post PI3K inhibitor treatment. FIG. 7E graphically illustrates blood ketone of mice shown in FIG. 3A-D after a single treatment with BKM120 with or without pretreatment with metformin, Canagliflozin, or the ketogenic diet as indicated. FIG. 7F graphically illustrates triglyceride levels as determined by Calorimetric assay of mice shown in FIG. 3A-D after a single treatment with BKM120 with or without pretreatment with metformin, Canagliflozin, or the ketogenic diet as indicated.

FIG. 8A shows a Western blot of cell lysates from K8484 cells used to generate xenografts in FIG. 4A after treatment with doxycycline to induce the sh-*Renilla* and sh-INSR hairpins as indicated. FIG. 8B graphically illustrates tumor volumes of the individual mice allografted with KPC-K8484 tumors as measured by caliper over time. FIG. 8C graphically illustrates a survival curve of mice in FIG. 8A. FIG. 8D graphically illustrates blood glucose levels from mice 240 minutes after the indicated treatments. Two of the glucose measurements in the OSI-906 and BKM120 were beyond the range of the detector (e.g. >600). FIG. 8E graphically illustrates c-peptide levels from mice 240 minutes after the indicated treatments. FIG. 8F graphically illustrates the mass of mice over the course of the indicated treatments. As has been previously published mice lose 10-20% of their mass upon initiation of the ketogenic diet. FIG. 8G graphically illustrates tumor volume for the tumors in FIG. 8A for treatment with OSI-906, a INSR/IGFR inhibitor, or GDC-0032 with or without a keto diet. Treatment efficacy was significantly improved in PIK3CA+MYC mutant murine breast tumor allografts, ES-278, grown in wild-type c57/bl6 when combined with ketogenic diet. FIG. 8H graphically illustrates tumor volumes of wildtype c57/bl6 mice baring KPC allografted tumors as measured by calipers over time. Mice were treated as indicated with combinations of BYL- 719, the ketogenic diet, or insulin as in FIG. 4B. Mice in the ketogenic-BYL719-insulin cohort lost >20% of their body mass over the 1 week of treatment so the experiment was terminated at day 7.

FIG. 9A graphically illustrates tumor volume over time of a subject-derived endometrial xenografts (PDX) derived from a subject with bladder cancer (Subject C) and treated with the pan PI3K inhibitor GDC-0941 or the PI3K-β sparing compound GDC-0032 alone or with a ketogenic diet. Lines indicate average tumor volume of each treatment group, points indicate individual tumor volumes over time. Tumors were allowed to grow until their diameters were greater than 0.6 cm prior to the initiation of treatment. FIG. 9B graphically illustrates the mass of the tumors (from FIG. 9A) taken at the time harvest on day 12. FIG. 9C graphically illustrates tumor growth over time of mice with orthotopic allografts of an PIK3CA (H1047R) mutant murine breast cancer, ES272, treated as indicated with BKM120 alone or in combination with a ketogenic diet. FIG. 9D graphically illustrates tumor mass at harvest from mice with orthotopic allografts of an PIK3CA (H1047R) mutant murine breast cancer, ES272, treated as indicated with BKM120 alone or in combination with a ketogenic diet. FIG. 9E graphically illustrates the mass of the mice described in FIG. 9C-9D over time.

FIG. 10A graphically illustrates survival of mice with KPC K8082 allografts grown in the flank and treated as indicated with BAY 80-6946 alone and in combination with a ketogenic diet pretreatment as indicated (p-value comparing BAY 80-6946 to the combination of BAY 80-6946 with ketogenic diet in this study is 0.0019 by Mantel-Cox Log-rank test). FIG. 10B graphically illustrates the volume each tumor in this cohort graphed as individual lines. FIG. 10C graphically illustrates single blood glucose measurements of samples taken from the animals in FIGS. 10B and 10C at 240 min after treatment. FIG. 10D graphically illustrates c-peptide measurements of samples taken from the animals in FIGS. 10B and 10C at 240 min after treatment. FIG. 10E graphically illustrates the mass of the animals described in FIG. 10A-10D over the time on treatment. Tumors were allowed to grow until their diameters were >0.6 cm prior to the initiation of treatment.

FIG. 11A shows IVIS images of AML burden (as reported by mCherry) in mice over time of the indicated treatment. FIG. 11B graphically illustrates survival of mice having the syngeneic model of AML treated with BKM120 alone or in combination with a ketogenic diet. Individual lines are shown for initiation of ketogenic diet before (pre) or at the same time as the initiation of BKM120 treatment (Co), both demonstrate that BKM120 efficacy is significantly enhanced by the addition of the ketogenic diet (p=0.0316 and 0.349 for pre and co respectively). The asterisks (*) denote mice that were sacrificed due to paralysis resulting from AML infiltrating the CNS rather than deaths typically seen in these mice due to tumor burden. Of note the mice in the BKM+Ketogenic diet group were frequently sacrificed due to paralysis which was not frequently a cause of mortality in the other treatment groups. FIG. 11C graphically illustrates disease burden of AML model shown in FIG. 4A-4E as measured by percent AML cells in bone marrow.

FIG. 11D graphically illustrates spleen weights across the treatment groups. FIG. 11E graphically illustrates AML burden in mice that were pretreated with BKM120 and/or a ketogenic diet to demonstrate that the effects observed in the AML studies are not the result of implantation issues related to the pretreatment. FIG. 11F shows images of mice treated as indicated with BKM120 or the ketogenic diet where the diet and BKM120 therapy were initiated on the same day (co-treatment).

FIG. 12A graphically illustrates blood glucose levels in wildtype c57/bl6 mice baring syngeneic K8484 KPC allografted tumors after treatment with a single dose of BKM120 after metformin pretreatment, SGLT2-inhibitor (SGLT2i) pretreatment, a ketogenic diet alone, or combinations thereof (N=4/arm). FIG. 12B graphically illustrates ketone levels in wildtype c57/bl6 mice baring syngeneic K8484 KPC allografted tumors after treatment with a single dose of BKM120 with metformin pretreatment, SGLT2-inhibitor (SGLT2i) pretreatment, a ketogenic diet alone, or combinations thereof (N=4/arm). FIG. 12C graphically illustrates c-peptide levels in wildtype c57/bl6 mice baring syngeneic K8484 KPC allografted tumors after treatment with a single dose of BKM120 with metformin pretreatment, SGLT2-inhibitor (SGLT2i) pretreatment, a ketogenic diet alone, or combinations thereof (N=4/arm).

DETAILED DESCRIPTION

Figure 1A:
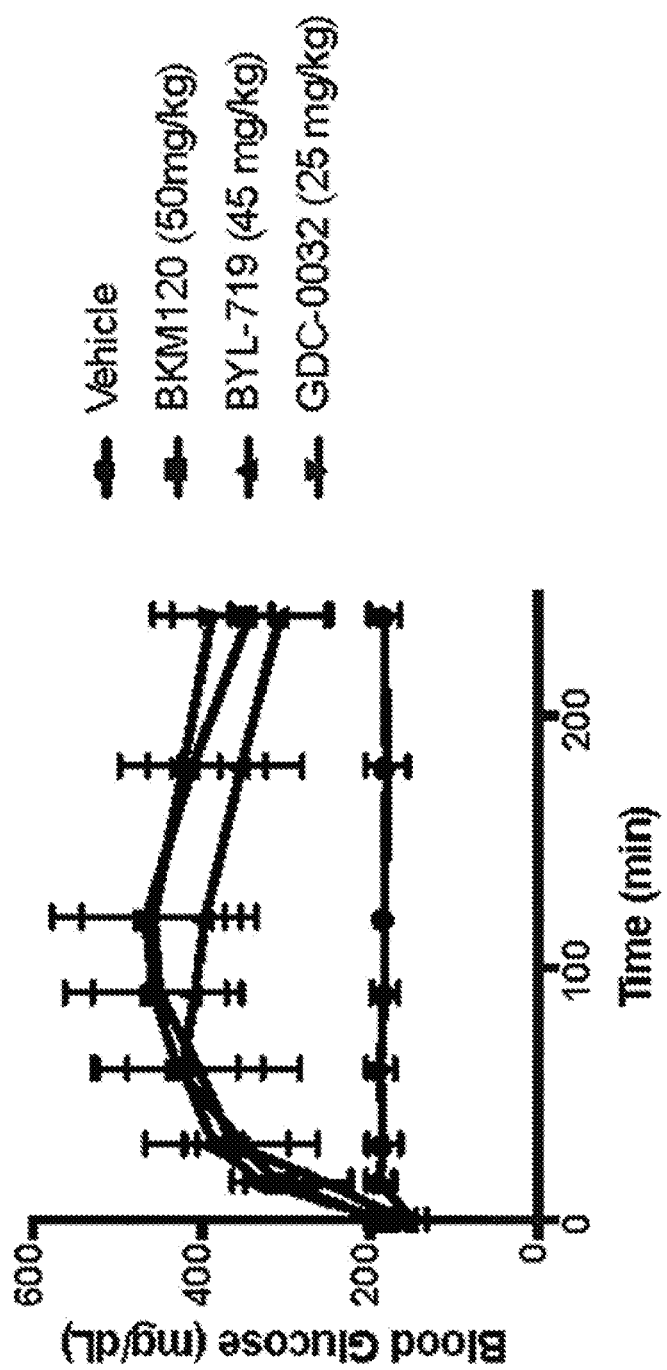

The present disclosure relates generally to compositions and methods for treating a disease or disorder associated with PI3K signaling. The methods can include administration of a modulator of glucose metabolism, use of a diet that influences the subject's metabolic state, or a combination thereof. In some cases, the method includes co-administering a pathway inhibitor (such as an inhibitor of at least one kinase in the insulin-receptor/PI3K/AKT/mTOR pathway) and administering a modulator of glucose metabolism. In some cases, the method of treating includes administering the pathway inhibitor to a subject who consumes a ketogenic diet during treatment. The disclosure further relates to pharmaceutical compositions comprising a pathway inhibitor and modulator of glucose metabolism.

Some studies indicate that administration of various modulators of glucose metabolism alone or administration of various inhibitors of the insulin-receptor/PI3K/AKT/mTOR pathway can be associated with an unfavorable safety profile and suboptimal anti-cancer activity. However, the types of combination therapies described herein can reduce or eliminate such side effects. For example, the inhibitors may be administered in lower doses or for shorter duration when combined with the other therapeutic agents and/or a ketogenic diet. Such combination therapies can provide reduced toxicity and avoid some of the side effects of monotherapies of drug-only therapies.

The insulin-receptor/PI3K/AKT/mTOR pathway has not proven to be as druggable a target as those in the field would have hoped given its central role in cellular signaling. More than twenty PI3K inhibitors have entered clinical trials but only two (idelalisib and copanlisib) have been approved for use in cancer therapy. These agents are effective for treating lymphomas by primarily targeting the PIK3CD encoded enzyme p110Δ rather than the more broadly mutated PIK3CA-encoded enzyme, p110α. Several drugs that target p110α have entered approval trials, however the toxicity profile has been a challenge to manage and the responses have not correlated with PIK3CA mutations as would be expected. (Massacesi, C. et al. PI3K inhibitors as new cancer therapeutics: implications for clinical trial design. *Onco Targets Ther* 9, 203-210 (2016); Mayer, I. A. et al. A Phase Ib Study of Alpelisib (BYL719), a PI3Kalpha-Specific Inhibitor, with Letrozole in ER+/HER2− Metastatic Breast Cancer. *Clin Cancer Res* 23, 26-34 (2017)).

As disclosed herein, pharmacologic blockade of PI3K elevates serum glucose and raises serum insulin. This hyperinsulinemia can re-activate the PI3K and mTOR signaling pathway in tumors within an hour or two of dosing, thereby compromising the effectiveness of PI3K blocking. The present disclosure provides a variety of interventions to reduce serum insulin. For example, the methods described herein can include administration of metformin, a Na$^+$/Glucose co-transporter inhibitor, use of a ketogenic diet, or a combination thereof. As shown herein, a diverse group of human tumor organoids and cell lines grown as tumors in vivo, as well as genetically engineered tumors exhibit enhanced responses to PI3K inhibitors when the subjects were on a ketogenic diet. The enhanced responses were found in tumors with or without PIK3CA mutations. These results indicate that treating subjects with modulators of glucose metabolism and/or maintaining subjects on ketogenic diets enhances subject responses to PI3K inhibitors across a wide spectrum of cancers.

Modulators of glucose metabolism and ketogenic diet improve drug efficacy with pathway inhibitors, including an array of agents that target the PI3K pathway in addition to BKM120 and BYL719, including the pan PI3K inhibitor GDC-0941, the PI3K-R sparing compound GDC-0032, the mTOR/PI3K dual inhibitor GDC-0980, the orally bioavailable inhibitor of class I PI3K alpha isoform serabelisib (TAK-117), and the recently approved PI3K-α/δ inhibitor Copanlisib.

For example, the addition of the ketogenic diet to BKM120 reduced immunohistochemical markers of insulin signaling compared to tumors treated with BKM120 alone in PTEN/PIK3CA mutant endometrial PDX tumors. In these tumors, the ketogenic diet enhanced the ability of BKM120 to reduce levels of the phosphorylated insulin receptor, the phosphorylated AKT, and the phosphorylated S6. Such reduction in signaling correlated with decreased levels of cell proliferation as shown by Ki67 staining, and increased levels of apoptosis as indicated by cleaved caspase 3 staining.

In one embodiment, the disclosure includes a method of inhibiting cell proliferation, comprising contacting a cell with an effective amount of a modulator of glucose metabolism; and contacting the cell with an effective amount of at least one inhibitor of an insulin-receptor/PI3K/AKT/mTOR pathway, to thereby inhibit cell proliferation. In certain embodiments, at least one inhibitor inhibits at least one kinase in the insulin-receptor/PI3K/AKT/mTOR pathway to thereby inhibit cell proliferation. In particular embodiments, the insulin-receptor/PI3K/AKT/mTOR pathway is a mammalian, e.g., human, insulin-receptor/PI3K/AKT/mTOR pathway. The method may be practiced in vivo, ex vivo, or in vitro, in various embodiments.

In another embodiments, the disclosure includes a method of treating a cell proliferative disease, comprising: administering to a subject in need thereof an effective amount of at least one inhibitor of an insulin-receptor/PI3K/AKT/mTOR pathway; and administering to the subject a ketogenic diet and/or at least one modulator of glucose metabolism, to thereby inhibit cell proliferation in the subject. In certain embodiments, the subject is administered the ketogenic diet. In certain embodiments, the subject is administered the modulator of glucose metabolism. In certain embodiments, the subject is administered both the ketogenic diet and the modulator of glucose metabolism. In certain embodiments, at least one inhibitor inhibits at least one kinase in the insulin-receptor/PI3K/AKT/mTOR pathway to thereby inhibit cell proliferation. In particular embodiments, the insulin-receptor/PI3K/AKT/mTOR pathway is a mammalian, e.g., human, insulin-receptor/PI3K/AKT/mTOR pathway.

In particular embodiments of any of the methods disclosed herein, "administration" includes providing the pathway inhibitor, modulator of glucose metabolism, and/or ketogenic diet to the subject, e.g., to be ingested or administered at a later time, or providing a prescription for the pathway inhibitor, modulator of glucose metabolism, and/or ketogenic diet to the subject. In certain embodiments, "administration" of the ketogenic diet comprises instructing the subject to follow a ketogenic diet.

Methods and compositions disclosed herein can be used to increase the effectiveness of treatment with a pathway inhibitor (e.g., an inhibitor of the insulin-receptor/PI3K/AKT/mTOR signaling pathway). Thus, the disclosure provides a method for increasing the effectiveness or efficacy of treatment with a pathway inhibitor (e.g., an inhibitor of the insulin-receptor/PI3K/AKT/mTOR signaling pathway). Such a method can include treating a subject with an effective amount of the pathway inhibitor and optionally an effective amount of a modulator of glucose metabolism. The disclosure also provides a method for increasing the effectiveness or efficacy of treatment with a pathway inhibitor (e.g., an inhibitor of the insulin-receptor/PI3K/AKT/mTOR signaling pathway). Such a method can include treating a subject with an effective amount of the pathway inhibitor, wherein the subject consumes a ketogenic diet during treatment. The subject can be in need of such treatment. Alternatively, treatment can be used to reduce the incidence or onset of disease in the subject.

Methods and compositions disclosed herein may allow the use of a lower dosage of a pathway inhibitor. Thus, the disclosure provides a method for treating a disease or disorder associated with PI3K signaling, comprising administering to a subject in need thereof an effective amount of the pathway inhibitor (e.g., an inhibitor of the insulin-receptor/PI3K/AKT/mTOR signaling pathway) and an effective amount of a modulator of glucose metabolism, wherein the effective amount of the pathway inhibitor is a lower amount than the amount effective in the absence of treatment with the modulator of glucose metabolism.

The disclosure also provides a method for treating a disease or disorder associated with PI3K signaling, comprising administering to a subject in need thereof an effective amount of the pathway inhibitor (e.g., an inhibitor of the insulin-receptor/PI3K/AKT/mTOR signaling pathway) wherein the subject consumes a ketogenic diet during treatment, wherein the effective amount of the pathway inhibitor is a lower amount than the amount effective in the absence of the subject consuming the ketogenic diet during treatment. In certain embodiments, the effective amount of the pathway inhibitor is less than 90%, less than 80%, less than 70%, less than 60%, less than 50%, less than 40%, or less than 30%, when used in combination with the modulator of glucose metabolism and/or ketogenic diet, than is the amount of the pathway inhibitor when used alone.

Methods and compositions disclosed herein may allow for less frequent administration of a pathway inhibitor. Thus, the disclosure provides a method for treating a disease or disorder associated with PI3K signaling, comprising administering to a subject in need thereof an effective amount of the pathway inhibitor (e.g., an inhibitor of the insulin-receptor/PI3K/AKT/mTOR signaling pathway) and an effective amount of a modulator of glucose metabolism, wherein the pathway inhibitor is administered less frequently than the frequency effective in the absence of treatment with the modulator of glucose metabolism. The disclosure also provides a method for treating a disease or disorder associated with PI3K signaling, comprising administering to a subject in need thereof an effective amount of a pathway inhibitor (e.g., an inhibitor of the insulin-receptor/PI3K/AKT/mTOR signaling pathway) wherein the subject consumes a ketogenic diet during treatment, wherein the pathway inhibitor is administered less frequently than the frequency effective in the absence of the subject consuming the ketogenic diet during treatment. For example, at least one, or at least two, or at least three, or at least four, or at least five, or at least six, or at least seven, or at least eight, or at least ten, or at least thirteen, or at least fifteen fewer doses of the pathway inhibitor and/or the modulator of glucose metabolism can be administered over a duration of treatment than when the pathway inhibitor or the modulator of glucose metabolism is administered alone.

Diseases or Disorders Associated with PI3K Signaling

The term "disease or disorder associated with PI3K signaling" is intended to be construed expansively as referring to a disease or disorder caused by gain of function or loss of function in one or more members of the insulin-receptor/PI3K/AKT/mTOR pathway. The "disease or disorder associated with PI3K signaling" is a disease or disorder of a mammal such as a human, a domesticated animal, a zoo animal, or an experimental animal.

The term "disease or disorder associated with PI3K signaling" is not limited to specific forms of PI3K. There are multiple PI3K genes and the phrase encompasses diseases and or disorders associated with any of them. The human PI3K genes include at least the genes listed in Table 1.

TABLE 1

PI3K genes

| group | gene | protein | aliases |
|---|---|---|---|
| class 1 catalytic | PIK3CA | PI3K, catalytic, alpha polypeptide | p110-α |
| | PIK3CB | PI3K, catalytic, beta polypeptide | p110-β |
| | PIK3CG | PI3K, catalytic, gamma polypeptide | p110-γ |
| | PIK3CD | PI3K, catalytic, delta polypeptide | p110-δ |
| class 1 regulatory | PIK3R1 | PI3K, regulatory subunit 1 (alpha) | p85-α |
| | PIK3R2 | PI3K, regulatory subunit 2 (beta) | p85-β |
| | PIK3R3 | PI3K, regulatory subunit 3 (gamma) | p55-γ |
| | PIK3R4 | PI3K, regulatory subunit 4 | p150 |
| | PIK3R5 | PI3K, regulatory subunit 5 | p101 |
| | PIK3R6 | PI3K, regulatory subunit 6 | p87 |
| class 2 | PIK3C2A | PI3K, class 2, alpha polypeptide | PI3K-C2α |
| | PIK3C2B | PI3K, class 2, beta polypeptide | PI3K-C2β |
| | PIK3C2G | PI3K, class 2, gamma polypeptide | PI3K-C2γ |
| class 3 | PIK3C3 | PI3K, class 3 | Vps34 |

The term "disease or disorder associated with PI3K signaling" is not limited to diseases or disorders caused directly by gain of function or loss of function in PI3K but rather encompasses diseases and disorders caused by gain of function or loss of function in other genes of the insulin-receptor/PI3K/AKT/mTOR pathway. Upstream and downstream regulators of PI3K signaling include many druggable targets, such as signaling receptors, protein kinase B (known as AKT), mechanistic target of rapamycin (mTOR), as well as others.

The term "disease or disorder associated with PI3K signaling" is not limited to particular disease pathologies. Pathologically diverse diseases and disorders often have common mechanistic underpinnings. Mechanism-based treatments therefore are conventionally defined in terms of the target mechanism rather than by the tissue origin or pathological characteristics of the disease or disorder.

The diseases and disorders associated with PI3K signaling therefore include various types of disease or disorder. In one embodiment, a disease or disorder associated with PI3K signaling is a cell proliferative disease. In one embodiment, a disease or disorder associated with PI3K signaling is a neurodegenerative disease. In one embodiment, a disease or disorder associated with PI3K signaling is an inflammatory disease or condition. In one embodiment, a disease or disorder associated with PI3K signaling is a metabolic disease.

In some embodiments, the disease or disorder associated with PI3K signaling is a cell proliferative disease including, but not limited to, one or more leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphomas (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular carcinoma, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma), or a combination thereof.

In some embodiments, the disease or disorder associated with PI3K signaling is a neurodegenerative disease including, but not limited to, brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infraction including embolic occlusion and thrombotic occlusion as well as intracranial hemorrhage of any type, intracranial and intravertebral lesions, hereditary cerebral angiopathy, hereditary amyloid, Down's syndrome, macroglobulinemia, secondary familial Mediterranean fever, Muckle-Wells syndrome, multiple myeloma, pancreatic-related amyloidosis, cardiac-related amyloidosis, chronic hemodialysis arthropathy, Finnish amyloidosis, Iowa amyloidosis, or a combination thereof.

In some embodiments, the disease or disorder associated with PI3K signaling is an inflammatory disorder including, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema, ileitis, ulcerative colitis, Barrett's syndrome, Crohn's disease, or a combination thereof.

In some embodiments, the disease or disorder associated with PI3K signaling is a metabolic disease including, but not limited, Type II diabetes, insulin resistance cardiovascular disease, arrhythmia, atherosclerosis, coronary artery disease, hypertriglyceridemia, dyslipidemia, retinopathy, nephropathy, neuropathy, obesity, macular edema, or a combination thereof.

In some embodiments of the methods of the present disclosure, the subject is treatment naïve. In some embodiments, the subject is resistant to hyperglycemia. In some embodiments, the subject is not hyperglycemic. In some embodiments, the subject is not hyperglycemic prior to treatment. In some embodiments, the subject is hypoglycemic. In some embodiments, the subject exhibits glycemic control. In some embodiments, the disease or disorder associated with PI3K signaling is associated with impaired glucose hemostasis. In some embodiments, the disease or disorder associated with PI3K signaling is associated with impaired glucose homeostasis. In some embodiments, the disease or disorder associated with PI3K signaling is associated with normal glucose homeostasis. In some cases, the subject is in need of treatment. However, in some cases the subject is treated to reduce the incidence or onset of a disease or disorder.

Modulators of Glucose Metabolism

The compositions and methods of the present disclosure can include, in some embodiments, a modulator of glucose metabolism. Various modulators of glucose metabolism can be used, and include without limitation lipids, amino acids, small-molecule drugs, antibodies, proteins, nucleic acids, and gene editing systems. In some embodiments, the modulator of glucose metabolism inhibits glucose metabolism. For example, the modulator of glucose metabolism can be a glucose-uptake inhibitor. In some embodiments, the glucose-uptake inhibitor can be an inhibitor of a sodium-glucose transport protein. In some embodiments, the modulator of glucose metabolism can be an inhibitor of a glucose transporter. In some embodiments, the glucose-uptake inhibitor can be selected from the group consisting of a sodium-glucose-linked transport protein 1 (SGLT1) inhibitor, a sodium-glucose-linked transport protein 2 (SGLT2) inhibitor, or a dual SGLT1/SGLT2 inhibitor.

The modulator of glucose metabolism can, in some cases, be administered while the subject is consuming a ketogenic diet or while the subject is being administered a ketogenic diet.

Glucose is essential for energy production in the living body and the glucose transporter plays a critical role in various organs. Glucose transporters are classified into two families. Facilitative glucose transporters (GLUTs) transport glucose by facilitated diffusion. Sodium-glucose-linked transporters (SGLTs) co-transport sodium ion and glucose (or other substrates) using an electrochemical gradient across the membrane. (Harada et al. Role of sodium-glucose transporters in glucose uptake of the intestine and kidney. J Diabetes Investig. 2012 Aug. 20; 3(4): 352-353.; Gallo et al. Probing SGLT2 as a therapeutic target for diabetes: Basic physiology and consequences. Diab Vase Dis Res. 2015 March; 12(2): 78-89; Wright et al. Biology of Human Sodium Glucose Transporters. Physiological Reviews. 91(2):733-794 (2011).) The six SGLT protein and gene families are shown in Table 2. In certain embodiments, the modulator of glucose metabolism inhibits one or more SGLT protein.

TABLE 2

Sodium-dependent glucose transporter and tissue distribution

| Protein | Gene | Substrate | Tissue distribution |
|---------|--------|-----------|---------------------|
| SGLT1 | SLC5A1 | Glucose, galactose | Intestine, trachea, kidney, heart, brain, testis, prostate |
| SGLT2 | SLC5A2 | Glucose | Kidney, liver, thyroid, muscle, heart |
| SGLT3 | SLC5A4 | Glucose sensor | Intestine, testis, uterus, lung, brain, thyroid |
| SGLT4 | SLC5A9 | Mannose, glucose | Intestine, kidney, liver, brain, trachea, lung, uterus, pancreas |
| SGLT5 | SLC5A10 | Fructose, mannose, glucose, galactose | Kidney, cortex |
| SGLT6 | SLC5A11 | Chiro-inositol | Spinal cord, kidney, brain |

In some embodiments, the glucose-uptake inhibitor can be dapagliflozin, empagliflozin, canagliflozin, ipragliflozin, tofogliflozin, sergliflozin etabonate, remogliflozin etabonate, ertugliflozin, sotagliflozin, conagliflozin, or a combination thereof. In some embodiments, the modulator of glucose metabolism can be metformin. In some embodiments, the modulator of glucose metabolism can be an insulin receptor/IGF1 receptor inhibitor. In some embodiments, the modulator of glucose metabolism can be linsitinib (OSI-906).

Dapagliflozin (tradename Farxiga™ in the U.S. and Forxiga™ in the EU and Russia) is a drug of the gliflozin class, used to treat type-2 diabetes. It was developed by Bristol-Myers Squibb in partnership with AstraZeneca. Dapagliflozin has the following chemical structure:

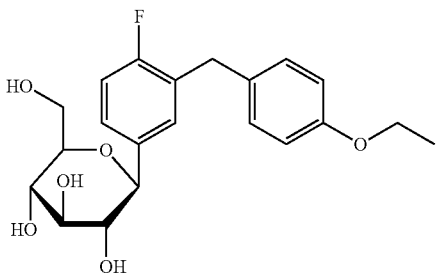

Empagliflozin (tradename Jardiance™) is a drug of the gliflozin class, approved for the treatment of type-2 diabetes in adults in 2014. It was developed by Boehringer Ingelheim and Eli Lilly and Company. Empagliflozin is an inhibitor of SGLT2 and causes sugar in the blood to be excreted by the kidneys and eliminated in urine. Empagliflozin has the following chemical structure:

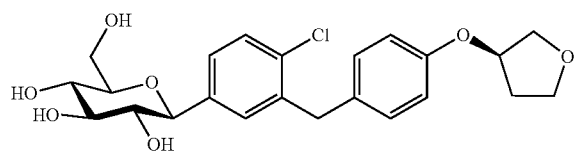

Canagliflozin (tradename Invokana™ or Sulisent™) is a medication used for the treatment of type-2 diabetes. It is of the gliflozin class or SGLT2 inhibitors class.

Canagliflozin has the following chemical structure:

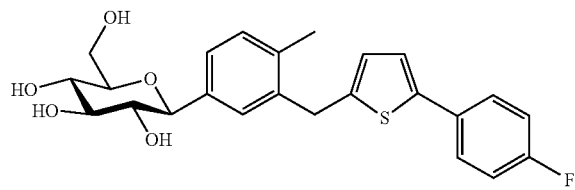

Ipragliflozin (tradenames Suglat™ and Jardiance™) is a pharmaceutical drug for treatment of type-2 diabetes. Ipragliflozin, jointly developed by Astellas Pharma and Kotobuki Pharmaceutical, was approved as an adjunct to diet and exercise to improve glycemic control in adults with type-2 diabetes mellitus. Ipragliflozin has the following chemical structure:

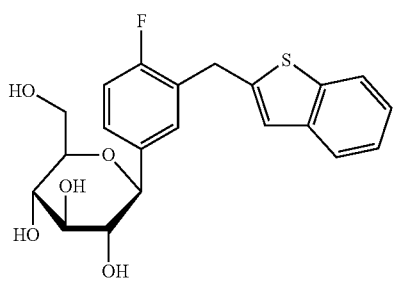

Tofogliflozin (codenamed CSG452) is an experimental drug for the treatment of diabetes mellitus and is being developed by Chugai Pharma in collaboration with Kowa and Sanofi. It is an inhibitor of SGLT2. Tofogliflozin has received its first global approval for this indication in Japan as either monotherapy or in combination with other antihyperglycemic agents. Tofogliflozin has the following chemical structure:

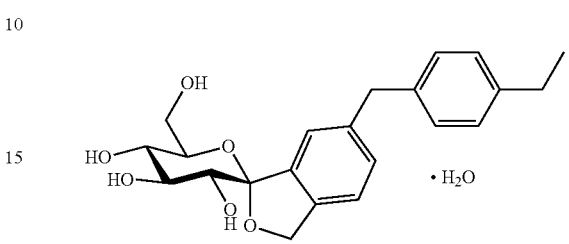

Sergliflozin etabonate (codenamed GW869682X) is an investigational antidiabetic drug being developed by GlaxoSmithKline. It is a SGLT2 inhibitor.

Sergliflozin etabonate has the following chemical structure:

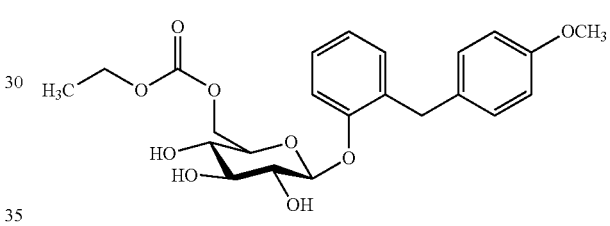

Remogliflozin etabonate is a proposed drug of the gliflozin class for the treatment of non-alcoholic steatohepatitis ("NASH") and type-2 diabetes.

Remogliflozin is being developed by Avolynt, Inc. Remogliflozin etabonate has the following chemical structure:

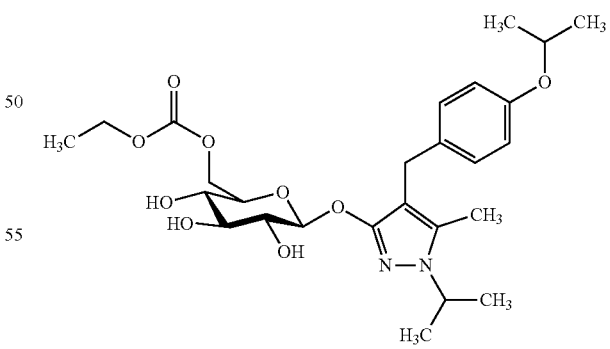

Ertugliflozin (tradename Steglatro™) is a drug for the treatment of type-2 diabetes. In the United States, it was approved by the Food and Drug Administration for use as a monotherapy and as a fixed dose combination with either sitagliptin or with metformin. Ertugliflozin has the following chemical structure:

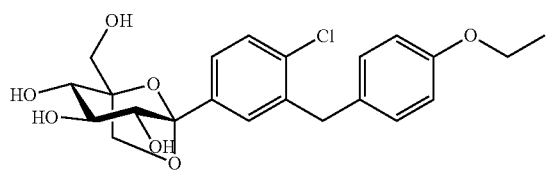 [SMILES: CCOc1ccc(Cc2cc([C@]34OCC(CO)(O3)[C@@H](O)[C@H](O)C4O)ccc2Cl)cc1]

Sotagliflozin, or LX4211, is an orally-delivered small molecule compound that is currently in development by Lexicon Pharmaceuticals for the treatment of type-1 and type-2 diabetes mellitus. Sotagliflozin inhibits SGLT1 and SGLT2. Sotagliflozin has the following chemical structure:

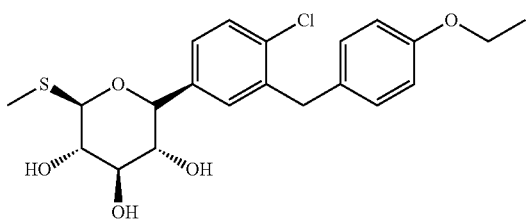

Canagliflozin (trade name Invokana or Sulisent) is a medication used for the treatment of type-2 diabetes. It is of the gliflozin class or SGLT2 inhibitor class. Canagliflozin has the following chemical structure:

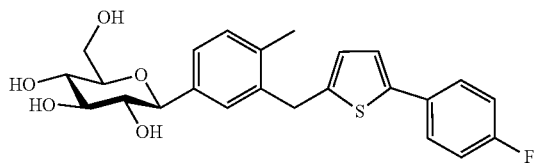

Metformin is a first-line medication for the treatment of type-2 diabetes, particularly in people who are overweight. Metformin has the following chemical structure:

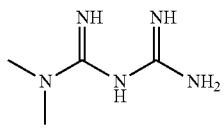

Linsitinib (codename OSI-906) is an experimental drug candidate for the treatment of various types of cancer. In some cases, it can act as a modulator of glucose metabolism, a pathway inhibitor, or both. It is an inhibitor of the insulin receptor and of the insulin-like growth factor 1 receptor (IGF-1R). (Fassnacht et al. Linsitinib (OSI-906) versus placebo for subjects with locally advanced or metastatic adrenocortical carcinoma: a double-blind, randomized, phase 3 study. *Lancet Oncology.* 16(4):426-435 (2015).) Linsitinib has the following chemical structure:

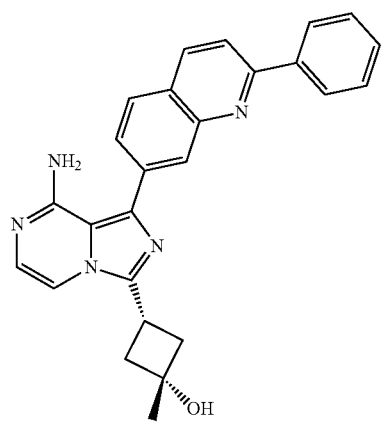 [SMILES: C[C@]1(O)C[C@@H](c2nc(-c3ccc4ccc(-c5ccccc5)nc4c3)c3c(N)nccn32)C1]

In some cases, a modulator of glucose metabolism can be administered concurrently with a pathway inhibitor of the insulin-receptor/PI3K/AKT/mTOR pathway. In some cases, a modulator of glucose metabolism can be administered before a pathway inhibitor of the insulin-receptor/PI3K/AKT/mTOR pathway. In some cases, a modulator of glucose metabolism can be administered after a pathway inhibitor of the insulin-receptor/PI3K/AKT/mTOR pathway is administered. A ketogenic diet can be consumed or administered before, during or after a modulator of glucose metabolism is administered.

Pathway Inhibitor

In some embodiments, the disclosure provides a method of treating a disease or disorder associated with PI3K signaling that includes administering to a subject an effective amount of a pathway inhibitor. In some embodiments, the disclosure provides a method of treating a disease or disorder associated with PI3K signaling that includes administering to a subject an effective amount of a pathway inhibitor, where the subject is on a ketogenic diet during treatment. The subject can be in need of such treatment or the subject can be treated to reduce the incidence or onset of a disease or disorder. In some embodiments, the pathway inhibitor is capable of inhibiting at least one kinase in the insulin-receptor/PI3K/AKT/mTOR pathway. In some embodiments, the pathway inhibitor is capable of inhibiting one or more targets such as any of INSR/IGFR, PI3K, AKT, mTOR, or a combination thereof. In some embodiments, the pathway inhibitor is capable of inhibiting a PI3K. In some embodiments, the pathway inhibitor is capable of inhibiting one or more of p110-α, p110-β, p110-γ, p110-δ, p85-α, p85-β, p55-γ, p150, p101, p87, PI3K-C2α, PI3K-C2β, PI3K-C2γ, and Vps34.

In some embodiments, the pathway inhibitor can be idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, apelisib, MK2206, linsitinib (OSI-906), or a combination thereof.

Idelalisib (tradename Zydelig™, codenamed GS-1101 or CAL-101) is a drug used for the treatment of certain hematological malignancies. The substance acts as a phosphoinositide 3-kinase inhibitor. More specifically, it blocks p110-δ, the delta isoform of the enzyme phosphoinositide 3-kinase (PI3K). It was developed by Gilead Sciences. Idelalisib has the following chemical structure:

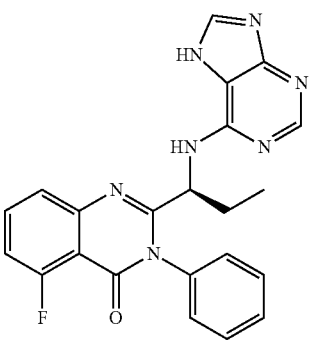 [SMILES: CC[C@H](Nc1ncnc2nc[nH]c12)c1nc2cccc(F)c2c(=O)n1-c1ccccc1]

Copanlisib (trade name Aligopa™, codenamed BAY 80-6946), is a kinase inhibitor developed by Bayer Health-Care Pharmaceuticals Inc. and approved for the treatment of adult subjects experiencing relapsed follicular lymphoma who have received at least two prior systemic therapies. Copanlisib has the following chemical structure:

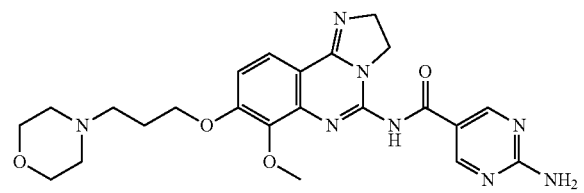 [SMILES: COc1c(OCCCN2CCOCC2)ccc2c1N=C(NC(=O)c1cnc(N)nc1)N1CCN=C21]

Buparlisib (codenamed BKM120) is an orally bioavailable specific oral inhibitor of the pan-class I phosphatidylinositol 3-kinase (PI3K) family of lipid kinases with potential antineoplastic activity. Buparlisib specifically inhibits class I PIK3 in an ATP-competitive manner, thereby inhibiting the production of the secondary messenger phosphatidylinositol-3,4,5-trisphosphate and activation of the PI3K signaling pathway. Buparlisib has the following chemical structure:

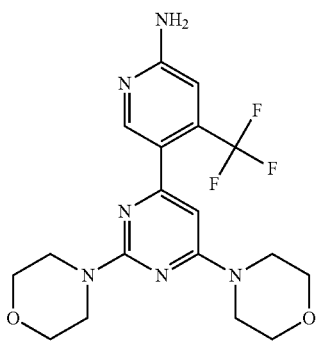 [SMILES: Nc1cc(C(F)(F)F)c(-c2cc(N3CCOCC3)nc(N3CCOCC3)n2)cn1]

Some studies indicate that administration of BKM120 alone can be associated with an unfavorable safety profile and minimal antitumor activity during advanced or recurrent endometrial carcinoma. However, the types of combination therapies described herein can reduce or eliminate such side effects. For example, BKM120 may be administered in lower doses when combined with the other therapeutic agents and/or a ketogenic diet. Such combination therapies can provide reduced toxicity and avoid side effects.

Alpelisib (codename BYL719) is an orally bioavailable phosphatidylinositol 3-kinase (PI3K) inhibitor with potential antineoplastic activity. Alpelisib specifically inhibits PIK3, thereby inhibiting the activation of the PI3K signaling pathway.

Alpelisib has the following chemical structure:

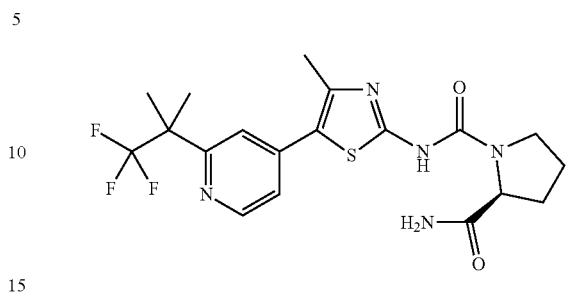

Taselisib (codename GDC-0032), developed by Roche, is an orally bioavailable inhibitor of the class I phosphatidylinositol 3-kinase (PI3K) alpha isoform (PIK3CA), with potential antineoplastic activity. Taselisib selectively inhibits PIK3CA and its mutant forms, which may result in tumor cell apoptosis and growth inhibition in PIK3CA-expressing tumor cells. Taselisib has the following chemical structure:

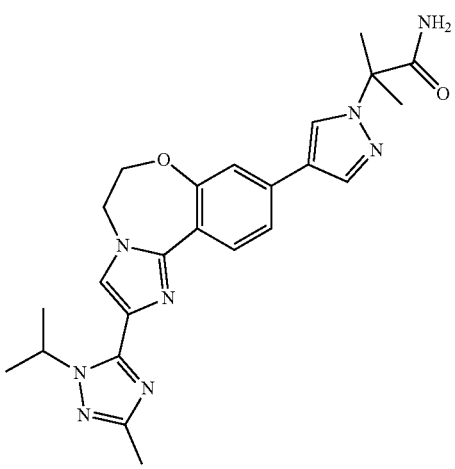 [SMILES: Cc1nc(-c2cn3c(n2)-c2ccc(-c4cnn(C(C)(C)C(N)=O)c4)cc2OCC3)n(C(C)C)n1]

Pictilisib (codename GDC-0941), developed by Roche, is a potent inhibitor of PI3Kα/δ with IC50 of 3 nM in cell-free assays, with modest selectivity against p110β (11-fold) and p110γ (25-fold). Pictilisib has the following chemical structure:

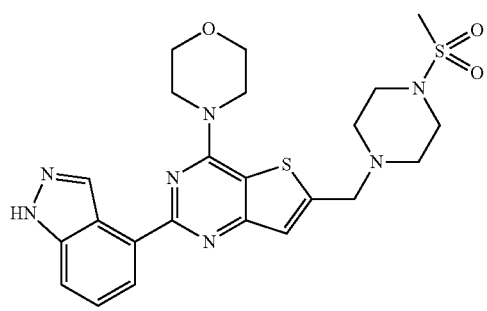 [SMILES: CS(=O)(=O)N1CCN(Cc2cc3nc(-c4cccc5[nH]ncc45)nc(N4CCOCC4)c3s2)CC1]

Apitolisib (codename GDC-0980, RG7422) is a potent, class I PI3K inhibitor for PI3Kα/β/δ/γ with $IC_{50}$ of 5 nM/27 nM/7 nM/14 nM in cell-free assays, respectively. Apitolisib is also an mTOR inhibitor with Ki of 17 nM in a cell-free assay. Apitolisib has the following chemical structure:

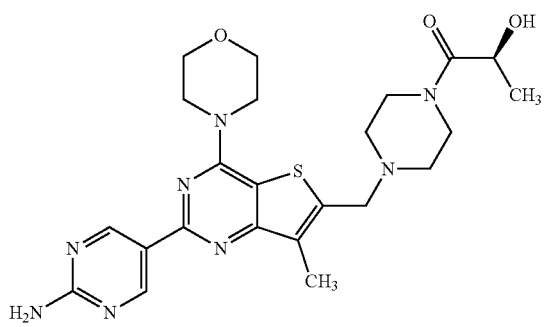 [SMILES: Cc1c(CN2CCN(C(=O)[C@H](C)O)CC2)sc2c(N3CCOCC3)nc(-c3cnc(N)nc3)nc12]

Serabelisib (also known as MLN1117, INK1117, and TAK-117) is an orally bioavailable inhibitor of the class I phosphoinositide 3-kinase (PI3K) alpha isoform. Serabelisib selectively inhibits PI3K alpha kinase, including mutations of PIK3CA, in the PI3K/Akt/mTOR pathway. Serabelisib has the following structure:

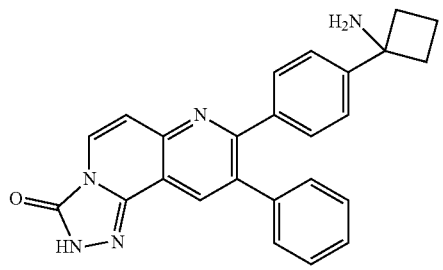

Linsitinib (codename OSI-906) is an experimental drug candidate for the treatment of various types of cancer. In some cases, it can act as a modulator of glucose metabolism, a pathway inhibitor, or both. It is an inhibitor of the insulin receptor and of the insulin-like growth factor 1 receptor (IGF-1R). (Fassnacht et al. Linsitinib (OSI-906) versus placebo for subjects with locally advanced or metastatic adrenocortical carcinoma: a double-blind, randomized, phase 3 study. *Lancet Oncology.* 16(4):426-435 (2015).) Linsitinib has the following chemical structure:

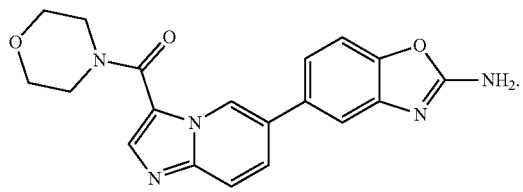 [SMILES: Nc1nc2cc(-c3ccc4ncc(C(=O)N5CCOCC5)n4c3)ccc2o1]

Dactolisib (codenamed NVP-BEZ235 and BEZ-235) is an imidazoquinoline derivative acting as a PI3K inhibitor. Dactolisib also inhibits mTOR. Dactolisib has the following chemical structure:

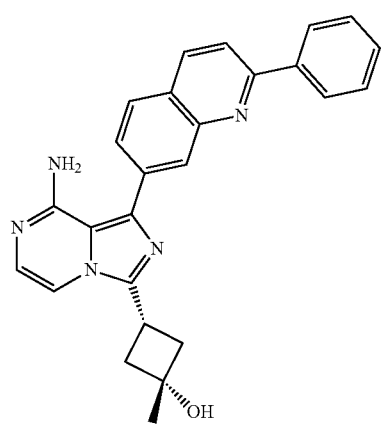

In some cases, combinations of inhibitors of at least one kinase in the insulin-receptor/PI3K/AKT/mTOR pathway can be used or administered to a subject. For example, the inhibitor of at least one kinase in the insulin-receptor/PI3K/AKT/mTOR pathway can be a combination of two or more of buparlisib (BKM120), taselisib (GDC-0032), pictilisib (GDC-0941), or linsitinib (OSI-906).

In particular embodiments of methods that comprise the use of both a pathway inhibitor and a modulator of glucose metabolism, and compositions that comprise both a pathway inhibitor and a modulator of glucose metabolism, a combination comprising any of the combinations of agent shown in any row of Table 6 may be used.

TABLE 6

Combinations of modulators of glucose metabolism and pathway inhibitors

| Modulator of glucose metabolism | Pathway inhibitor |
| --- | --- |
| dapagliflozin | idelalisib |
| dapagliflozin | copanlisib |
| dapagliflozin | buparlisib (BKM120) |
| dapagliflozin | alpelisib (BYL719) |

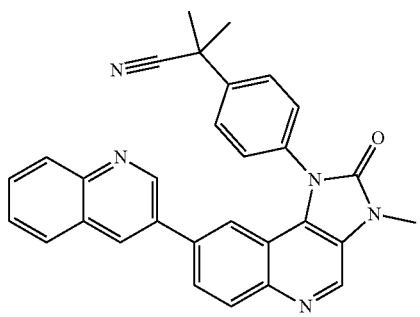 [SMILES: Cn1c(=O)n(-c2ccc(C(C)(C)C#N)cc2)c2c3cc(-c4cnc5ccccc5c4)ccc3ncc21]

MK2206 is an orally bioavailable allosteric inhibitor of the serine/threonine protein kinase Akt (protein kinase B) with potential antineoplastic activity. MK2206 binds to and inhibits the activity of Akt in a non-ATP competitive manner. MK2206 has the following chemical structure:

TABLE 6-continued

Combinations of modulators of glucose metabolism and pathway inhibitors

| Modulator of glucose metabolism | Pathway inhibitor |
| --- | --- |
| dapagliflozin | taselisib (GDC-0032) |
| dapagliflozin | pictilisib (GDC-0941) |
| dapagliflozin | apitolisib (GDC-0980) |
| dapagliflozin | dactolisib |
| dapagliflozin | apelisib |
| dapagliflozin | MK2206 |
| dapagliflozin | linsitinib (OSI-906) |
| empagliflozin | idelalisib |
| empagliflozin | copanlisib |
| empagliflozin | buparlisib (BKM120) |
| empagliflozin | alpelisib (BYL719) |
| empagliflozin | taselisib (GDC-0032) |
| empagliflozin | pictilisib (GDC-0941) |
| empagliflozin | apitolisib (GDC-0980) |
| empagliflozin | dactolisib |
| empagliflozin | apelisib |
| empagliflozin | MK2206 |
| empagliflozin | linsitinib (OSI-906) |
| canagliflozin | idelalisib |
| canagliflozin | copanlisib |
| canagliflozin | buparlisib (BKM120) |
| canagliflozin | alpelisib (BYL719) |
| canagliflozin | taselisib (GDC-0032) |
| canagliflozin | pictilisib (GDC-0941) |
| canagliflozin | apitolisib (GDC-0980) |
| canagliflozin | dactolisib |
| canagliflozin | apelisib |
| canagliflozin | MK2206 |
| canagliflozin | linsitinib (OSI-906) |
| ipragliflozin | idelalisib |
| ipragliflozin | copanlisib |
| ipragliflozin | buparlisib (BKM120) |
| ipragliflozin | alpelisib (BYL719) |
| ipragliflozin | taselisib (GDC-0032) |
| ipragliflozin | pictilisib (GDC-0941) |
| ipragliflozin | apitolisib (GDC-0980) |
| ipragliflozin | dactolisib |
| ipragliflozin | apelisib |
| ipragliflozin | MK2206 |
| ipragliflozin | linsitinib (OSI-906) |
| tofogliflozin | idelalisib |
| tofogliflozin | copanlisib |
| tofogliflozin | buparlisib (BKM120) |
| tofogliflozin | alpelisib (BYL719) |
| tofogliflozin | taselisib (GDC-0032) |
| tofogliflozin | pictilisib (GDC-0941) |
| tofogliflozin | apitolisib (GDC-0980) |
| tofogliflozin | dactolisib |
| tofogliflozin | apelisib |
| tofogliflozin | MK2206 |
| tofogliflozin | linsitinib (OSI-906) |
| sergliflozin etabonate | idelalisib |
| sergliflozin etabonate | copanlisib |
| sergliflozin etabonate | buparlisib (BKM120) |
| sergliflozin etabonate | alpelisib (BYL719) |
| sergliflozin etabonate | taselisib (GDC-0032) |
| sergliflozin etabonate | pictilisib (GDC-0941) |
| sergliflozin etabonate | apitolisib (GDC-0980) |
| sergliflozin etabonate | dactolisib |
| sergliflozin etabonate | apelisib |
| sergliflozin etabonate | MK2206 |
| sergliflozin etabonate | linsitinib (OSI-906) |
| remogliflozin etabonate | idelalisib |
| remogliflozin etabonate | copanlisib |
| remogliflozin etabonate | buparlisib (BKM120) |
| remogliflozin etabonate | alpelisib (BYL719) |
| remogliflozin etabonate | taselisib (GDC-0032) |
| remogliflozin etabonate | pictilisib (GDC-0941) |
| remogliflozin etabonate | apitolisib (GDC-0980) |
| remogliflozin etabonate | dactolisib |
| remogliflozin etabonate | apelisib |
| remogliflozin etabonate | MK2206 |
| remogliflozin etabonate | linsitinib (OSI-906) |
| ertugliflozin | idelalisib |
| ertugliflozin | copanlisib |
| ertugliflozin | buparlisib (BKM120) |
| ertugliflozin | alpelisib (BYL719) |
| ertugliflozin | taselisib (GDC-0032) |
| ertugliflozin | pictilisib (GDC-0941) |
| ertugliflozin | apitolisib (GDC-0980) |
| ertugliflozin | dactolisib |
| ertugliflozin | apelisib |
| ertugliflozin | MK2206 |
| ertugliflozin | linsitinib (OSI-906) |
| sotagliflozin | idelalisib |
| sotagliflozin | copanlisib |
| sotagliflozin | buparlisib (BKM120) |
| sotagliflozin | alpelisib (BYL719) |
| sotagliflozin | taselisib (GDC-0032) |
| sotagliflozin | pictilisib (GDC-0941) |
| sotagliflozin | apitolisib (GDC-0980) |
| sotagliflozin | dactolisib |
| sotagliflozin | apelisib |
| sotagliflozin | MK2206 |
| sotagliflozin | linsitinib (OSI-906) |
| conagliflozin | idelalisib |
| conagliflozin | copanlisib |
| conagliflozin | buparlisib (BKM120) |
| conagliflozin | alpelisib (BYL719) |
| conagliflozin | taselisib (GDC-0032) |
| conagliflozin | pictilisib (GDC-0941) |
| conagliflozin | apitolisib (GDC-0980) |
| conagliflozin | dactolisib |
| conagliflozin | apelisib |
| conagliflozin | MK2206 |
| conagliflozin | linsitinib (OSI-906) |
| metformin | idelalisib |
| metformin | copanlisib |
| metformin | buparlisib (BKM120) |
| metformin | alpelisib (BYL719) |
| metformin | taselisib (GDC-0032) |
| metformin | pictilisib (GDC-0941) |
| metformin | apitolisib (GDC-0980) |
| metformin | dactolisib |
| metformin | apelisib |
| metformin | MK2206 |
| metformin | linsitinib (OSI-906) |
| linsitinib | idelalisib |
| linsitinib | copanlisib |
| linsitinib | buparlisib (BKM120) |
| linsitinib | alpelisib (BYL719) |
| linsitinib | taselisib (GDC-0032) |
| linsitinib | pictilisib (GDC-0941) |
| linsitinib | apitolisib (GDC-0980) |
| linsitinib | dactolisib |
| linsitinib | apelisib |
| linsitinib | MK2206 |

In some cases, a pathway inhibitor of the insulin-receptor/PI3K/AKT/mTOR pathway can be administered concurrently with a modulator of glucose metabolism. In some cases, a pathway inhibitor of the insulin-receptor/PI3K/AKT/mTOR pathway can be administered before a modulator of glucose metabolism. In some cases, a pathway inhibitor of the insulin-receptor/PI3K/AKT/mTOR pathway can be administered after a modulator of glucose metabolism. A ketogenic diet can be consumed or administered before, during or after a pathway inhibitor of the insulin-receptor/PI3K/AKT/mTOR pathway is administered.

Ketogenic Diet

In some embodiments, the disclosure provides a method of treating a disease or disorder associated with PI3K signaling where the subject consumes a ketogenic diet during treatment. In some embodiments, the method includes administering a ketogenic diet to the subject.

In some cases, the subject can be administered a pathway inhibitor of the insulin-receptor/PI3K/AKT/mTOR pathway while consuming or being administered a ketogenic diet. In some embodiments, the method can include administering an effective amount of a modulator of glucose metabolism to the subject while administering the ketogenic diet and/or while administering a pathway inhibitor of the insulin-receptor/PI3K/AKT/mTOR pathway.

In some embodiments, the subject consumes a ketogenic diet prior to administration of the pathway inhibitor. In some embodiments, the subject consumes a ketogenic diet after administration of the pathway inhibitor. In some embodiments, the subject consumes a ketogenic diet concurrently with administration of the pathway inhibitor.

Ketogenic diets have been used in epileptic subjects since the 1970s and have been shown to reduce blood glucose levels and increase insulin sensitivity as compared to normal western diets. (Hopkins, B. D., Goncalves, M. D. & Cantley, L. C. Obesity and Cancer Mechanisms: Cancer Metabolism. *J Clin Oncol* 34, 4277-4283, doi:10.1200/JCO.2016.67.9712 (2016); Sampaio, L. P. Ketogenic diet for epilepsy treatment. *Arq Neuropsiquiatr* 74, 842-848, doi: 10.1590/0004-282X20160116 (2016).) In some embodiments, ketogenic diet includes a high-fat, low-carbohydrate diet. In some embodiments, the ketogenic diet is stricter than the modified Atkins diet. In some embodiments, the ketogenic diet includes consuming defined amounts of calories, fluids, and proteins. A ketogenic diet is available at most major hospitals.

A classic ketogenic diet is defined by a set ratio of grams of fat to grams of carbohydrate plus protein. The most common ratio is 3:1 or 4:1 grams of fat to grams of carbohydrate plus protein. In this classic ketogenic diet approximately 90% of the energy comes from fat and 10% from carbohydrate and protein combined. Calories are typically restricted to 80-90% of the daily recommendations for age. In some cases, fluid restriction is imposed on the subject consuming the diet.

A ketogenic diet useful for experimental purposes is, in one example, AIN-76A purified rat and mouse diet, available from ThermoFischer®, or an equivalent thereof.

In some embodiments, the ketogenic diet includes at most 5%, 6%, 7%, 8%, 9%, 10%, 11%, 12%, 13%, 14%, or 15% protein, with the remainder of the diet made up of fat, fiber, ash, and carbohydrates. In some embodiments, the ketogenic diet includes at most 2%, 3%, 4%, 5%, 6%, 7%, 8%, 9%, or 10% carbohydrates, with the remainder of the diet made up of fat, fiber, ash, and protein. In some embodiments, the ketogenic diet includes fat measured in grams and carbohydrates and proteins collectively measured in grams in a ratio of 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, or 4.5 to one (1) of fat to carbohydrate/protein. A comparison of a ketogenic diet with a normal diet is shown below as Table 3. Although the ketogenic diet shown in Table 3 was used for experimental purposes, the ketogenic diet administered or consumed by a subject pursuant to one or more of the methods described herein can have similar percentages of fat, protein, carbohydrate, ash, and the other components listed in Table 3.

In some cases, such a ketogenic diet can involve ingestion of a 3:1 ratio of ketogenic-to-antiketogenic macromolecules, which results in approximately 85% fat, 12% protein, and 3% carbohydrates. There can be a diverse mixture of fats. For example, the fats can include those from plants, nuts, and animal products. The diet can be actively managed by dieticians who interact with patients on the diet on a specific time table, for example, on a weekly basis or on a monthly basis. Such a diet can obtain up to 80% compliance, up to 90% compliance, up to 95% compliance, up to 96% compliance, up to 98% compliance, up to 99% compliance, or even up to 100% compliance. For example, 100% compliance over 4 weeks was achieved in an ongoing pilot study in women with endometrial cancer.

Routes of Administration, Formulations, and Dosages

The disclosed methods of treatment can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, the compositions can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a pathway inhibitor (and/or a modulator of glucose metabolism) and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the pathway inhibitor and/or modulator of glucose metabolism is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed pharmaceutical compositions can be also formulated as a suppository that can be prepared from fatty emulsions or suspensions; using polyalkylene glycols such as propylene glycol, as the carrier.

The disclosed pharmaceutical compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the pathway inhibitor and/or modulator of glucose metabolism, as described in U.S. Pat. No. 5,262,564 which is hereby incorporated by reference in its entirety.

Disclosed pharmaceutical compositions can also be delivered by the use of monoclonal antibodies as individual carriers to which pathway inhibitor and/or modulator of glucose metabolism are coupled. Pathway inhibitor and/or modulator of glucose metabolism can also be coupled with soluble polymers as targetable drug carriers. Such polymers can include polyvinylpyrrolidone, pyran copolymer, poly (hydroxypropyl)methacrylamide-phenol, poly(hydroxyethyl)-aspanamide phenol, or poly(ethyleneoxide)-polylysine substituted with palmitoyl residues. Furthermore, pathway inhibitor and/or modulator of glucose metabolism can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, pathway inhibitor and/or modulator of glucose metabolism are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Pharmaceutical compositions can be prepared according to conventional mixing, granulating or coating methods, respectively, and the present pharmaceutical compositions can contain from about 0.1% to about 99%, from about 5% to about 90%, or from about 1% to about 20% of modulators of glucose metabolism and/or kinase inhibitor by weight or volume.

The dosage regimen is selected in accordance with a variety of factors including type, species, age, weight, sex and medical condition of the subject; the severity of the condition to be treated; the route of administration; the renal or hepatic function of the subject; and the particular compound employed. A physician or veterinarian of ordinary skill in the art can readily determine and prescribe the effective amount of the drug required to prevent, counter or arrest the progress of the disease or disorder.

In some cases, effective dosage amounts of pathway inhibitor and/or modulator of glucose metabolism, when used for the indicated effects, range from about 0.5 mg to about 5000 mg of the pathway inhibitor and/or modulator of glucose metabolism as needed to treat the disease or disorder. Compositions for in vivo or in vitro use can contain about 0.5, 5, 20, 50, 75, 100, 150, 250, 500, 750, 1000, 1250, 2500, 3500, or 5000 mg of the pathway inhibitor and/or modulator of glucose metabolism, or, in a range of from one amount to another amount in the list of doses. In one embodiment, the compositions are in the form of a tablet that can be scored.

In some embodiments, the disclosure provides a pharmaceutical composition that includes a modulator of glucose metabolism and an inhibitor of at least one kinase in the insulin-receptor/PI3K/AKT/mTOR pathway.

In some embodiments, the disclosure provides a pharmaceutical composition that includes a glucose-uptake inhibitor and an inhibitor of at least one kinase in the insulin-receptor/PI3K/AKT/mTOR pathway.

In some embodiments, the disclosure provides a kit comprising a pharmaceutical composition comprising a glucose-uptake inhibitor and a pharmaceutical composition comprising an inhibitor of at least one kinase in the insulin-receptor/PI3K/AKT/mTOR pathway.

Kits

Also described herein is a kit that includes a packaged pharmaceutical composition for controlling, preventing or treating a cell proliferative disease. The kits of the invention can be designed for controlling, preventing or treating cell proliferation or a cell proliferative disease.

In one embodiment, the kit or container holds at least one inhibitor of at least one kinase in the insulin-receptor/PI3K/AKT/mTOR pathway. The kit can also include a modulator of glucose metabolism. Each inhibitor or modulator can be packaged separately. Alternatively, one or more inhibitors or modulators can be packaged or formulated together.

Hence, the kit or container can hold at least one inhibitor of at least one kinase in the insulin-receptor/PI3K/AKT/mTOR pathway, at least one modulator of glucose metabolism, or a combination thereof.

The kit can also hold instructions for administering the at least one inhibitor of at least one kinase in the insulin-receptor/PI3K/AKT/mTOR pathway, the at least one modulator of glucose metabolism, or a combination thereof.

In another embodiment, the kit holds one or more components of a ketogenic diet. Each component of a ketogenic diet can be packaged separately. Alternatively, one or more components of a ketogenic diet can be packaged together.

In another embodiment, the kit or container holds instructions for starting and/or maintaining a ketogenic diet with instructions for using the at least one inhibitor of at least one kinase in the insulin-receptor/PI3K/AKT/mTOR pathway, at least one modulator of glucose metabolism, or a combination thereof. For example, the instructions can include methods for mixing components of a ketogenic diet, methods for obtaining supplemental components of a ketogenic diet, time tables for consumption of components of the ketogenic diet, or a combination thereof.

The kits of the invention can also include containers with tools useful for administering the compositions and maintaining a ketogenic diet as described herein. Such tools include syringes, swabs, catheters, antiseptic solutions, package opening devices, forks, spoons, straws, and the like.

The compositions, kits, and/or methods described herein are useful for treatment of cell proliferative diseases such as cancer or cell-proliferative disorder, a metabolic disorder, neurodegenerative disease, or an inflammatory disease. For example, the compositions, kits, and/or methods described herein can reduce the incidence or progression of such diseases by 1% or more, 2% or more, 3% or more, 5% or more, 7% or more, 10% or more, 15% or more, 20% or more, 25% or more, 30% or more, 40% or more, or 50% or more compared to a control. Such a control can be the initial frequency or previous rate of progression of the disease of the subject. The control can also be an average frequency or rate of progression of the disease. For example, when treating cancer, the compositions and/or methods described herein can reduce tumor volume in the treated subject by 1% or more, 2% or more, 3% or more, 5% or more, 7% or more, 10% or more, 15% or more, 20% or more, 25% or more, 30% or more, 40% or more, or 50% or more compared to a control. Such a control can be the initial tumor volume. In some cases, the compositions and/or methods described herein can reduce the incidence or progression of such diseases by at least 2-fold, or at least 3-fold, or at least 5-fold, or at least 10-fold compared to a control.

EXAMPLES

The following Examples are given for the purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art. Appendix A provides further description of experimental work involved in the development of the methods and compositions described herein.

Overview

Gain of function mutations in PIK3CA, encoding the insulin-activated phosphoinositide-3-kinase (PI3K), and loss of function mutations in PTEN, a phosphatase that degrades the phosphoinositide lipids generated by PI3K, are among the most frequent events in human cancers. Yet, pharmacological inhibition of PI3K, using diverse classes of inhibitors, has resulted in variable clinical responses in humans, raising the possibility of an inherent mechanism of resistance to PI3K inhibition. Here, the inventors show that pharmacologic blockade of PI3K not only elevates serum glucose but also dramatically raises serum insulin. This hyperinsulinemia re-activates the PI3K and mTOR signaling pathway in tumors within an hour or two of dosing, thereby compromising the effectiveness of blocking PI3K. The inventors demonstrate herein a variety of interventions to reduce serum insulin including metformin, a $Na^+$/Glucose co-transporter inhibitor, and a ketogenic diet. The inventors found that a diverse group of human tumor organoids and cell lines grown as tumors in mice, as well as genetically engineered mouse tumors, exhibited enhanced responses to PI3K inhibitors when the mice were on a ketogenic diet. The enhanced responses were found in tumors with or without PIK3CA mutations. These results demonstrate that maintaining patients on ketogenic diets or administering modulators of glucose metabolism (for example, therapies that lower serum insulin) could enhance patient responses to PI3K inhibitors across a wide spectrum of cancers.

The PI3K pathway is one of the most frequently mutated pathways in human cancer, with mutations in PIK3CA being observed at similar frequency to mutations in KRAS. More than twenty PI3K inhibitors have entered clinical trials but only two (idelalisib and copanlisib) have been approved for use in cancer therapy. These agents are effective for treating lymphomas by primarily targeting the PIK3CD encoded enzyme p110Δ rather than the more broadly mutated PIK3CA-encoded enzyme, p110α. Several drugs that target p110α have entered approval trials, however the toxicity profile, including hyperglycemia, has been a challenge to manage and the responses have not correlated with PIK3CA mutations as would be expected. Since p110α mediates virtually all cellular responses to insulin, hyperglycemia is an expected on-target effect of p110α inhibitors. Blocking insulin signaling promotes glucose release from the liver and prevents glucose uptake into skeletal muscle and fat. The resulting acute hyperglycemia varies from patient to patient and is often resolved within a few hours of drug administration due to compensatory insulin release from the pancreas. Many patients with borderline insulin resistance must discontinue therapy due to the inability to endogenously control serum glucose levels with glucose lowering drugs such as metformin during therapy. Experimental subjects subjected to prolonged PI3K inhibition display reduced glucose tolerance and increased insulin resistance.

Here, the inventors show that the systemic glucose-insulin feedback caused by targeted inhibition of this pathway activates PI3K signaling in several tumors, even in the presence of PI3K inhibitors. The feedback hyperinsulinemia disclosed herein can be prevented using dietary or pharmaceutical approaches, which greatly enhances the efficacy/toxicity ratios of insulin receptor/PI3K/AKT/mTOR pathway inhibitors. These findings have direct clinical implications for the multiple p110α inhibitors that are in clinical trials and provide a means to significantly increase treatment efficacy for patients with a myriad of tumor types.

Example 1: Disruption of Systemic Glucose Homeostasis Using Therapeutic Doses of Compounds Targeting a Variety of Kinases in the Insulin Receptor/PI3K/mTOR Pathway Hyperglycemia has largely been treated as a treatment-related complication that requires management in only a subset of patients for whom the hyperglycemia becomes persistent. Due to the body's normal glycemic regulation, patients treated with these agents experience some degree of systemic hyperinsulinemia as the pancreas attempts to normalize serum glucose levels. Since insulin is a potent stimulator of PI3K signaling in tumors and can have profound effects on cancer progression, the inventors hypothesized that treatment-induced hyperinsulinemia limits the therapeutic potential of agents targeting the PI3K pathway.

Figure 1B:
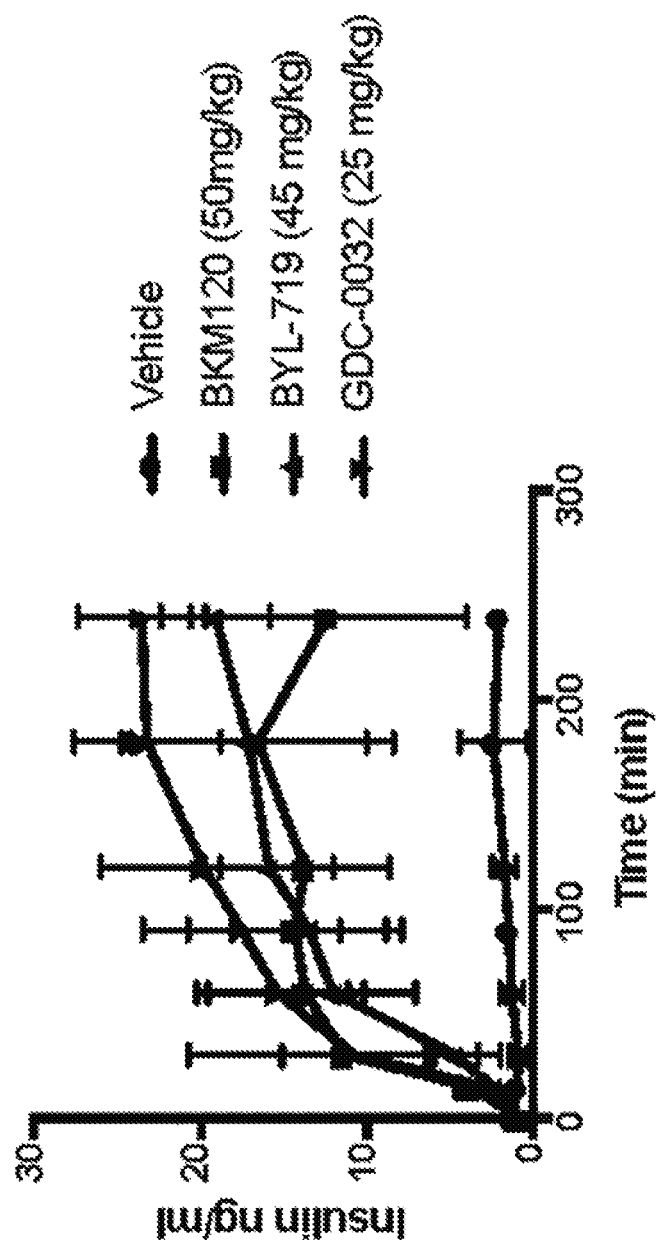
Figure 1C:
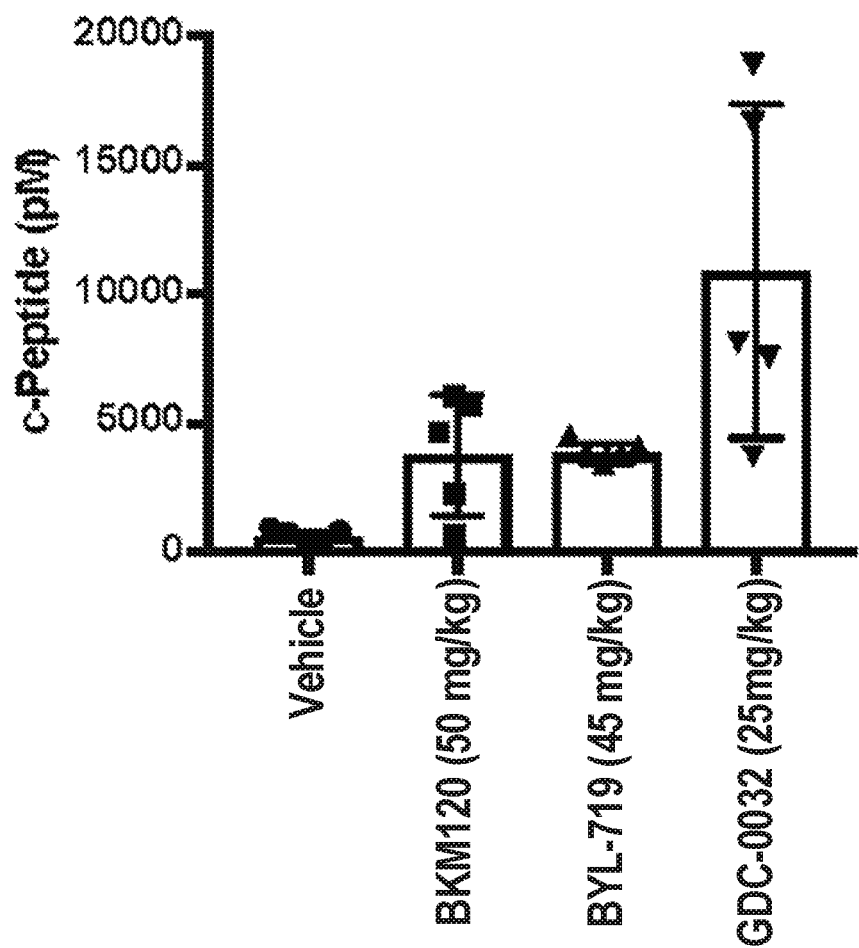
Figure 5A:
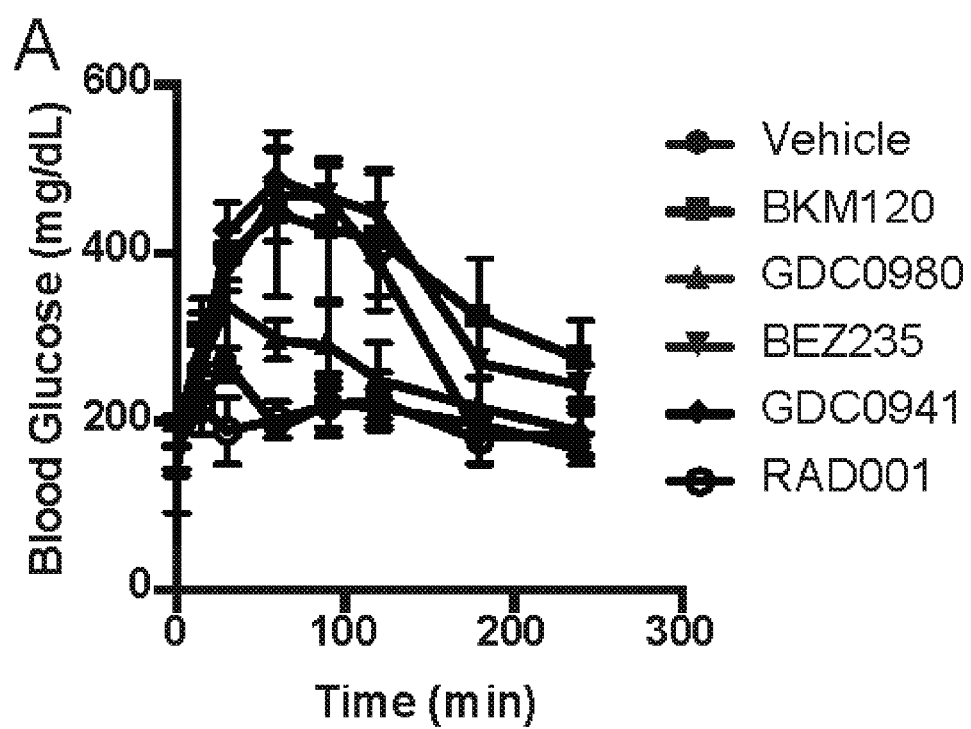
FIG. 5A-5D illustrate blood Glucose and C-Peptide levels after treatment with agents that target PI3K pathway.
Figure 5B:
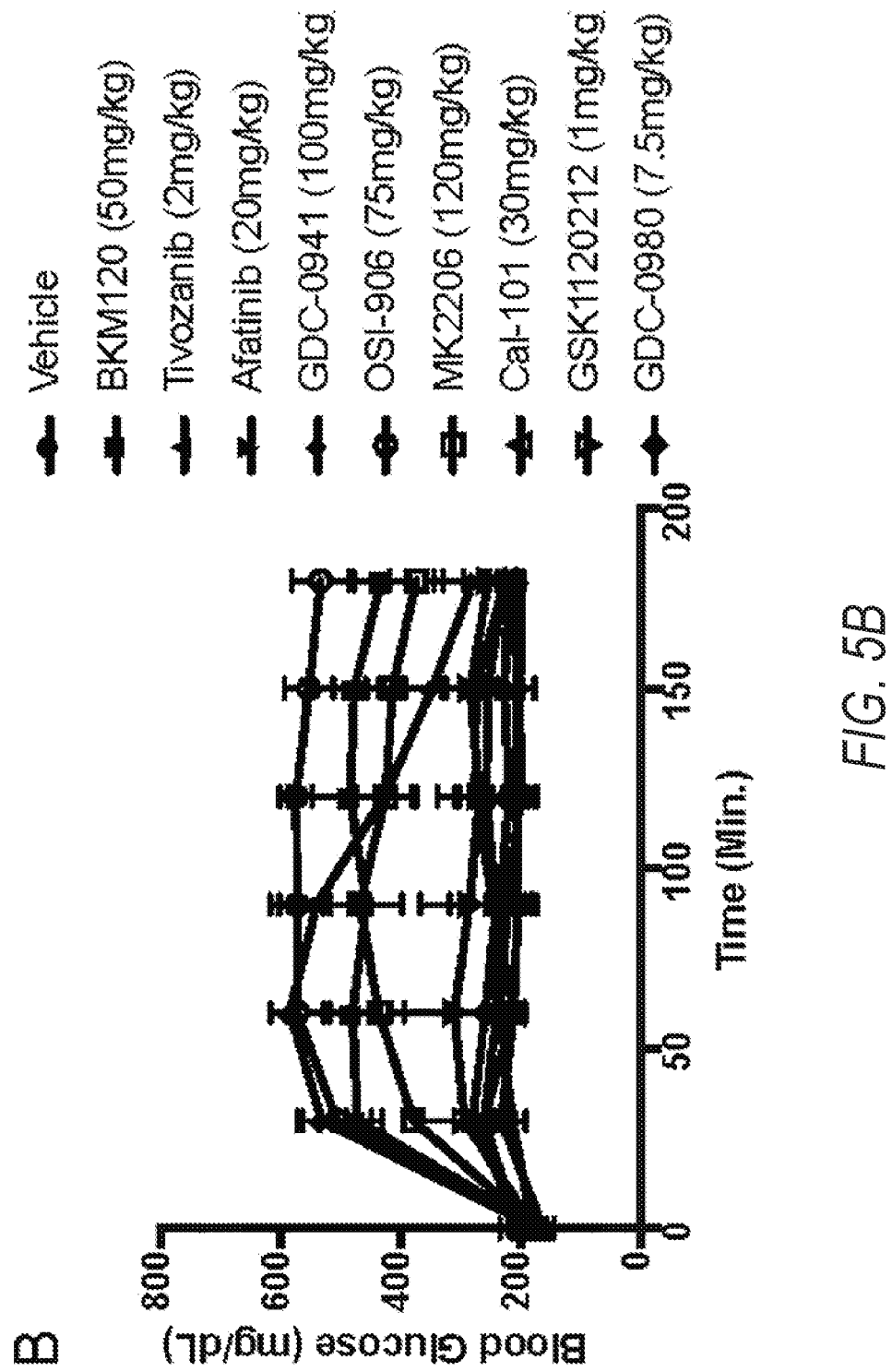
Figure 5C:
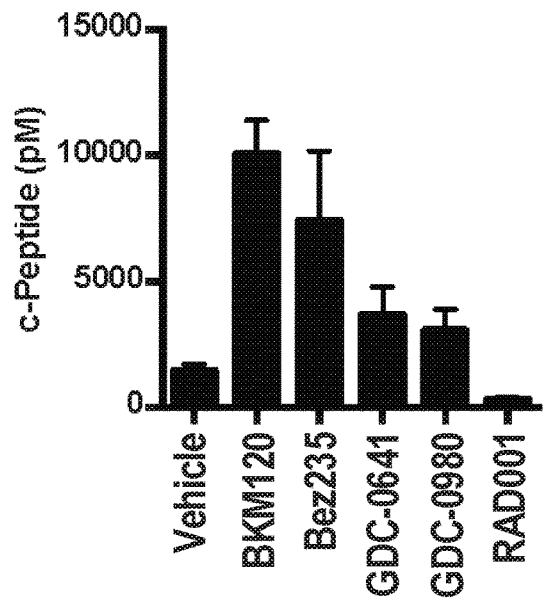
Figure 5D:
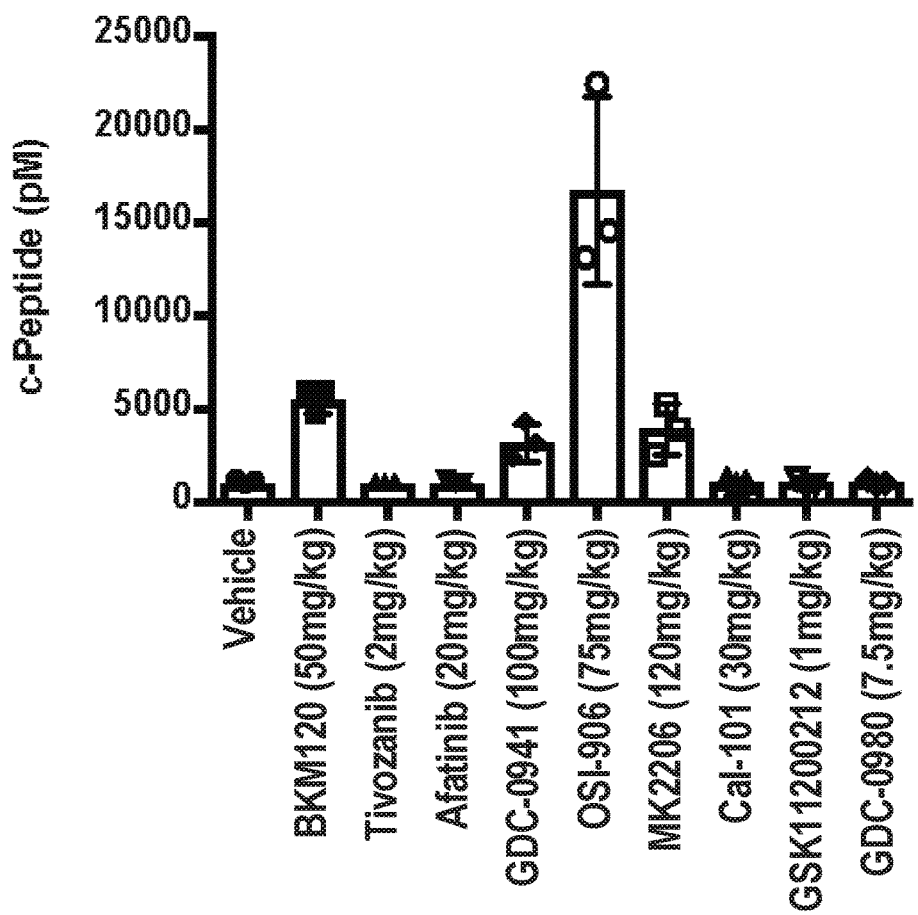
Figures 1, 6A:
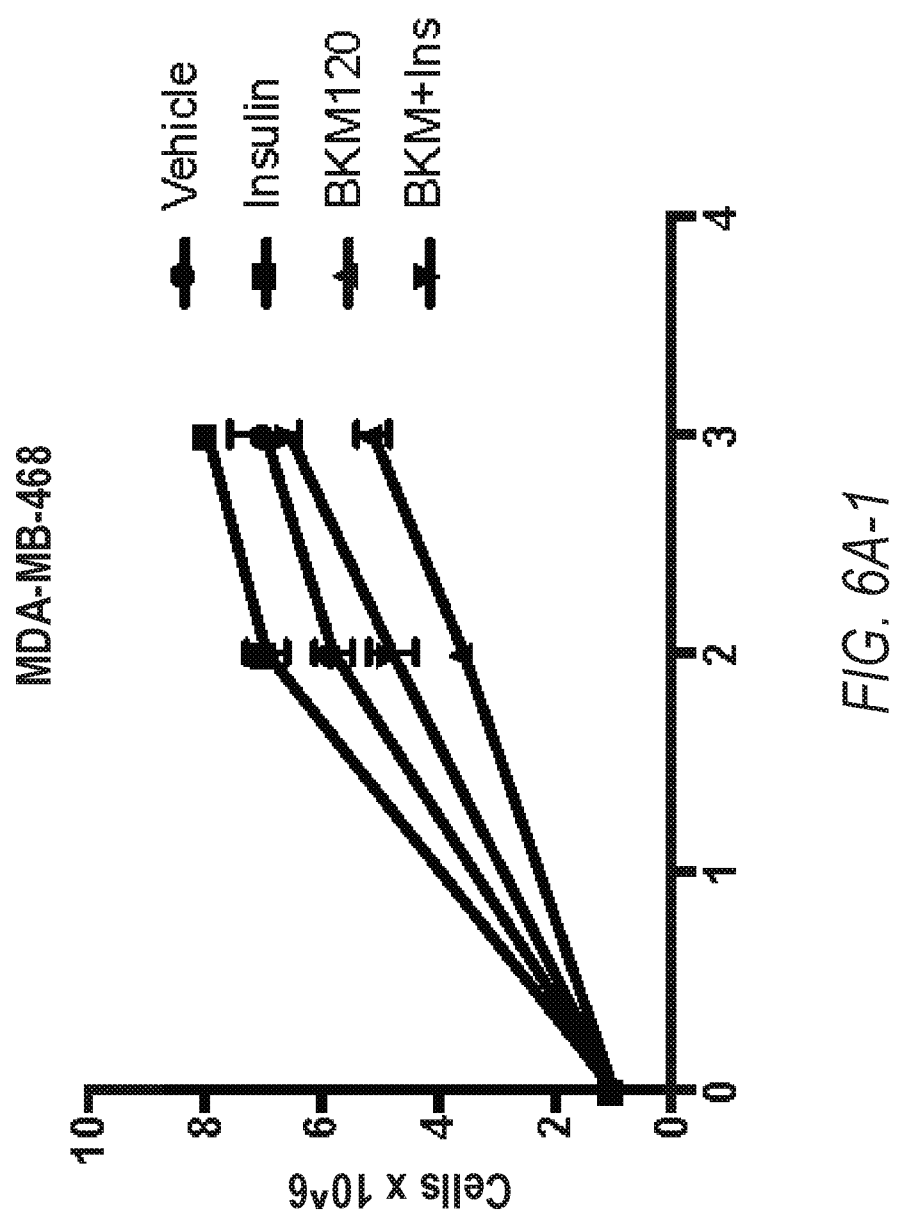
Figures 2, 6A:
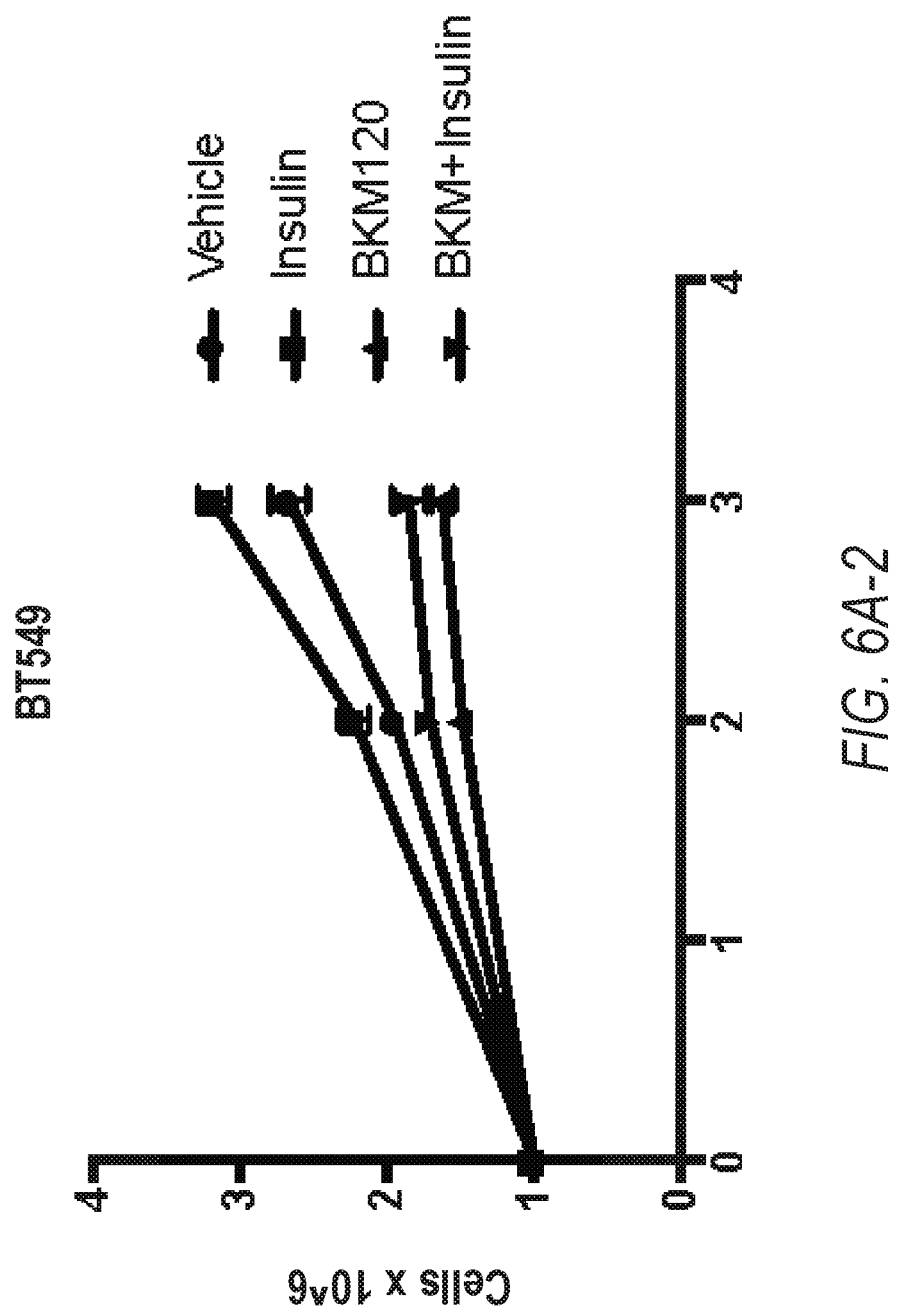
Figures 3, 6A:
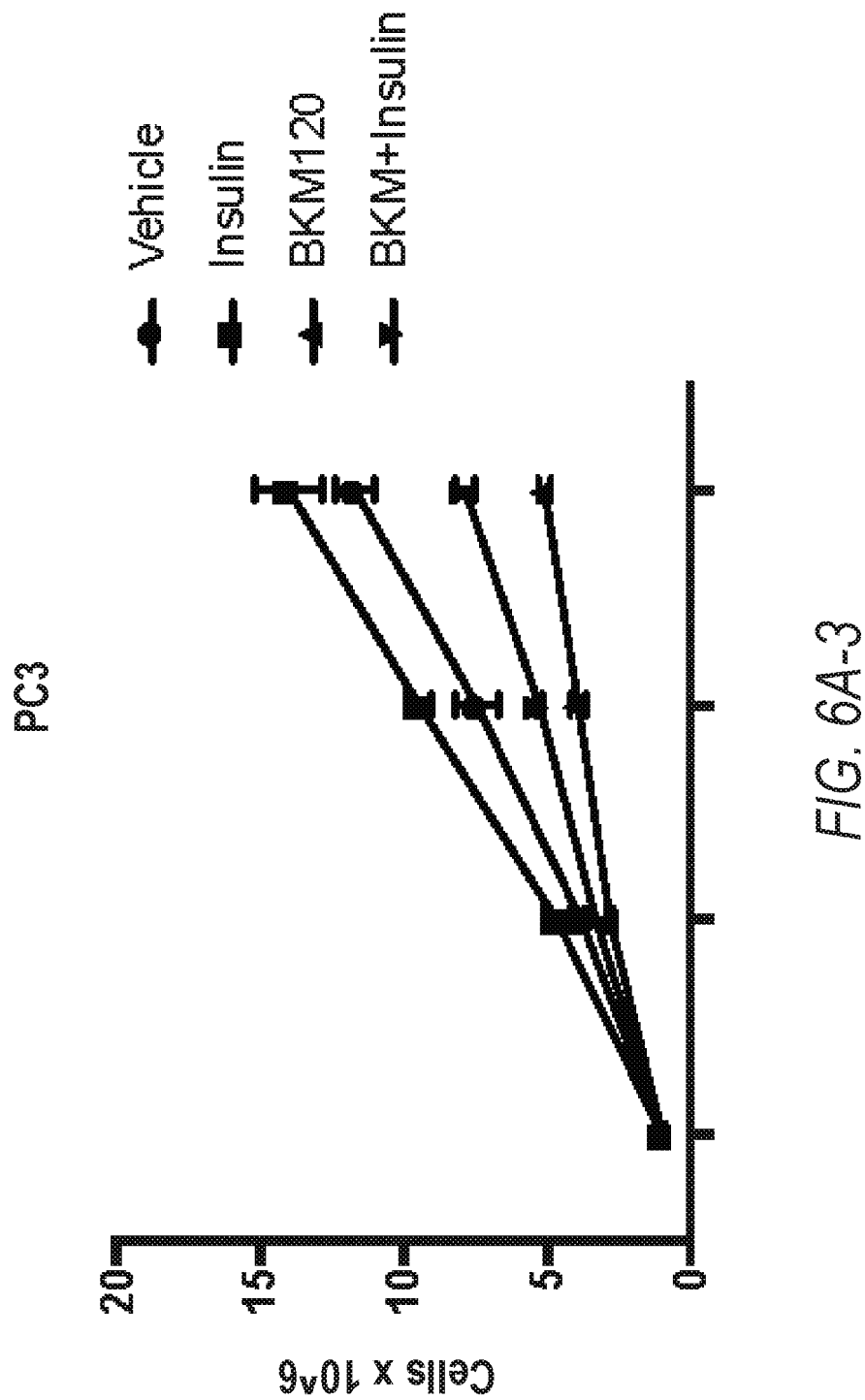
Figure 6B:
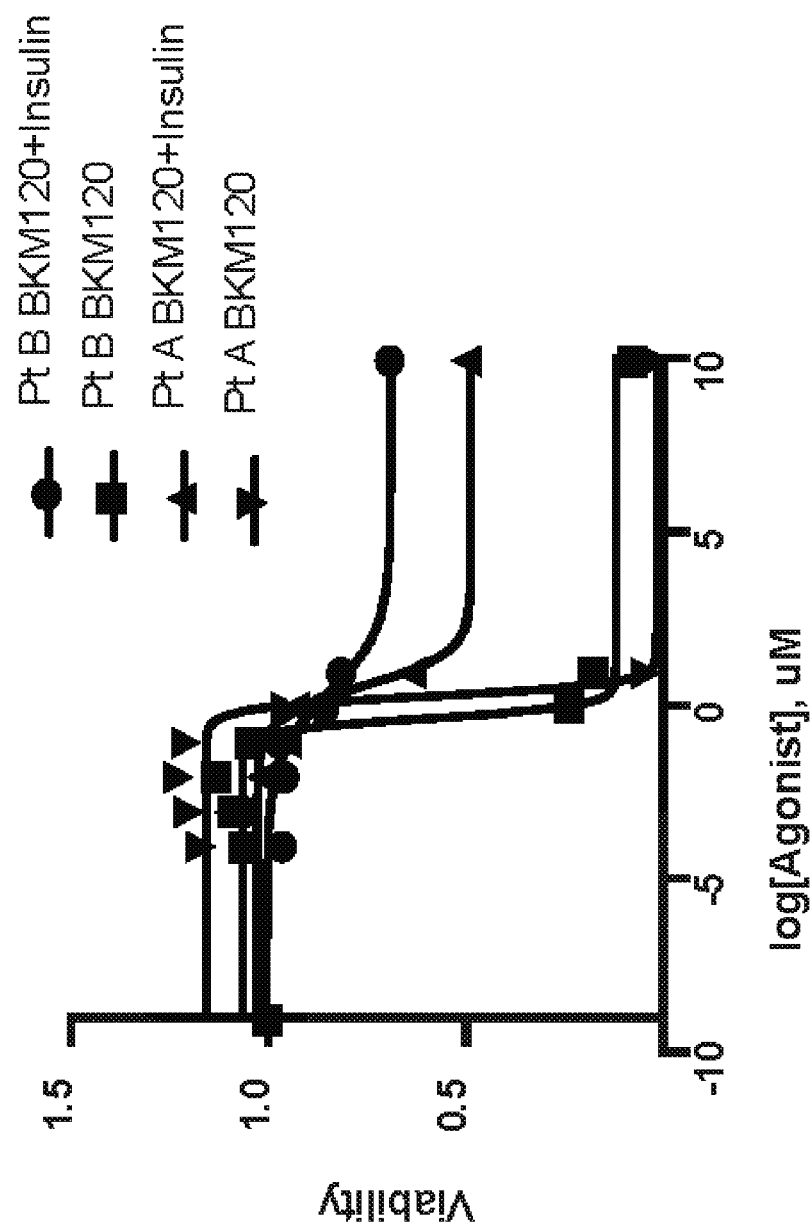
Figure 6C:
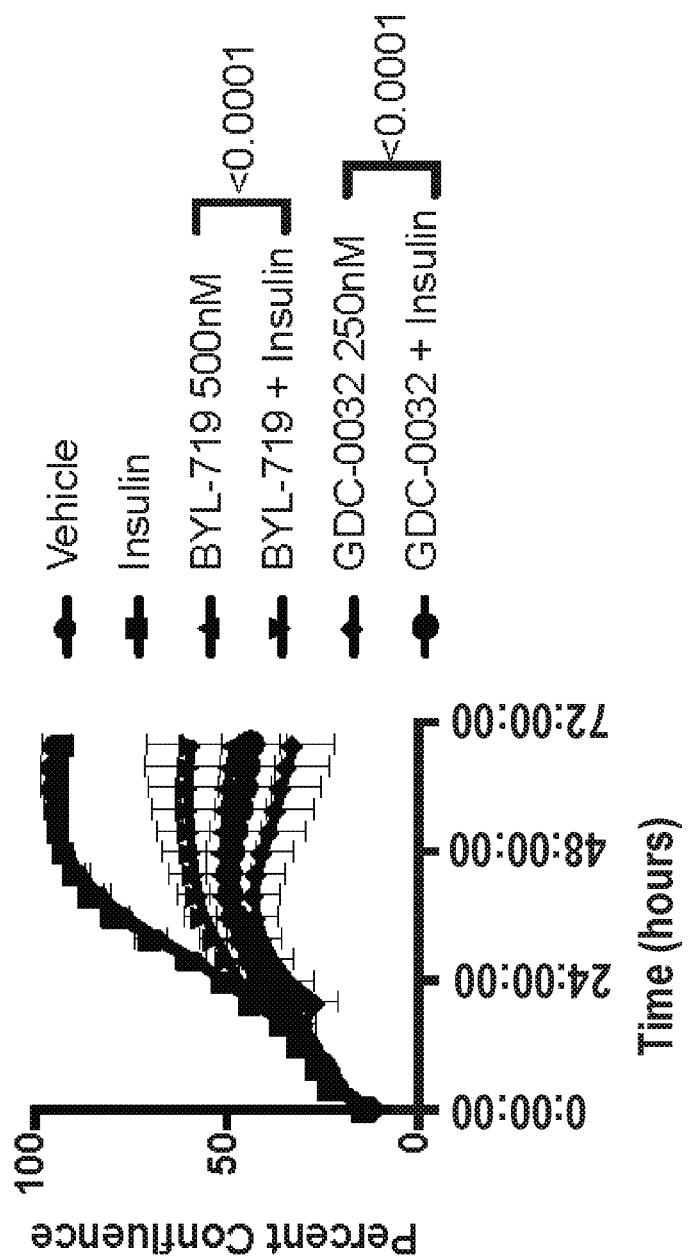
Figure 6D:
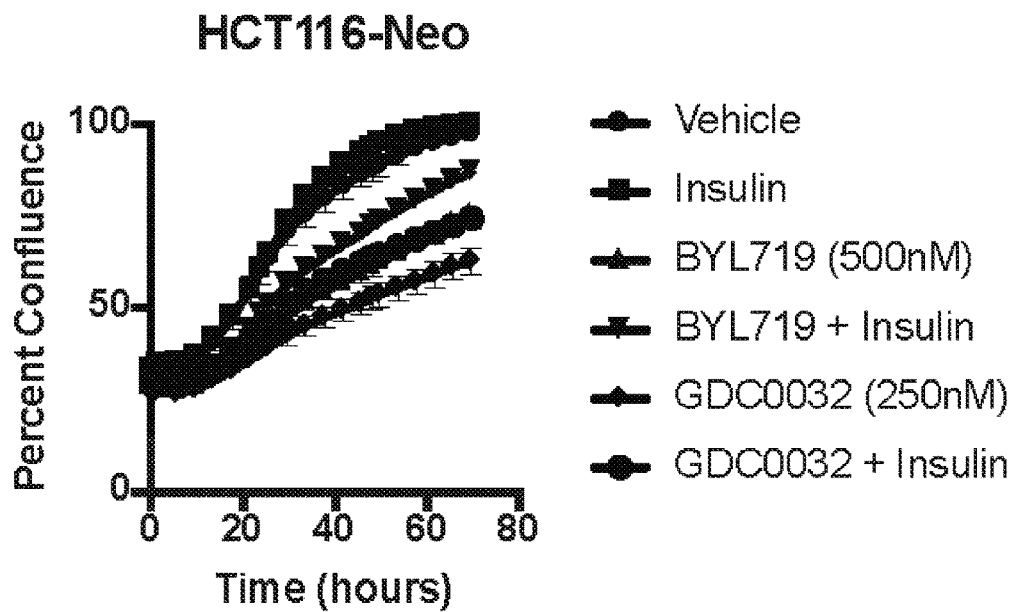
Figure 6E:
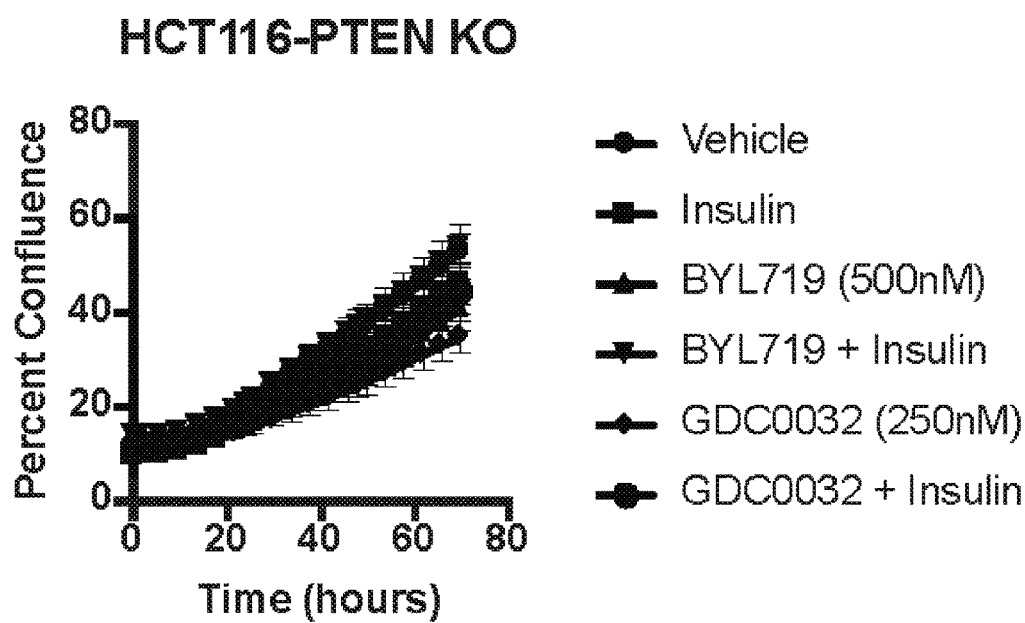
Figure 6F:
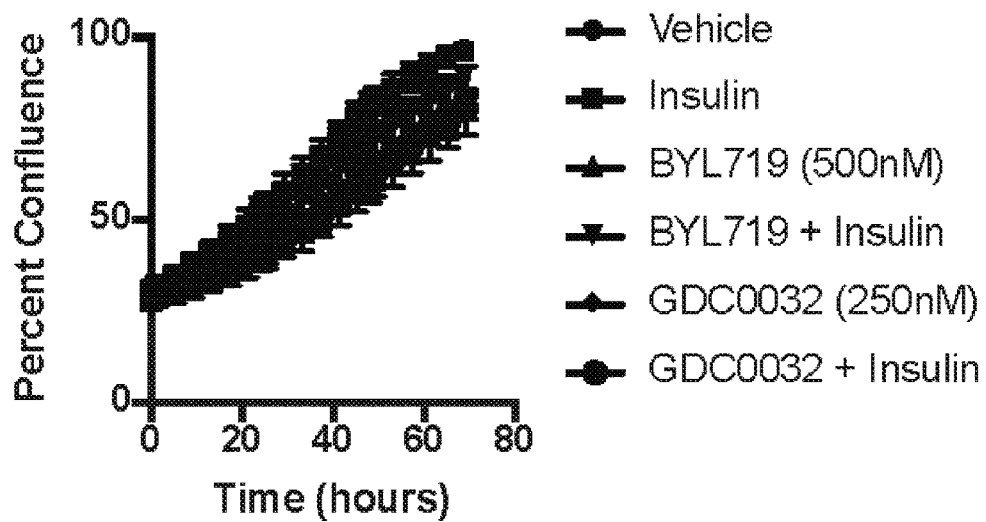
Figure 6G:
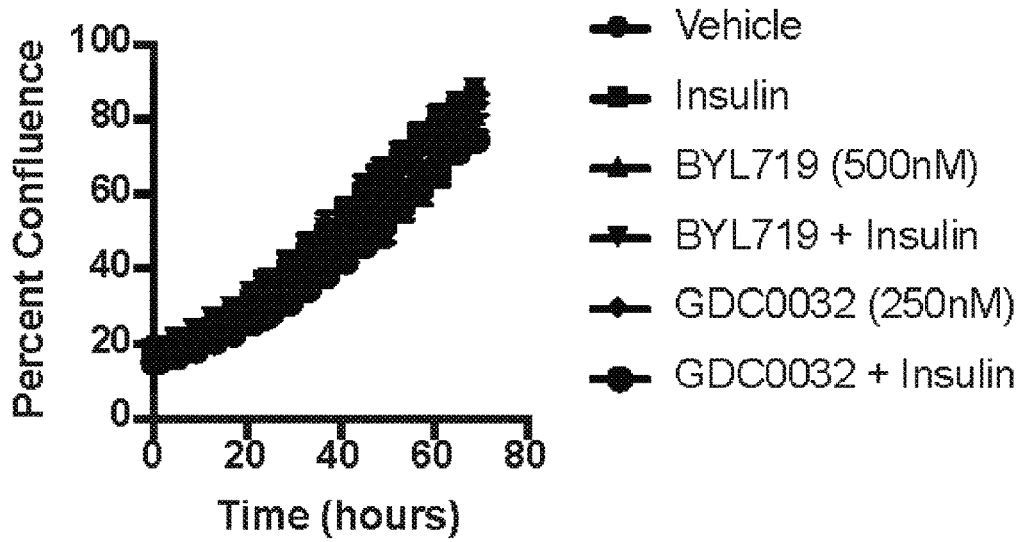
Figure 7A:
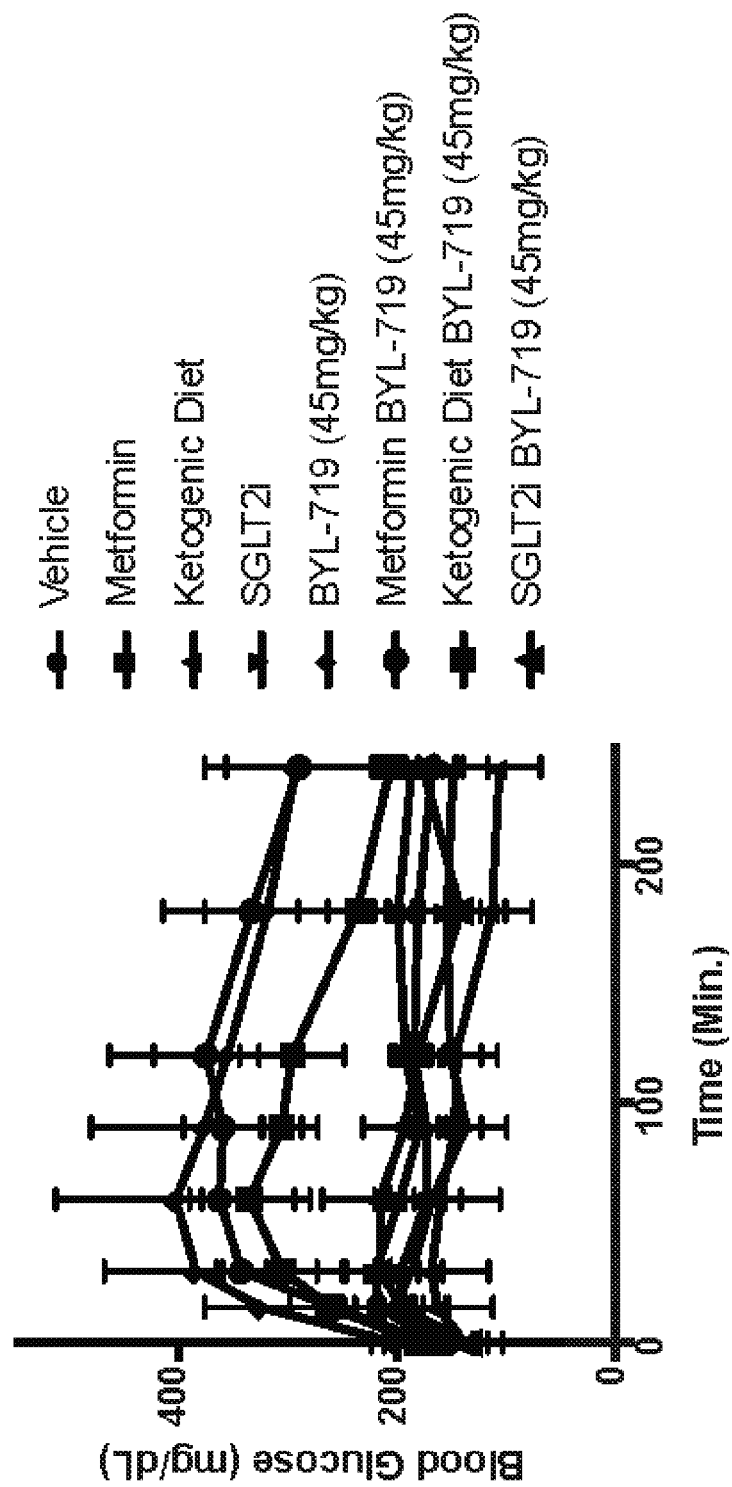
FIG. 7A-7F illustrates blood glucose, tumor volume, ketone concentration, and triglyceride levels for KPC K8484 allografts treated with PI3K inhibitors with or without supplemental approaches to target systemic insulin feedback.
Figure 7B:
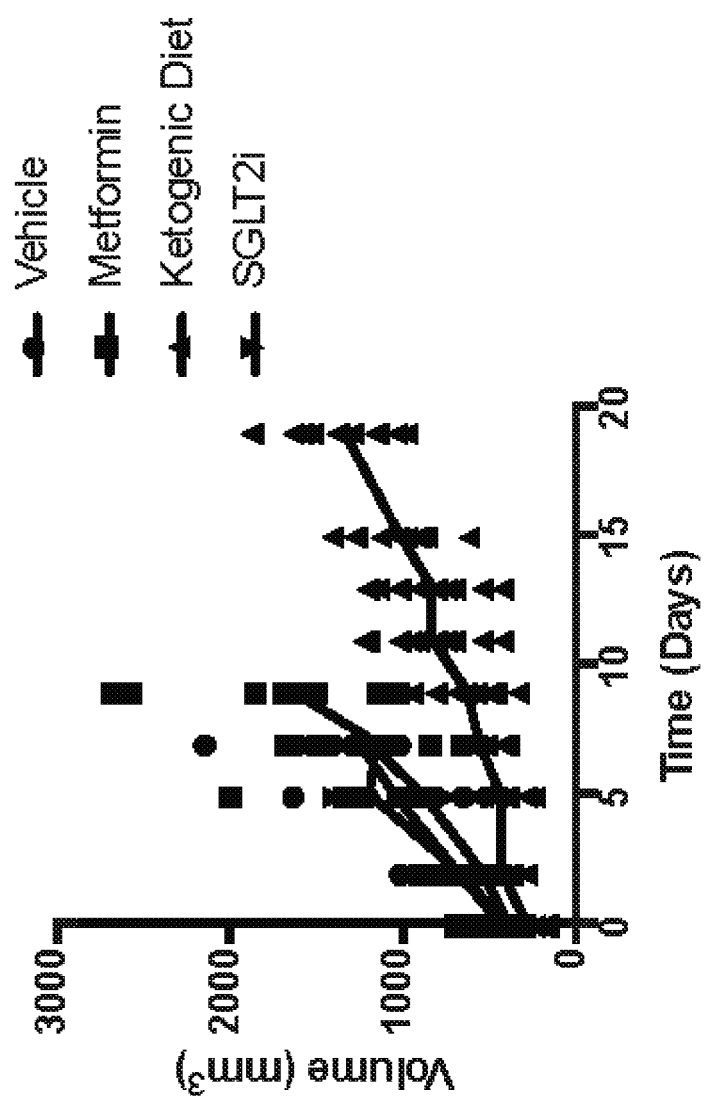
Figure 7C:
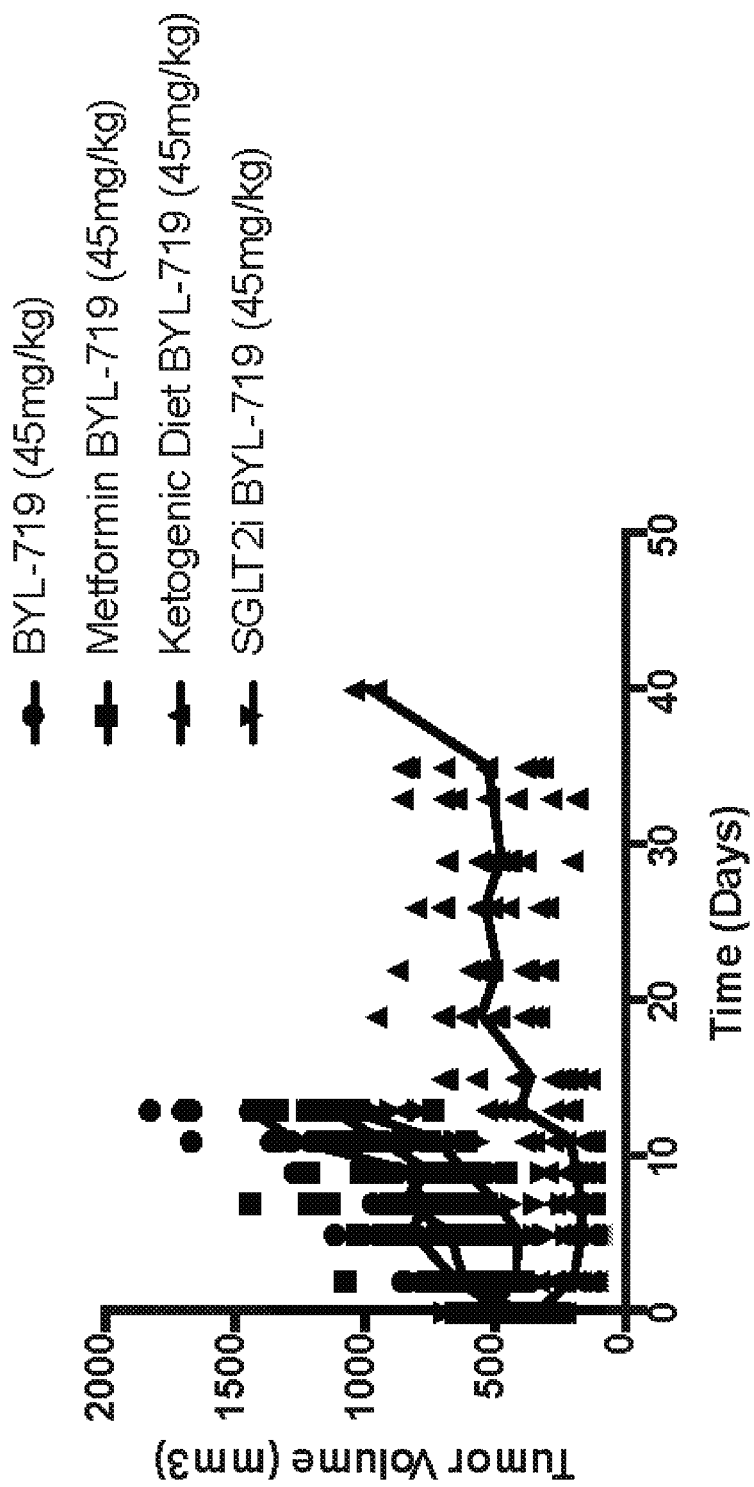
Figure 7D:
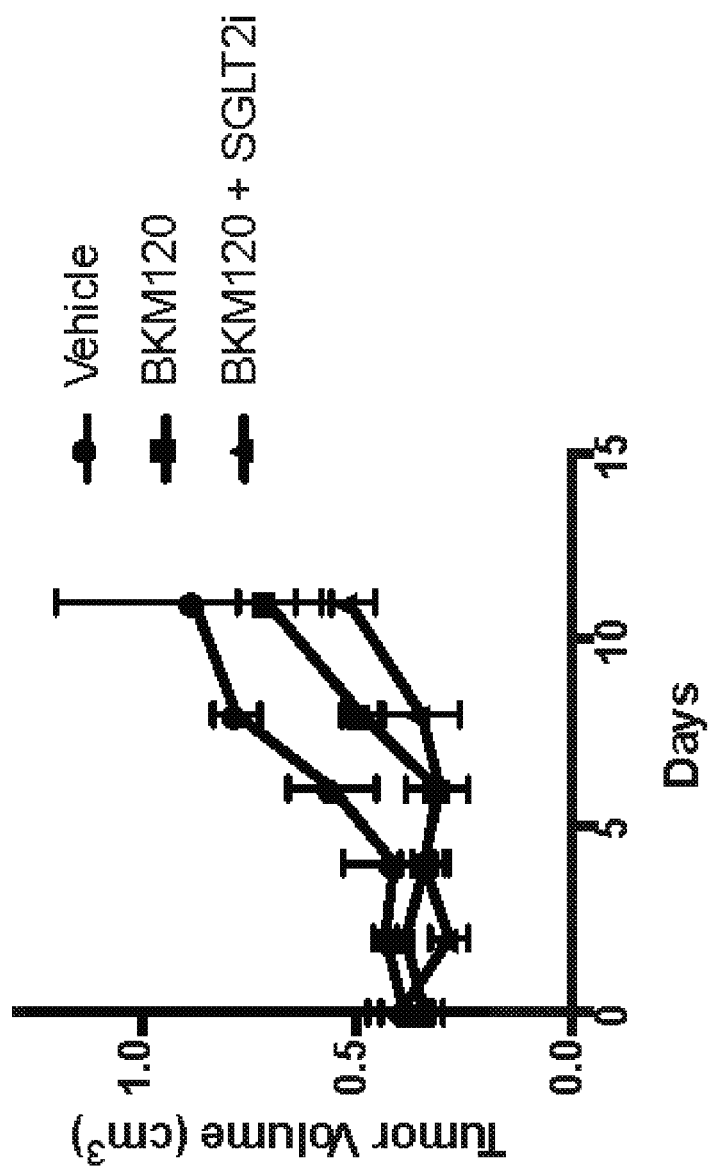
Figure 7E:
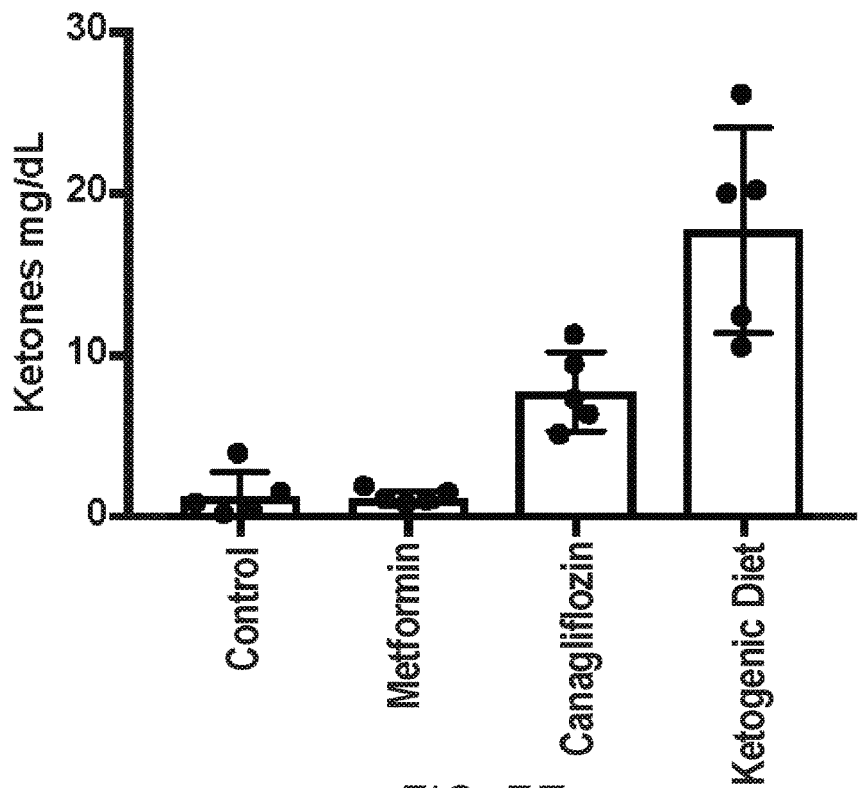
Figure 7F:
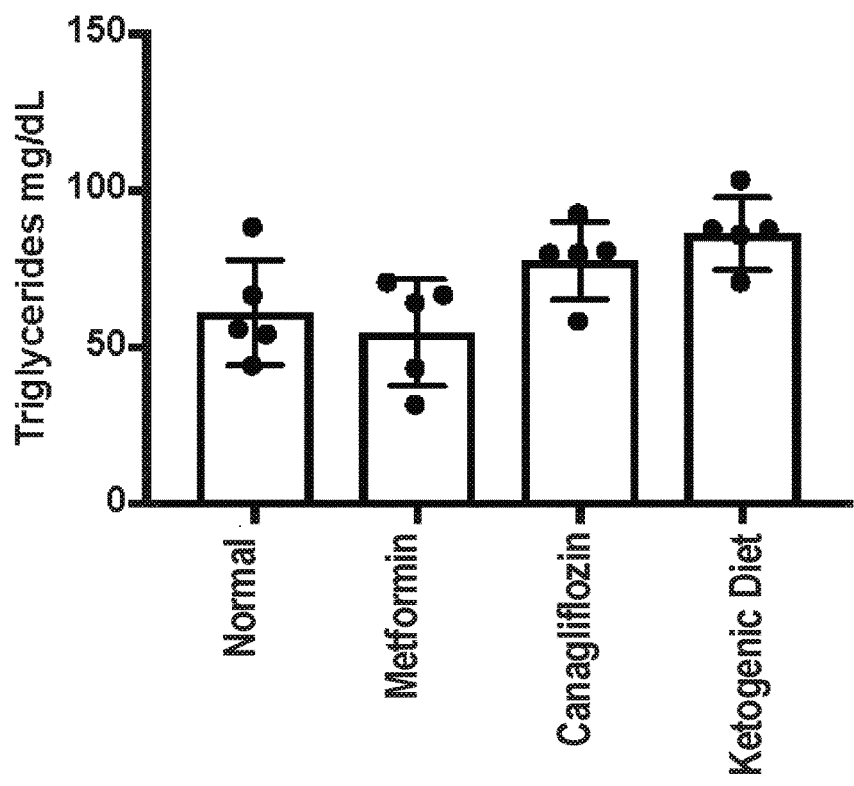

Wild-type mice were treated with therapeutic doses of compounds targeting a variety of kinases in the insulin receptor/PI3K/mTOR pathway, including inhibitors of INSR/IGFR, PI3K, AKT, and mTOR, and after treatment their blood glucose levels were monitored over time (FIG. 1A, FIG. 5A, FIG. 5B). The inventors observed that many of these agents cause significant increases in blood glucose levels. Importantly, the inventors noticed that the hyperglycemia resolved after only a few hours without additional intervention, suggesting that PI3K signaling had been reactivated in muscle and liver despite the presence of the drug. For each of the agents that caused an increase in blood glucose, there was also an increase in the amount of insulin released in the serum as measured by ELISAs for insulin over time (FIG. 1B) and c-peptide, which is clinically used as a surrogate for insulin over time (FIG. 1C, FIG. 5C, FIG. 5D).

To assess if these PI3K inhibitor-induced spikes in glucose and insulin were affecting tumors, the inventors performed fluorodeoxyglucose positron emission tomography FDG-PET on mice bearing orthotopic Kras-Tp53-Pdx-Cre (KPC) tumor allografts in the pancreas. The inventors observed an increase in glucose uptake in these tumors in the acute setting after PI3K inhibition as compared to vehicle treated mice, indicating that the spikes in insulin could be causing transient increases in glucose uptake in these tumors (FIG. 1D).

Example 2: Insulin Stimulates PI3K Signaling in the Context of PI3K Inhibition

Figure 2A:
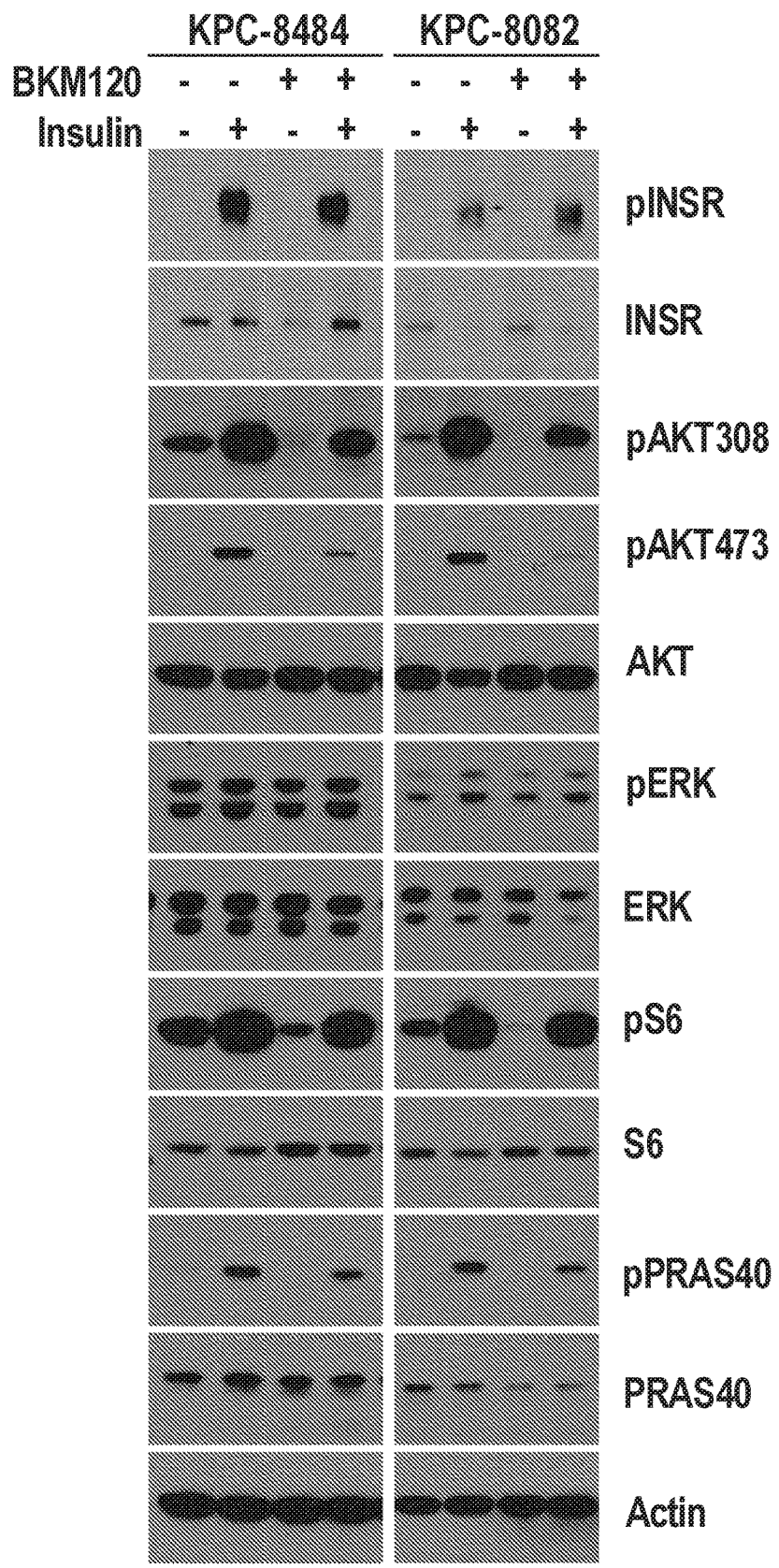
FIG. 2A-2C demonstrate the impact of feedback levels of insulin on cellular proliferation, signaling and survival.
Figure 2B:
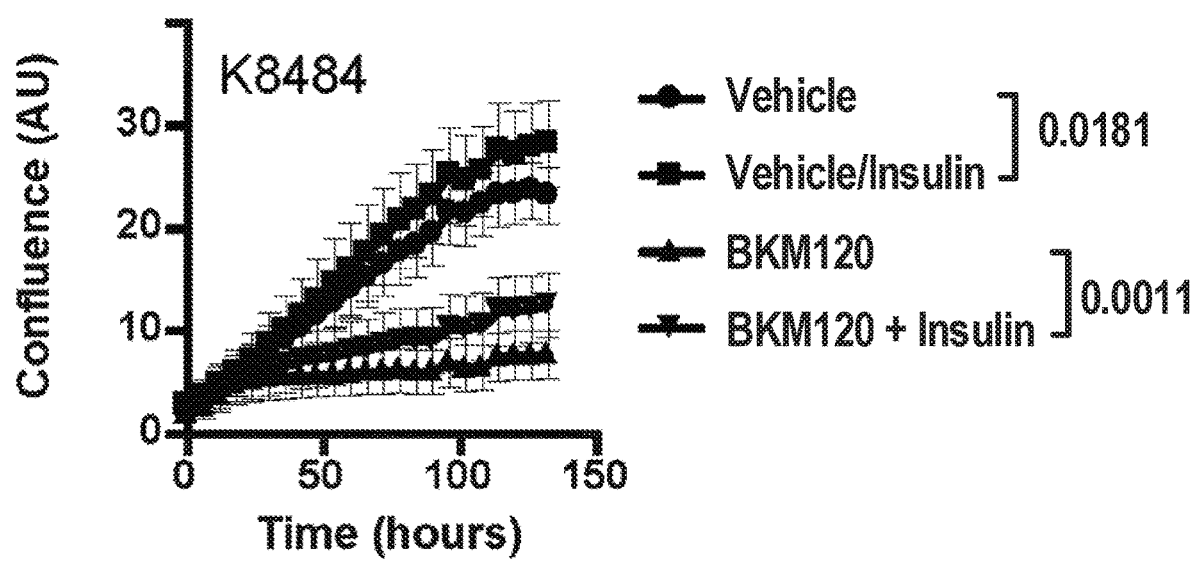
Figure 2C:
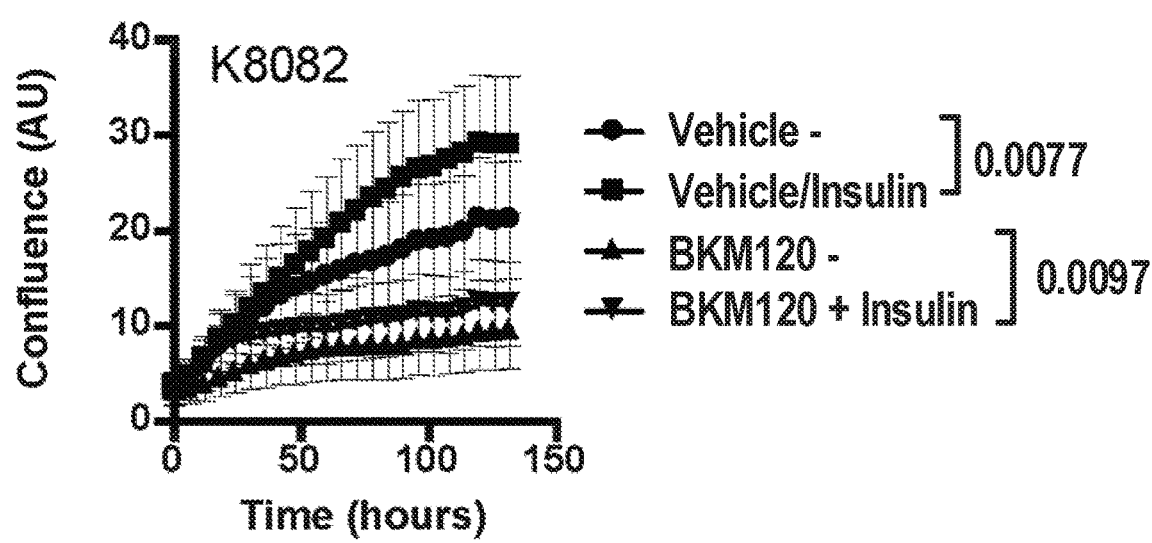

To test whether or not these spikes in insulin were stimulating PI3K signaling in the context of PI3K inhibition, KPC cells were treated in vitro with the PI3K inhibitors in the presence or absence of 10 ng/ml insulin, the level observed in the mice within 15-30 min after drug administration (FIG. 1D). This level of insulin was sufficient to partially rescue PI3K signaling in the continued presence of PI3K inhibitors as indicated by partial re-activation of phosphorylated AKT (pAKT) and almost complete reactivation of phosphorylated S6 (pS6), a reporter of growth signaling through the mTORC1 complex (FIG. 2A). In addition, this enhanced signaling correlated with a partial recovery of cellular proliferation (FIG. 2B-2C).

Similar effects of insulin stimulating proliferation in the presence of a PI3K inhibitor were observed in a variety of other tumor cell lines and patient derived organoids from breast, endometrium and prostate tumors (FIG. 6A-6G). The amount of stimulation was not uniform across all cell lines, as would be expected in tumors with variable expression of the insulin receptor and differential dependence on PI3K signaling for growth. These observations support the conclusions that insulin is a potent activator of PI3K signaling in certain tumors, and that elevation of serum insulin following PI3K inhibitor administration can reactivate PI3K signaling and potentially other PI3K-independent responses to insulin in both normal tissues and tumors.

Example 3: Metform, SGLT2 Inhibitors, Ketogenic Diet

Research and care for diabetic patients has resulted in the development of numerous approaches to manage blood glucose and insulin levels. Utilizing these tools, the inventors sought to identify approaches to augment PI3K inhibitor therapies by circumventing the acute glucose/insulin feedback. Metformin and sodium-glucose co-transporter 2 (SGLT2) inhibitors were evaluated, as well as a ketogenic diet in our murine models of cancer.

Figure 3A:
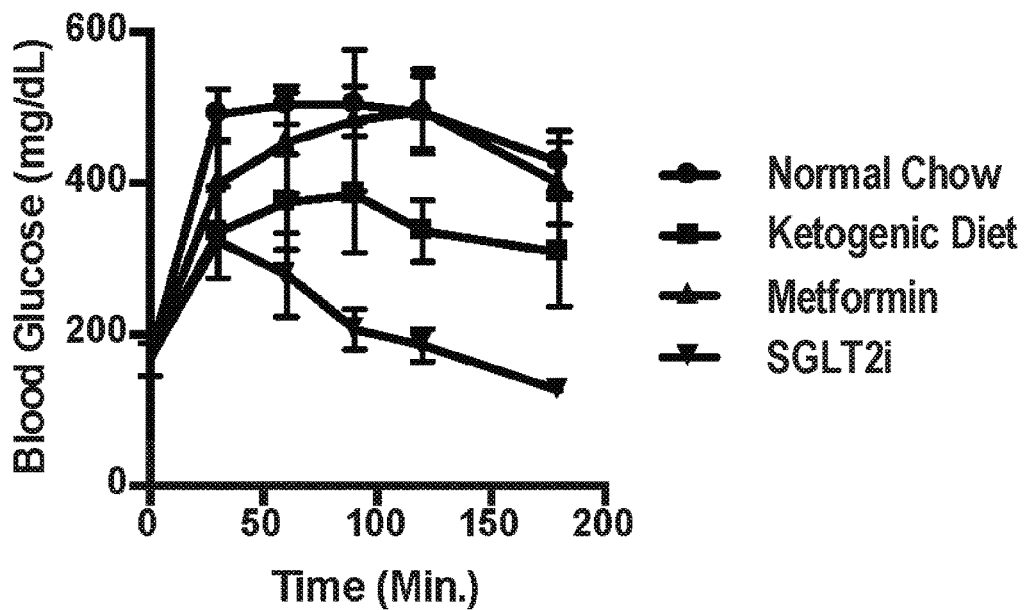
Figure 3B:
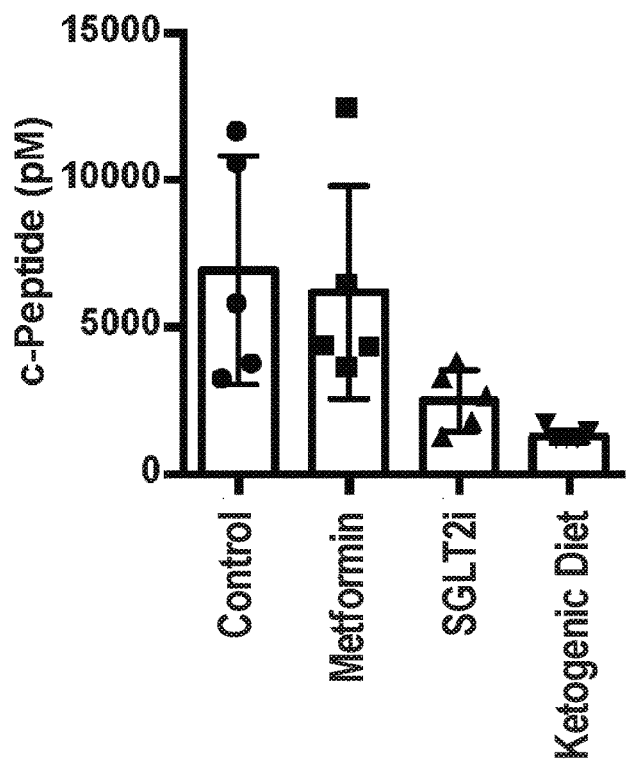
Figure 3C:
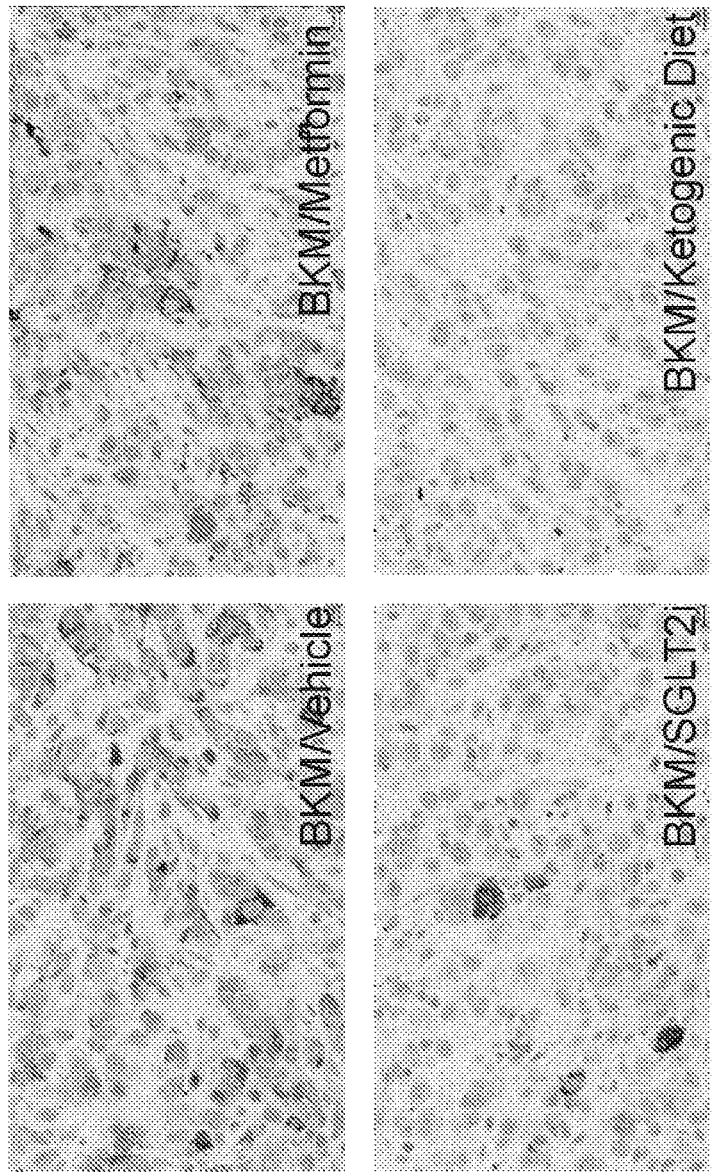
Figure 3D:
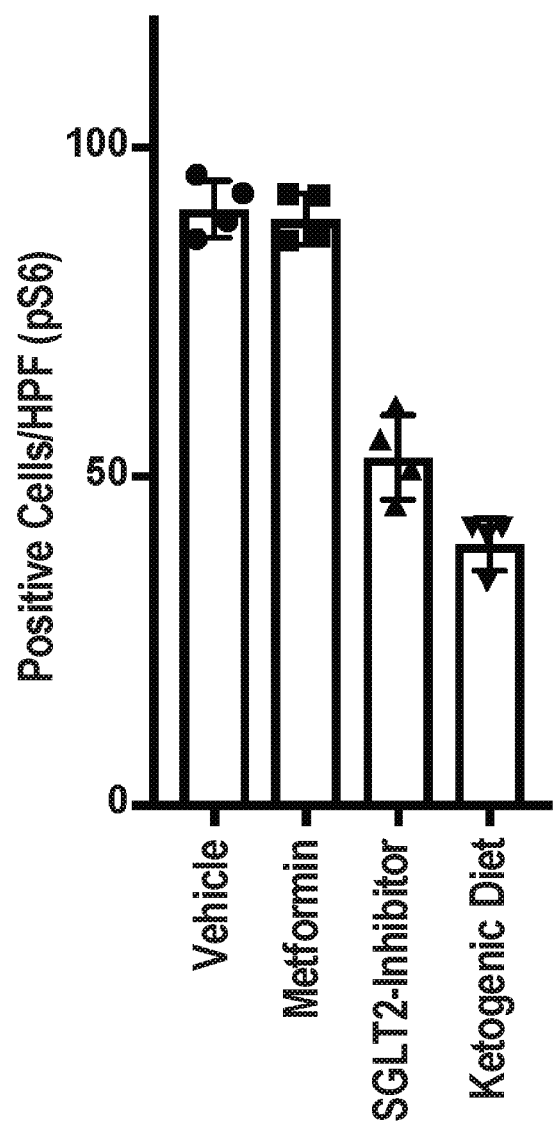
Figures 1, 3E:
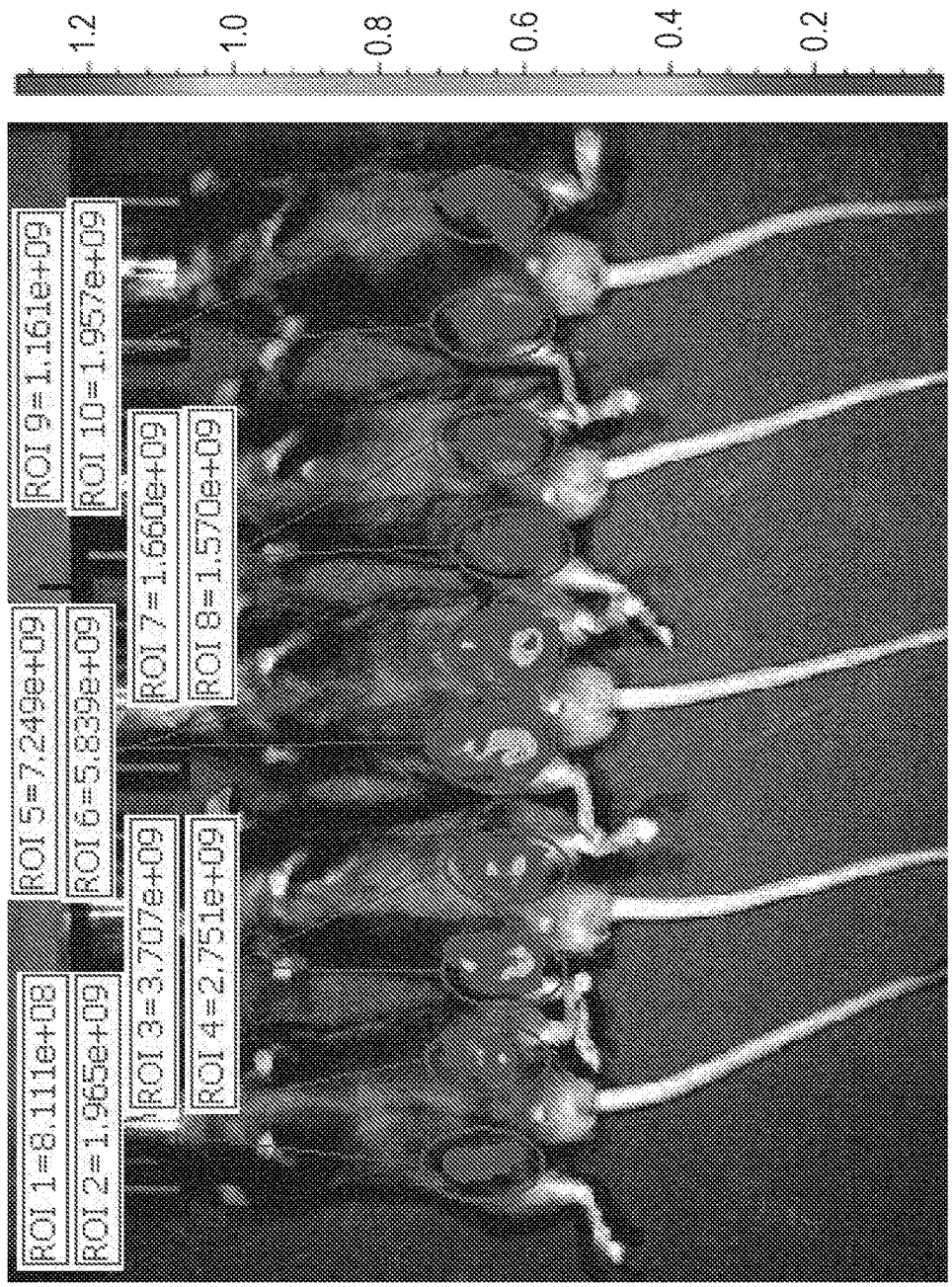
Figures 2, 3E:
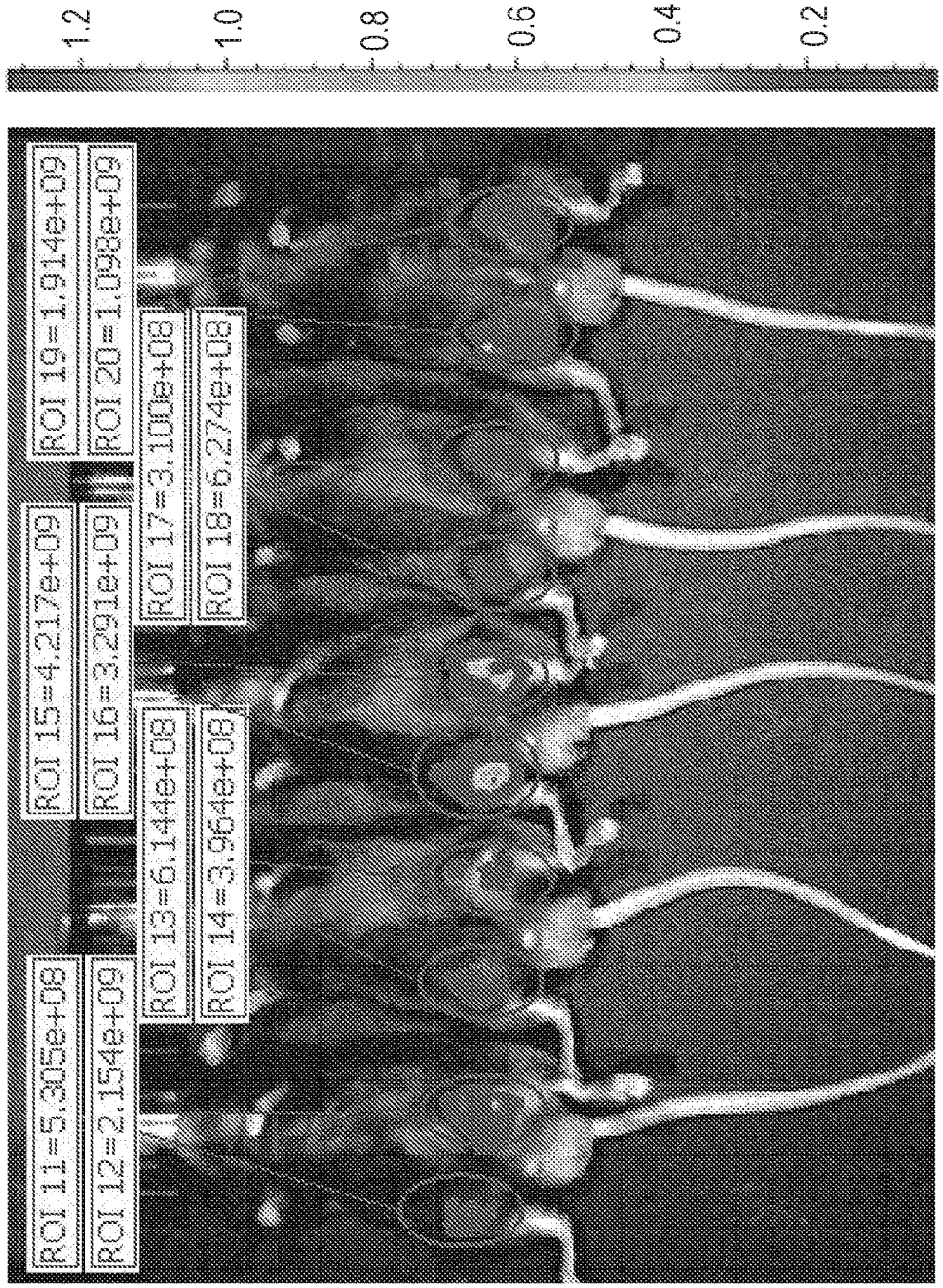
Figures 3, 3E:
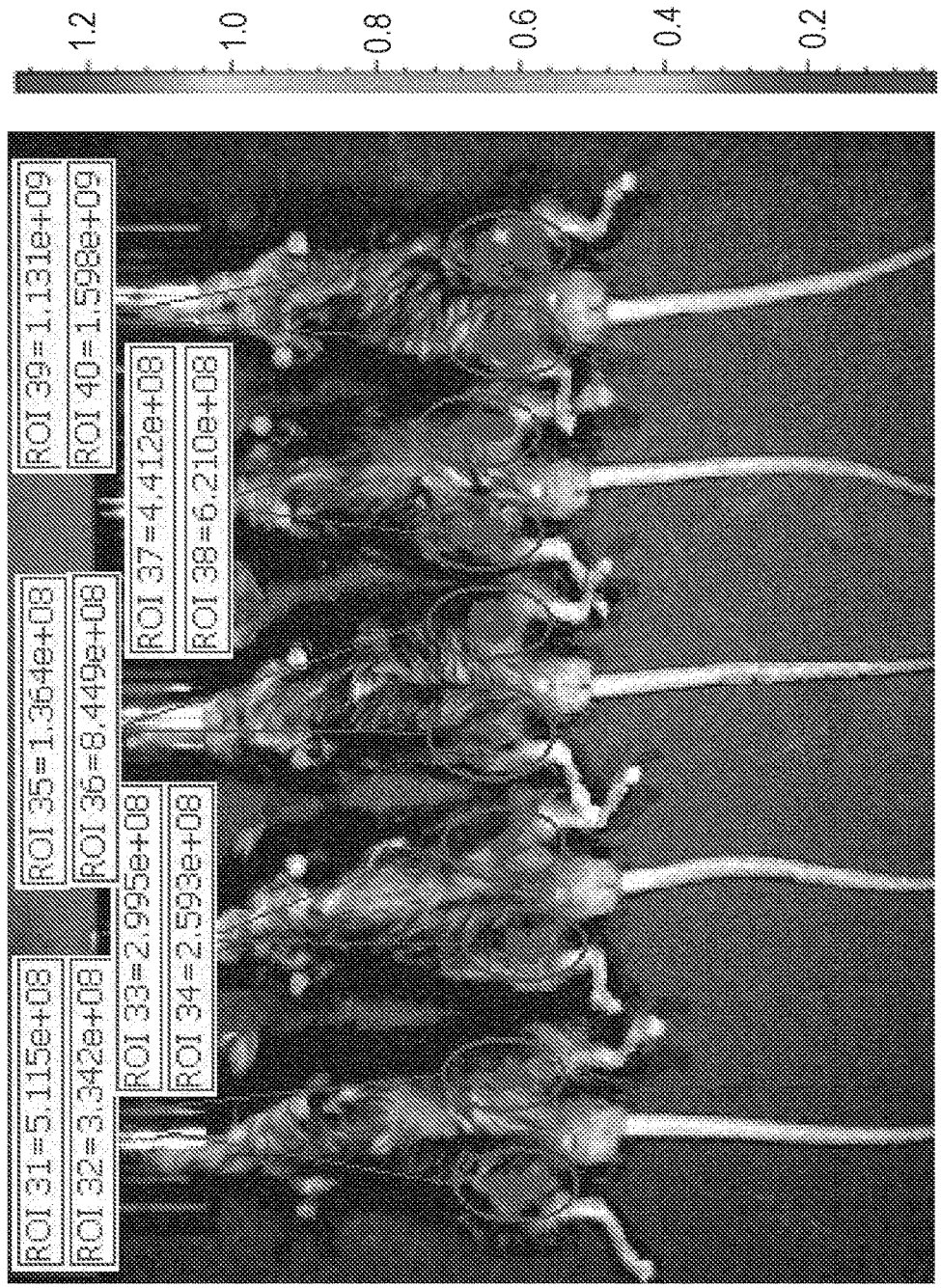
Figures 3, 3E, 4:
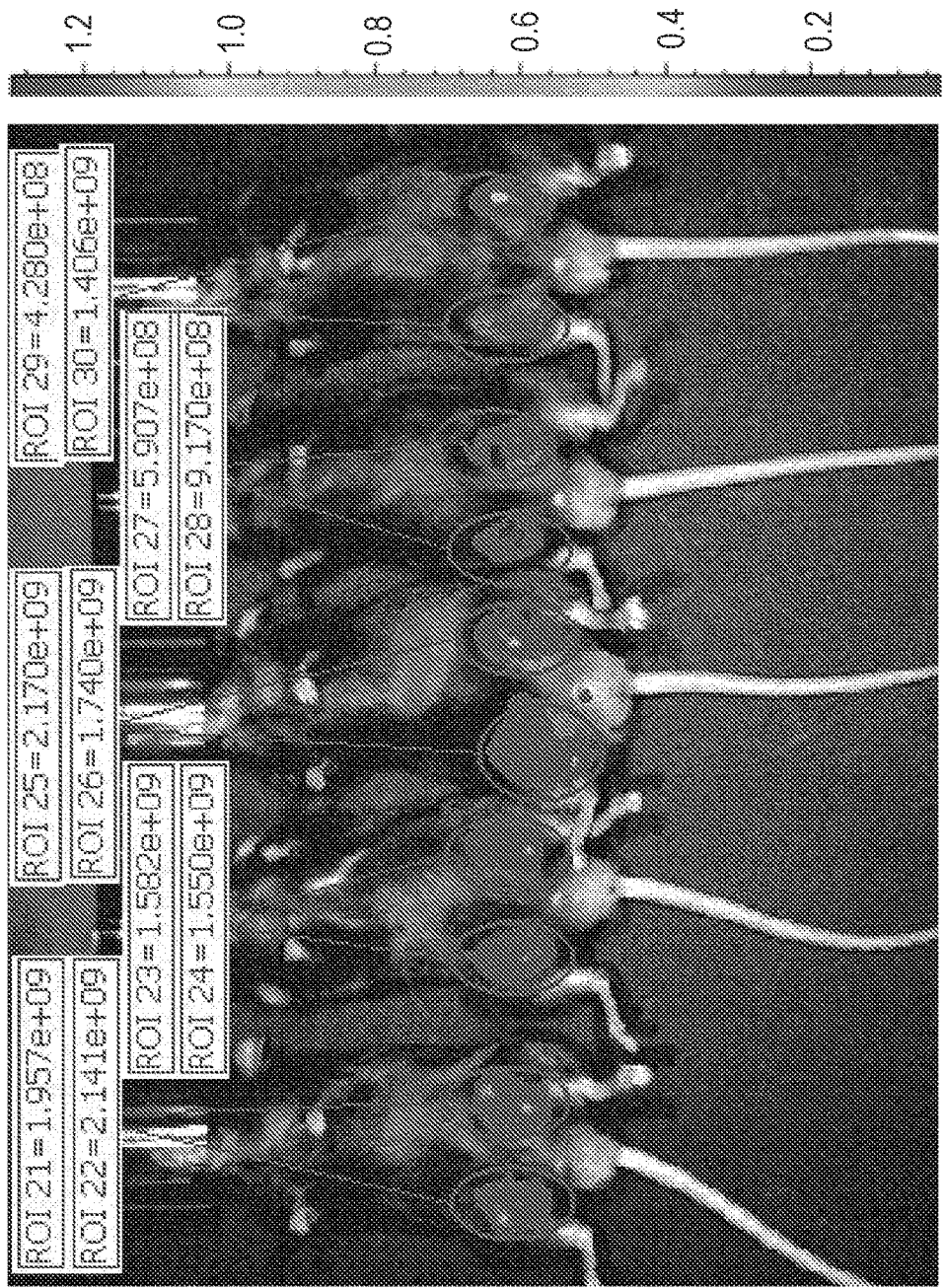
Figure 3F:
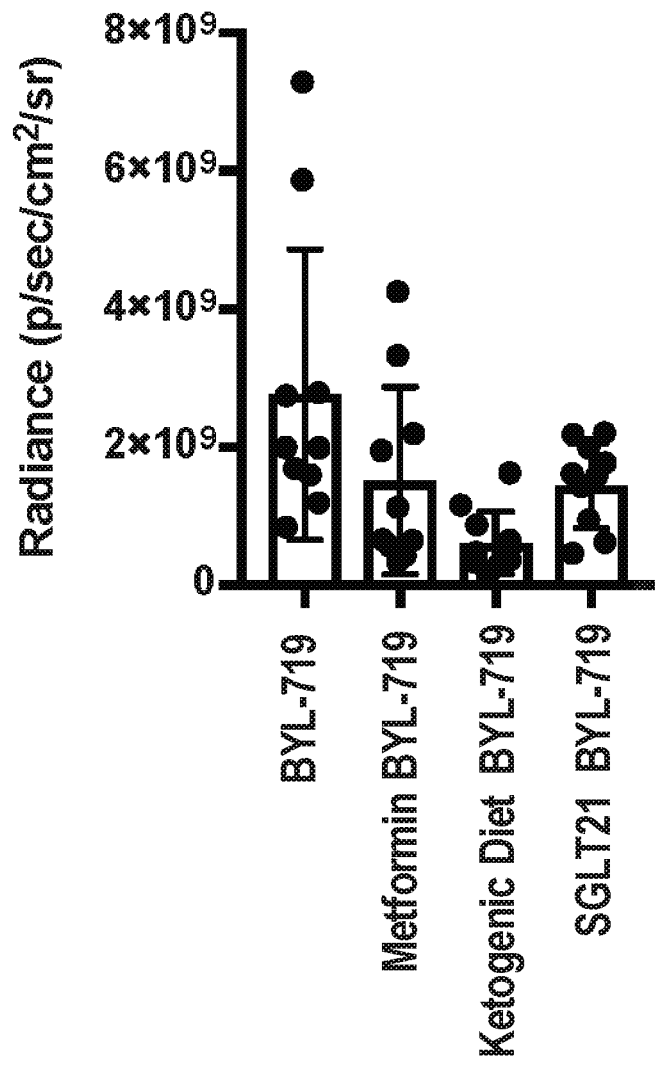
Figure 3G:
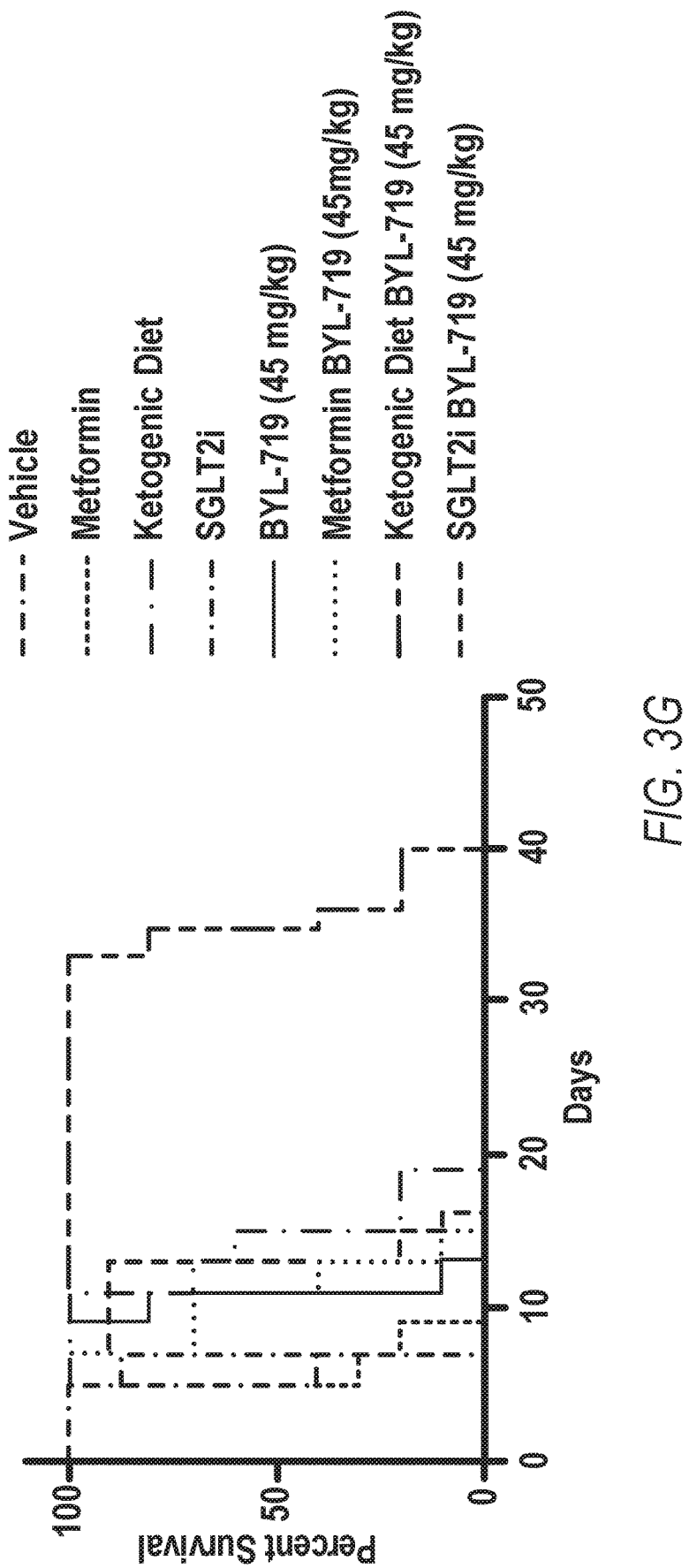

Treatment-naïve mice bearing KPC allografts were placed on a ketogenic diet or treated with metformin for 10 days prior to a single treatment with BKM120. During this treatment, blood glucose was monitored and, after 3 hours, c-peptide (a surrogate for blood insulin) was evaluated (FIG. 3A-3B). In some mice, tumors were harvested at 90 minutes and stained for the pS6 (FIG. 3C-3D). These results demonstrated that pretreatment with metformin had only minimal impact on the PI3K inhibitor-induced elevation in blood glucose and insulin levels or on growth signaling through mTORC1. In contrast, both the SGLT2 inhibitor and the ketogenic diet approaches decreased the resulting hyperglycemia and reduced the total insulin that was released in response to BKM120 treatment, and that these effects correlated with reduced signaling through mTORC1 in the tumor. Similar effects were seen in mice treated with the p110α specific inhibitor BYL-719 where the inventors observed an enhanced response of KPC allografts to BYL-719 in a manner concordant with the relative ability of each treatment to reduce serum insulin levels (FIG. 3E-G, FIG. 7A-D).

Example 4: Knockdown or Inhibition of Insulin Receptor

Figure 4A:
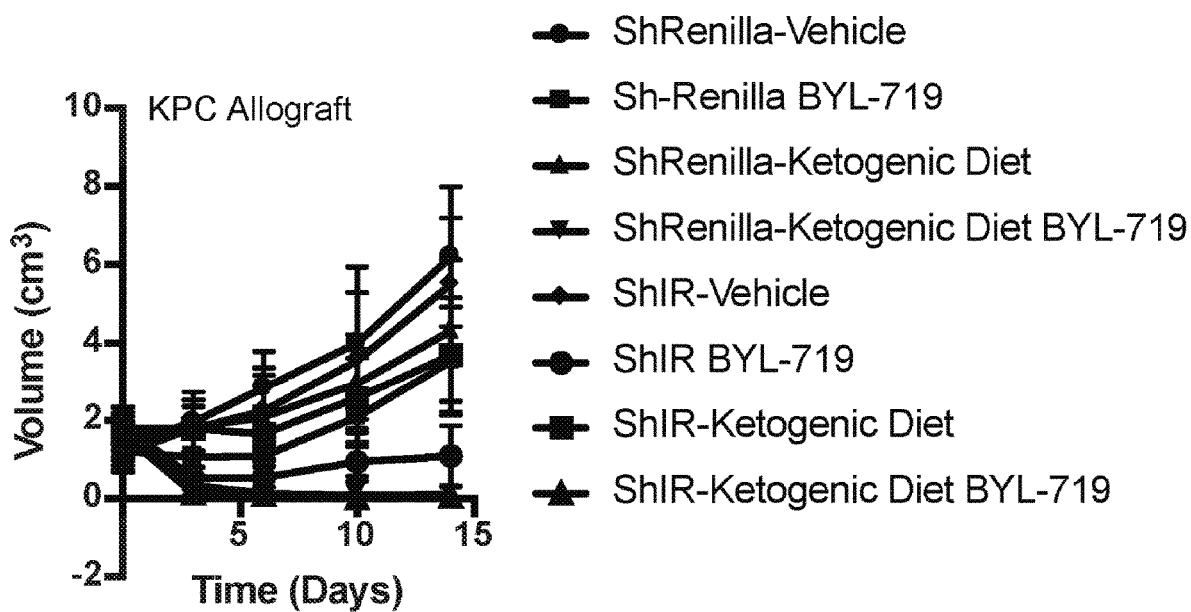
FIG. 4A-4E demonstrate the impact of circumventing the on-target glucose/insulin feedback of PI3K inhibitors upon tumor growth.

Various hormones and metabolites can reactivate growth in the setting of PI3K inhibition. To test if the enhancement in tumor signaling and growth is directly mediated by insulin, the inventors generated a doxycycline-inducible shRNA to target the insulin receptor in KPC tumors (FIG. 4A). Induction of this hairpin in the absence of a PI3K inhibitor had little effect on tumor growth. However, induction of the hairpin at the time of BYL719 treatment initiation resulted in tumor shrinkage that was almost as effective as the ketogenic diet (FIG. 4A). This result indicates that the insulin receptor is not playing a major role in the growth of this tumor until supra-physiologic amounts of insulin are released following treatment with a PI3K inhibitor. The specificity of this effect was further corroborated by combining the PI3K inhibitor, BKM120, with the insulin receptor/IGF1 receptor inhibitor, OSI-906, which resulted in a more effective response on the growth of KPC allografts than either drug alone (FIG. 8B-8G).

Example 5: Exogenous Insulin

Figure 4B:
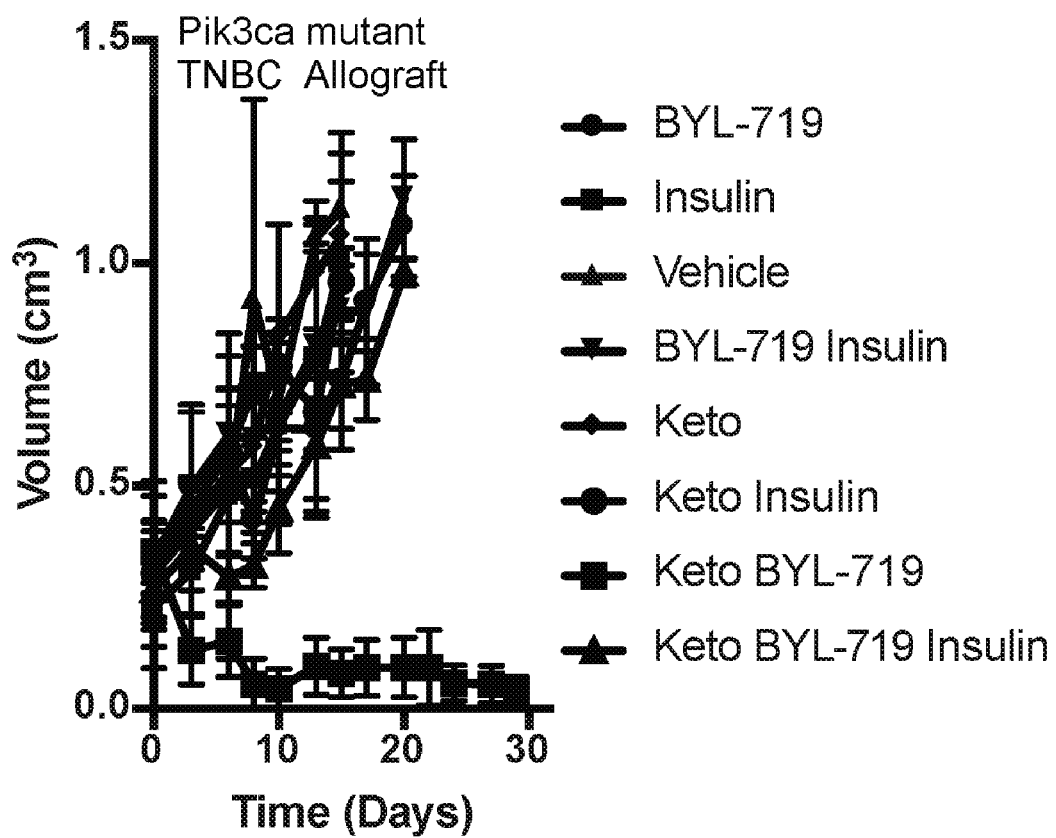
Figure 4C:
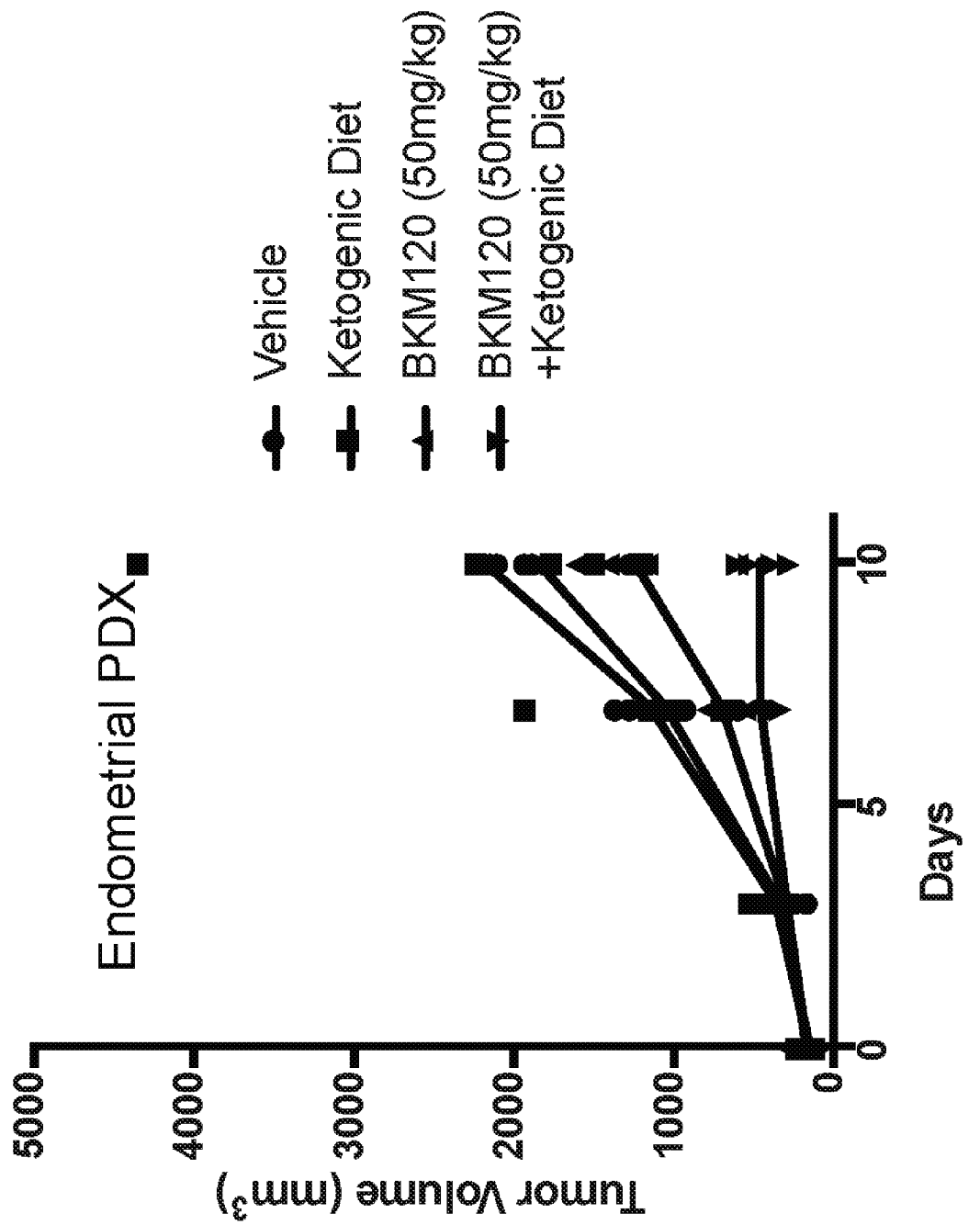
Figure 8A:
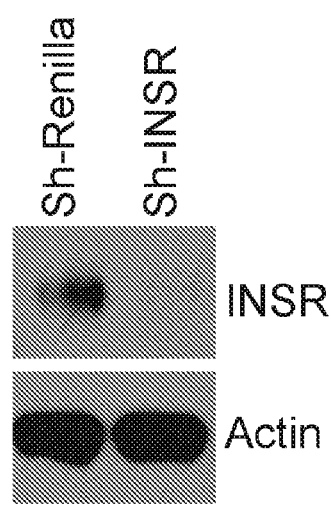
FIG. 8A-8H illustrates the role of inhibiting insulin receptor in the observed changes in tumor response.
Figure 8B:
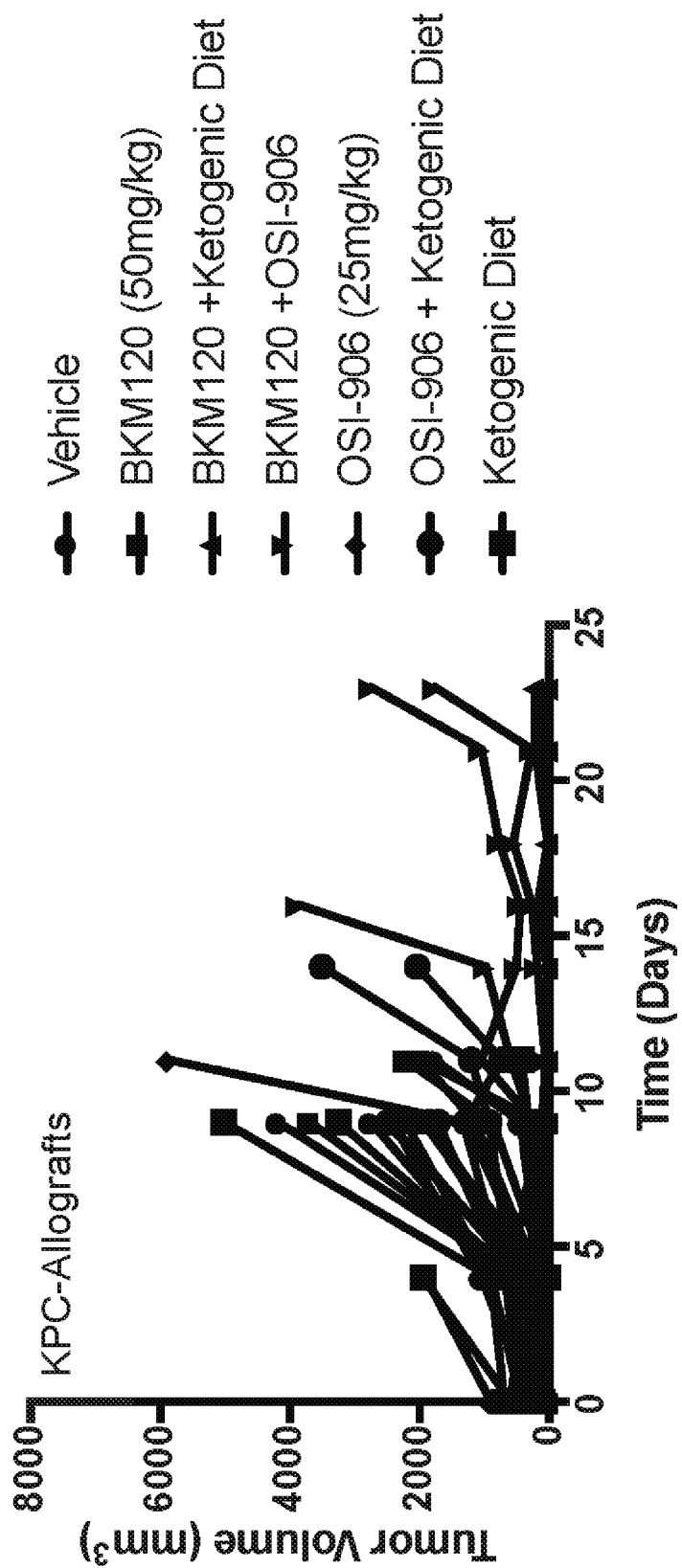
Figure 8C:
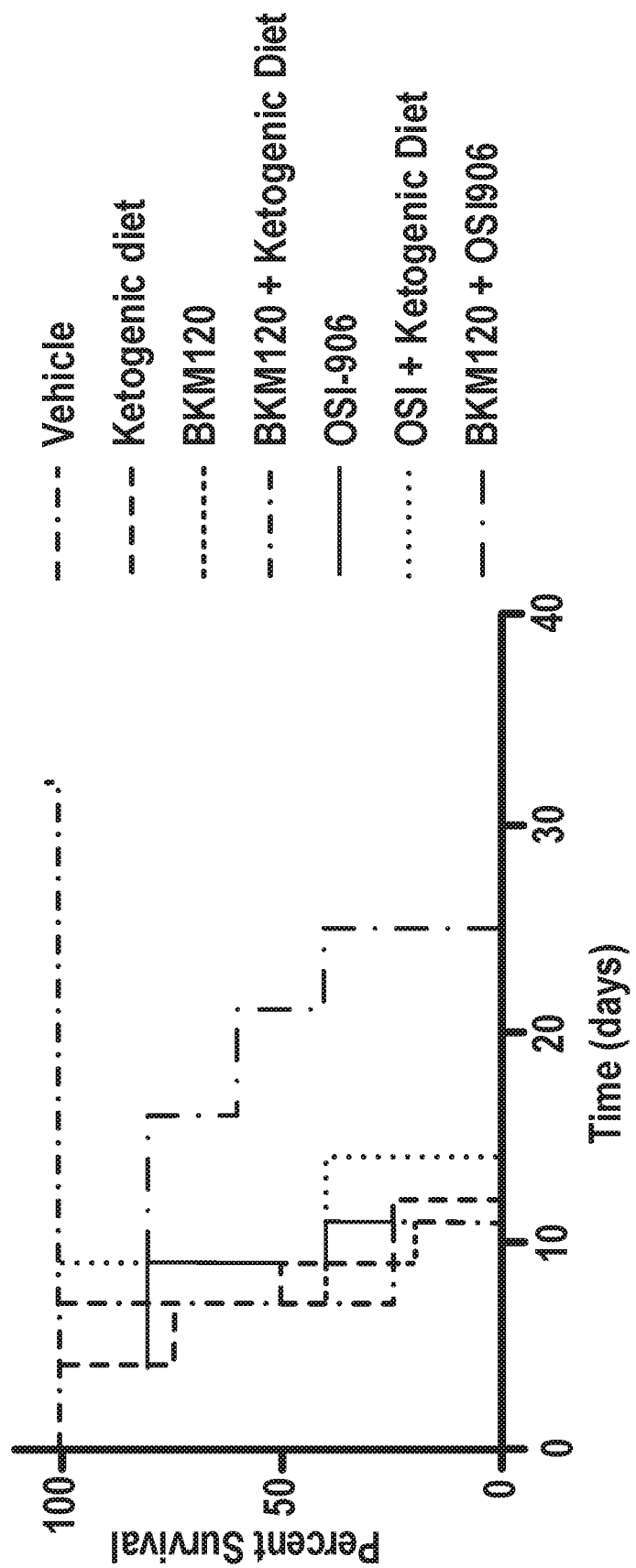
Figure 8D:
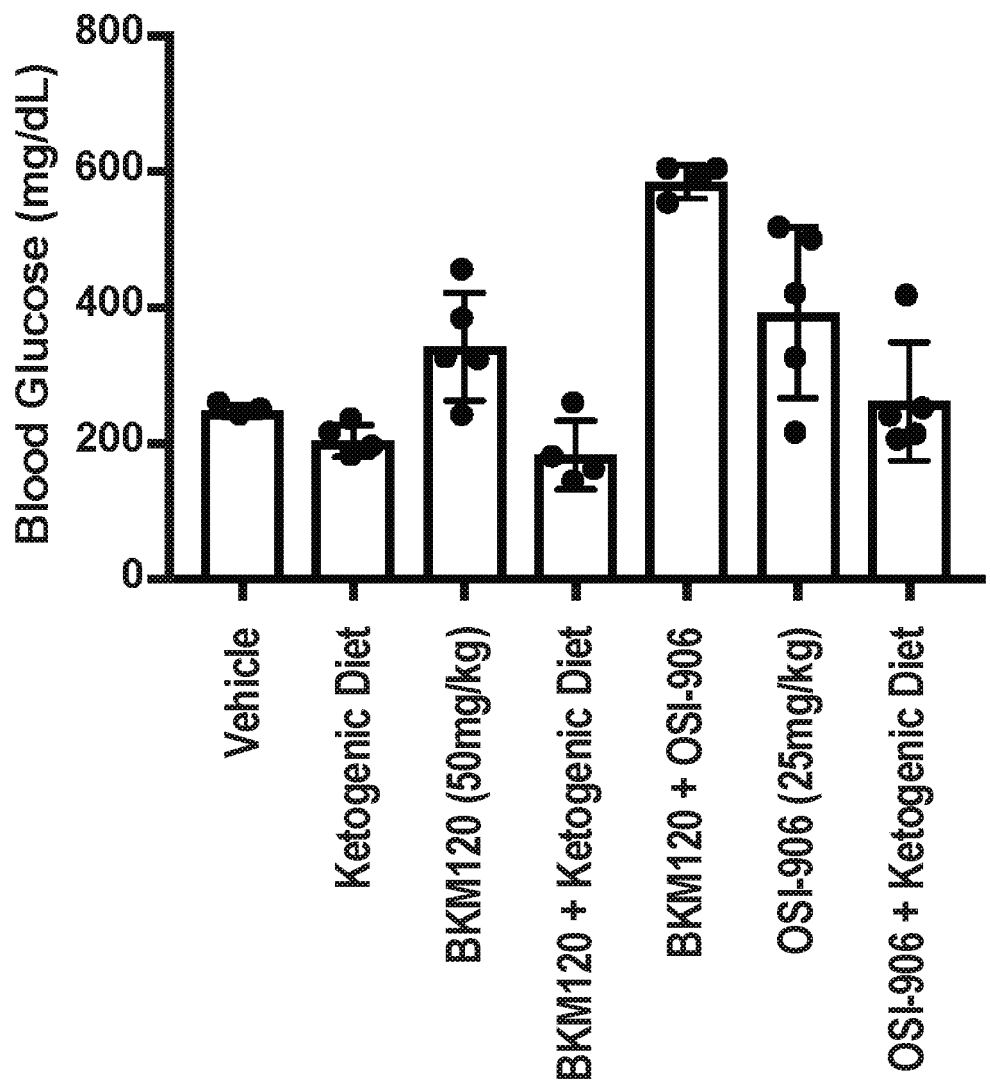
Figure 8E:
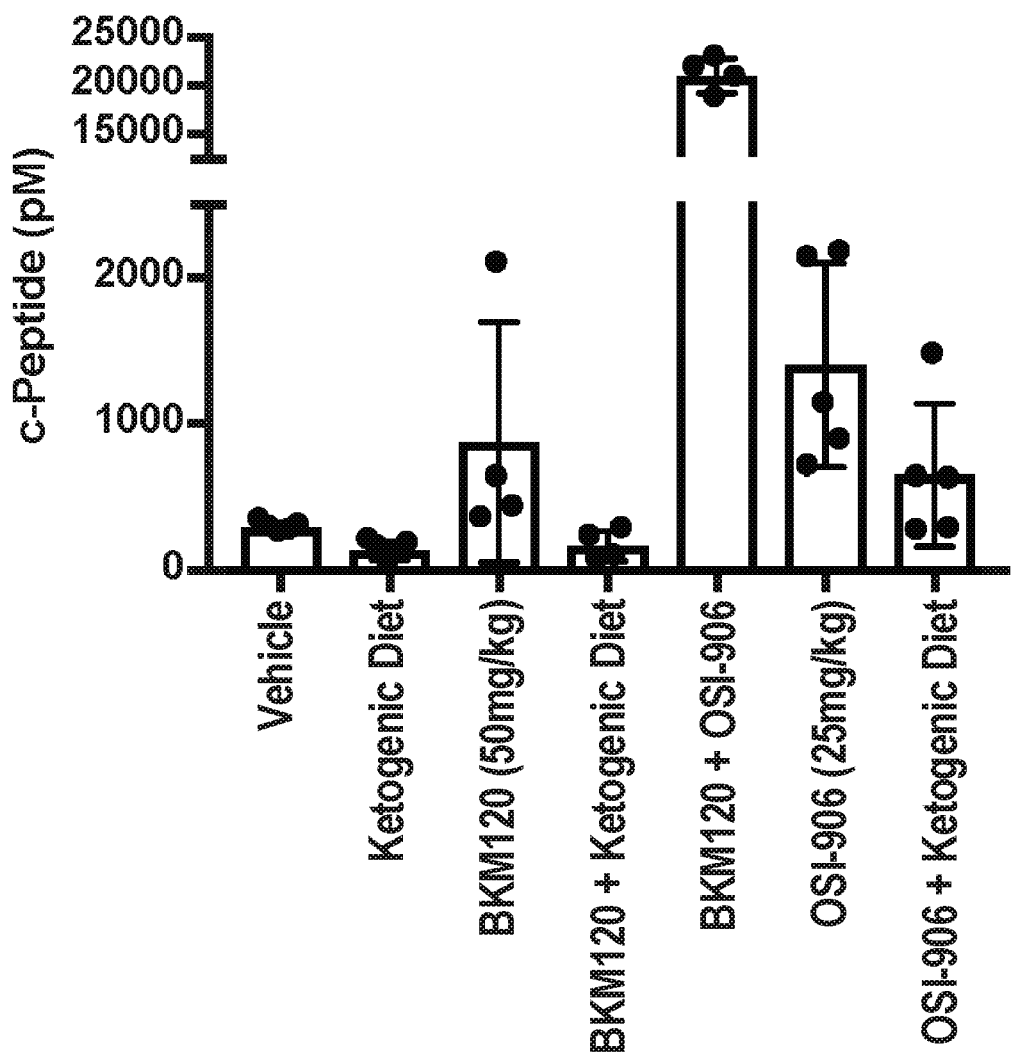
Figure 8F:
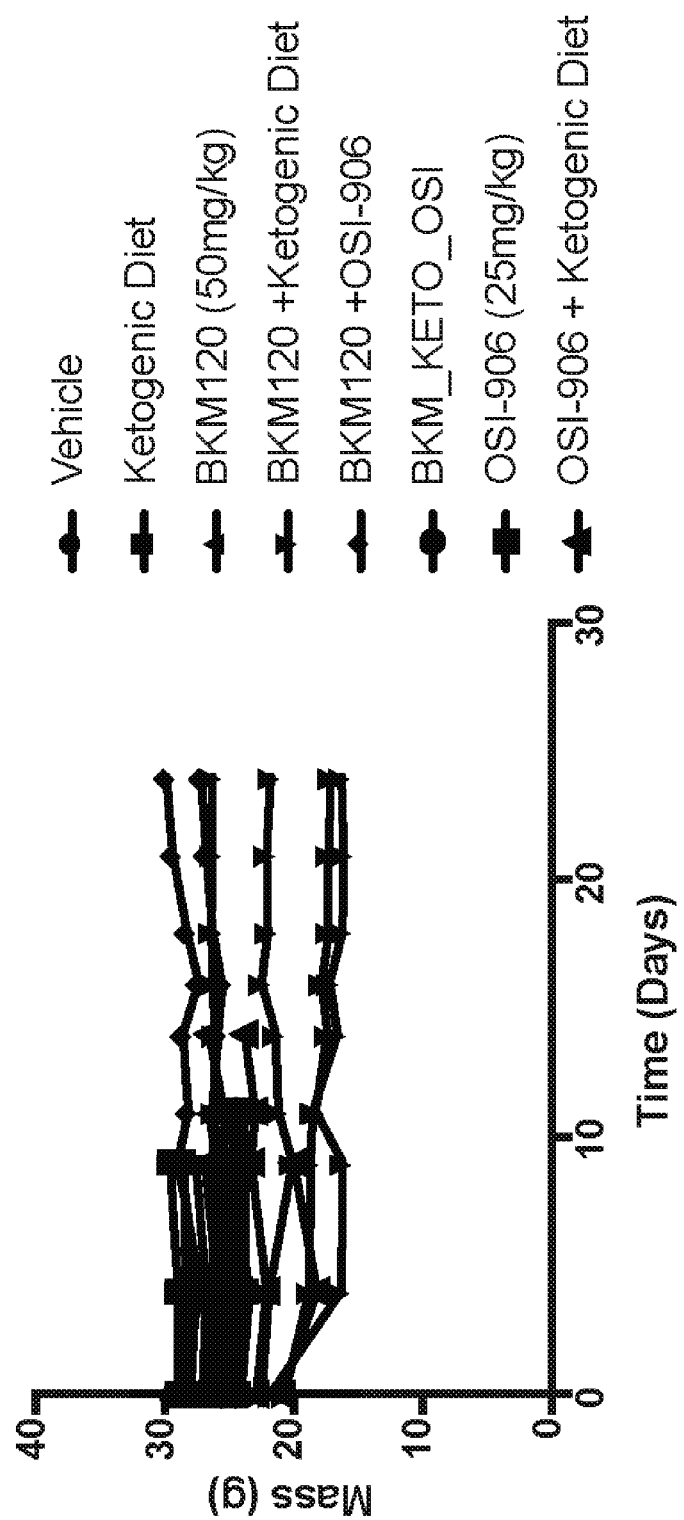
Figure 8G:
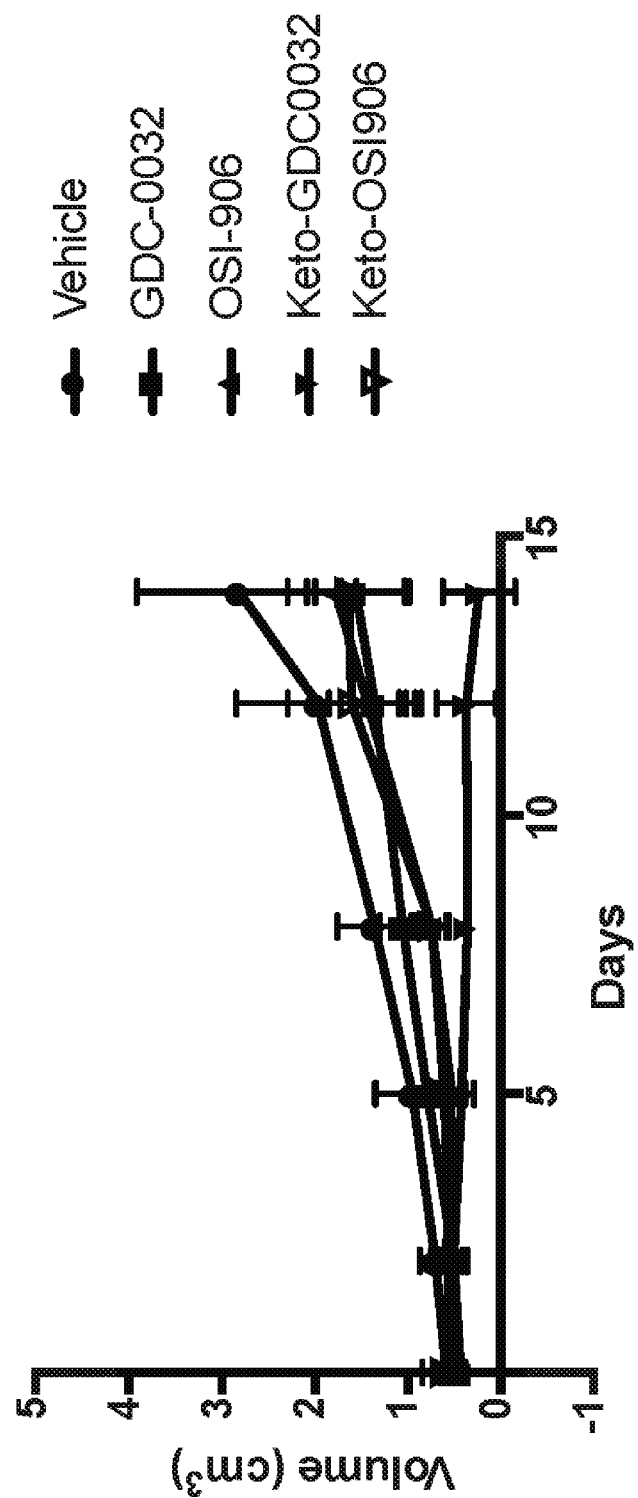
Figure 8H:
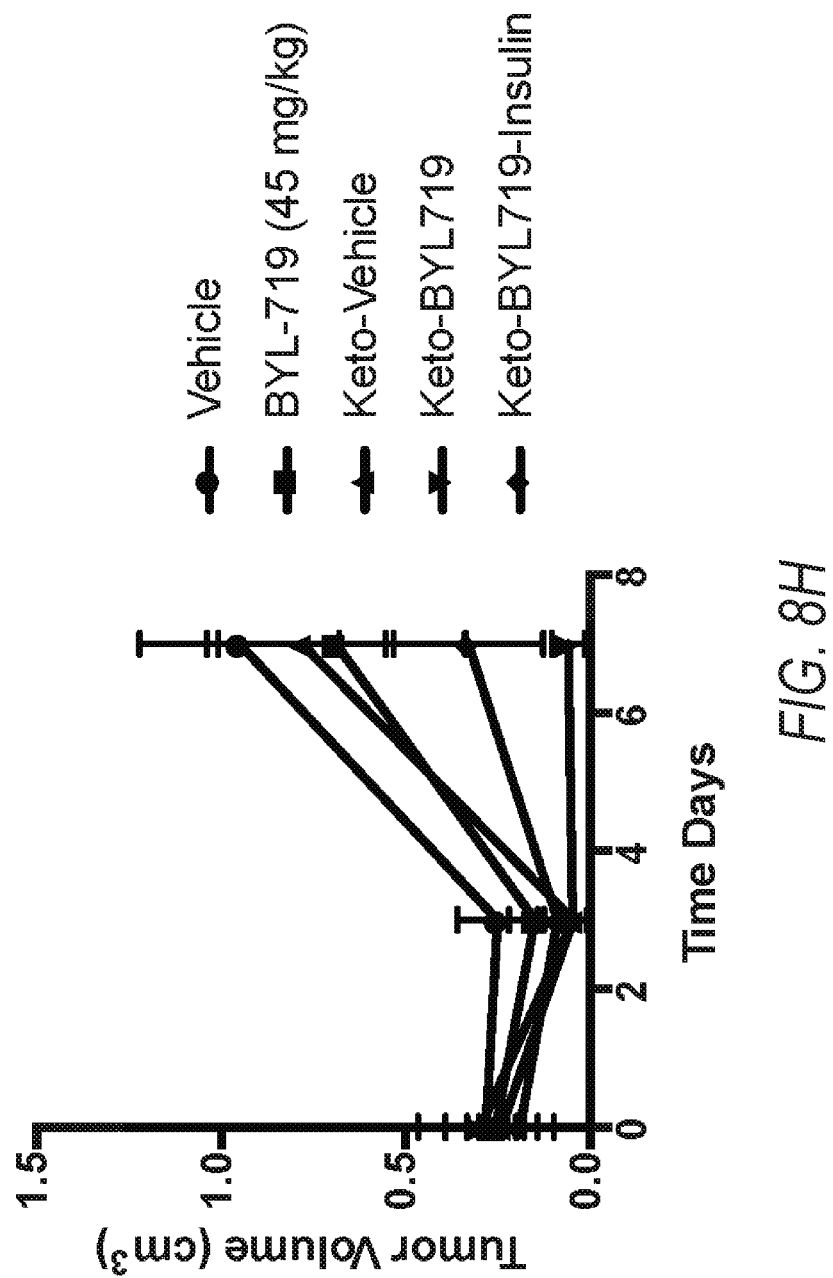
Figure 9A:
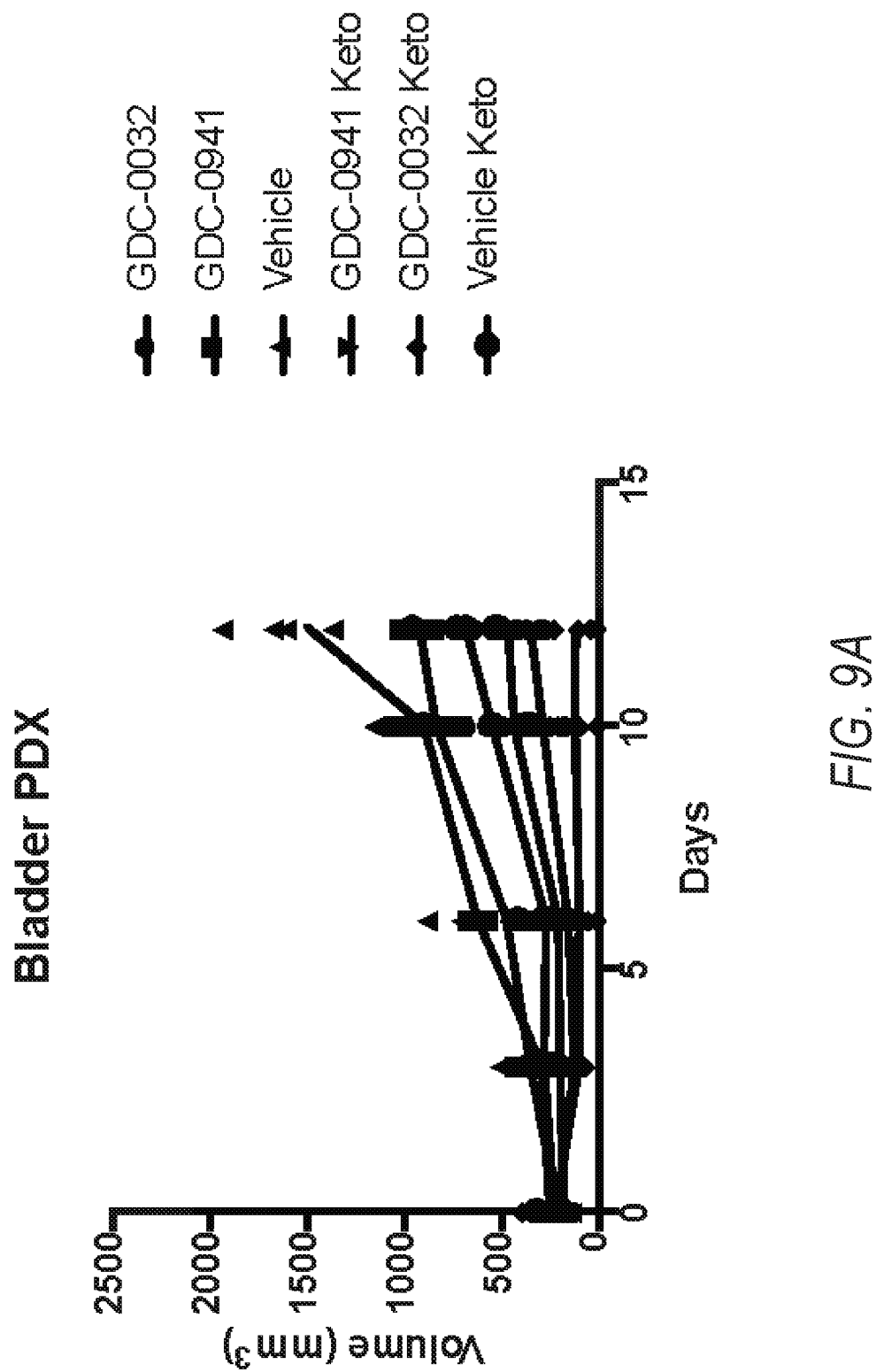
FIG. 9A-9E illustrates the impact of PI3K inhibitor treatments upon Subject-derived xenograft models of bladder cancer and syngeneic allograft models of PIK3CA mutant breast cancer.
Figure 9B:
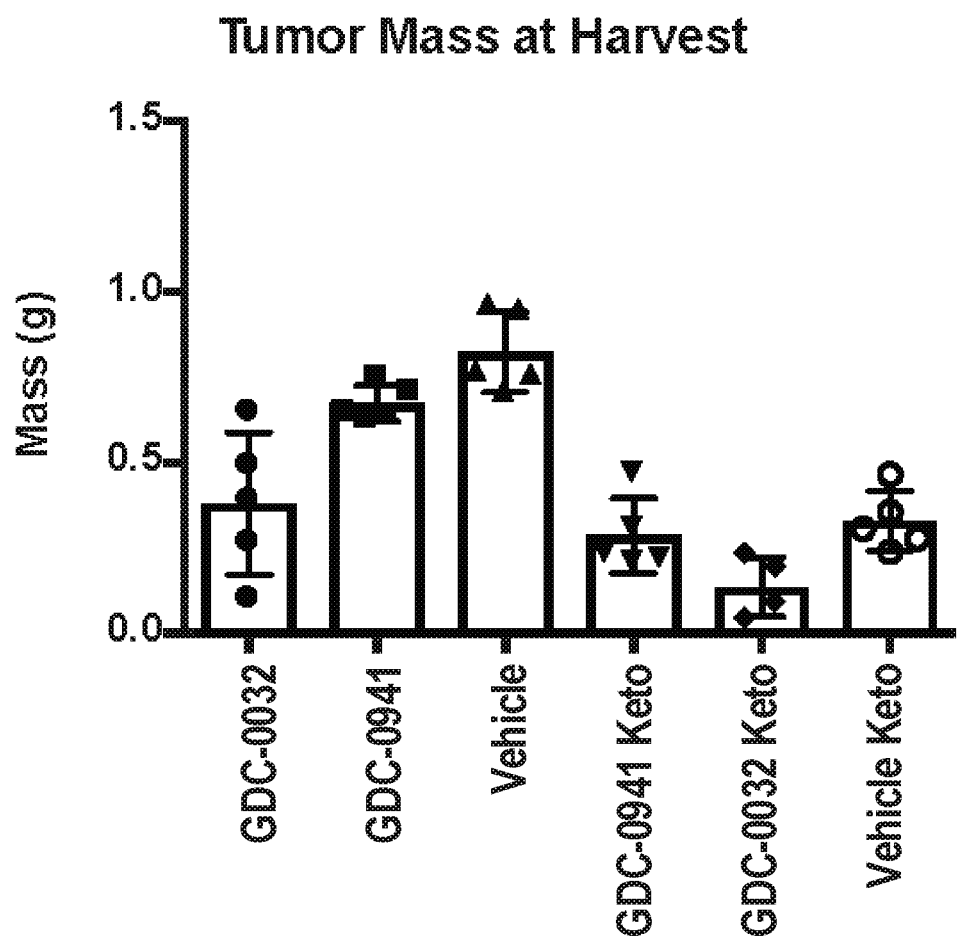
Figure 9C:
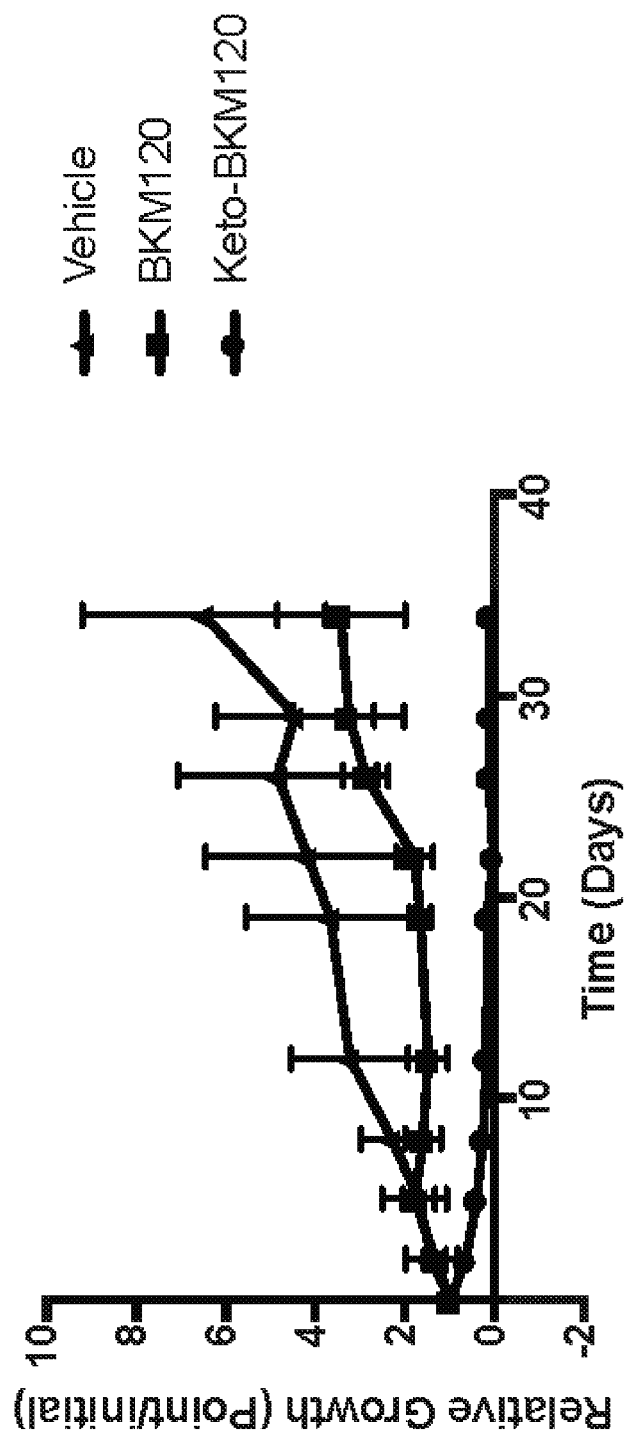
Figure 9D:
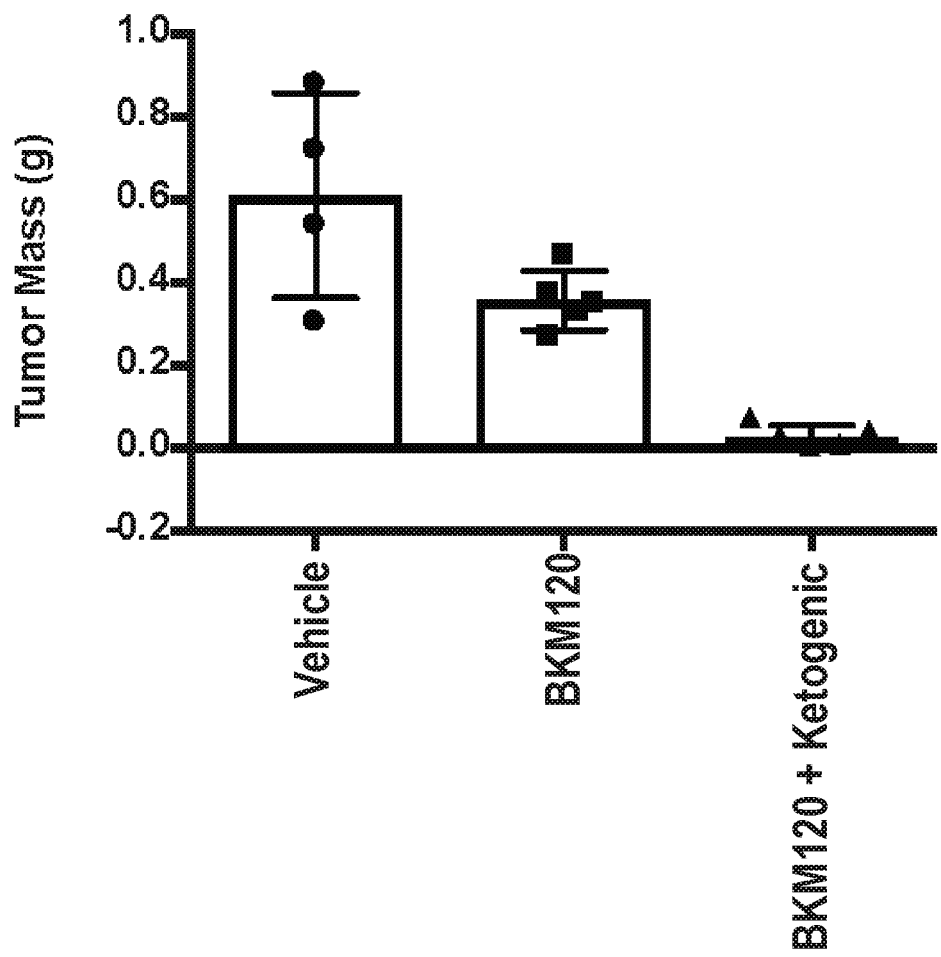
Figure 9E:
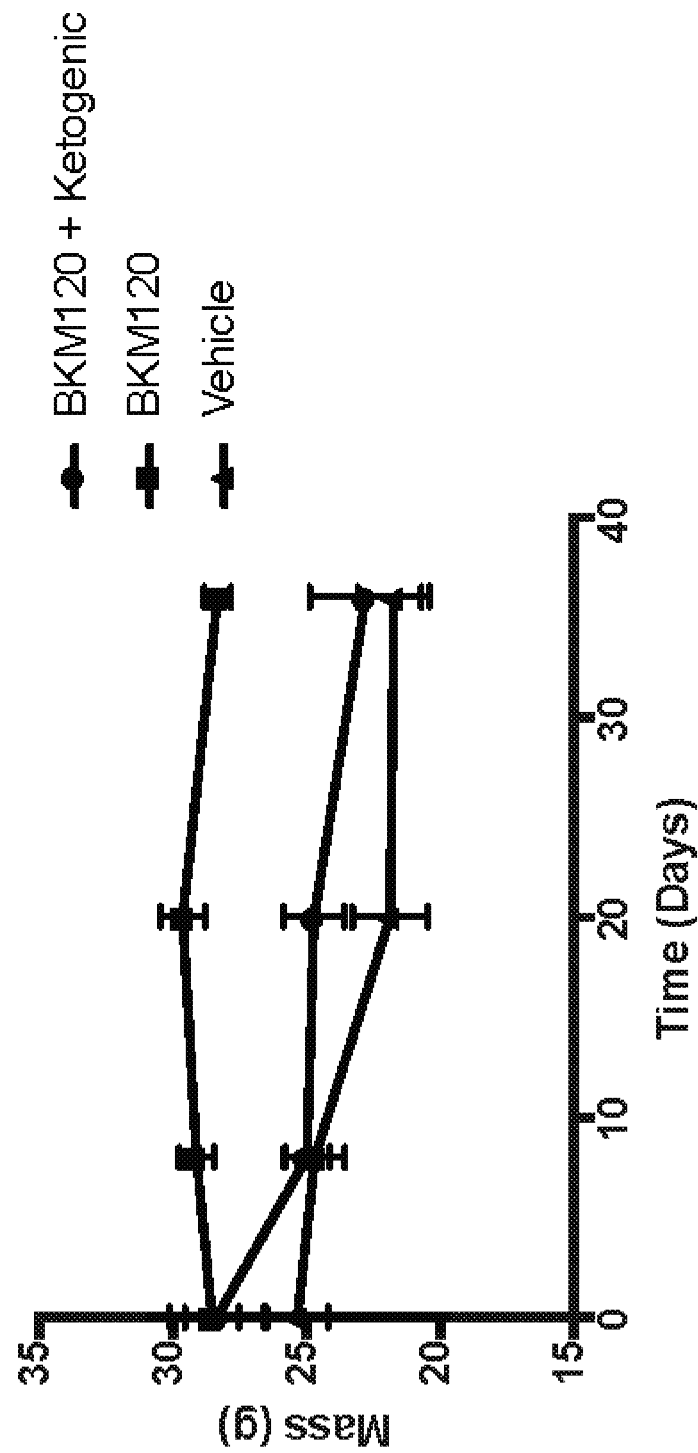
Figure 10A:
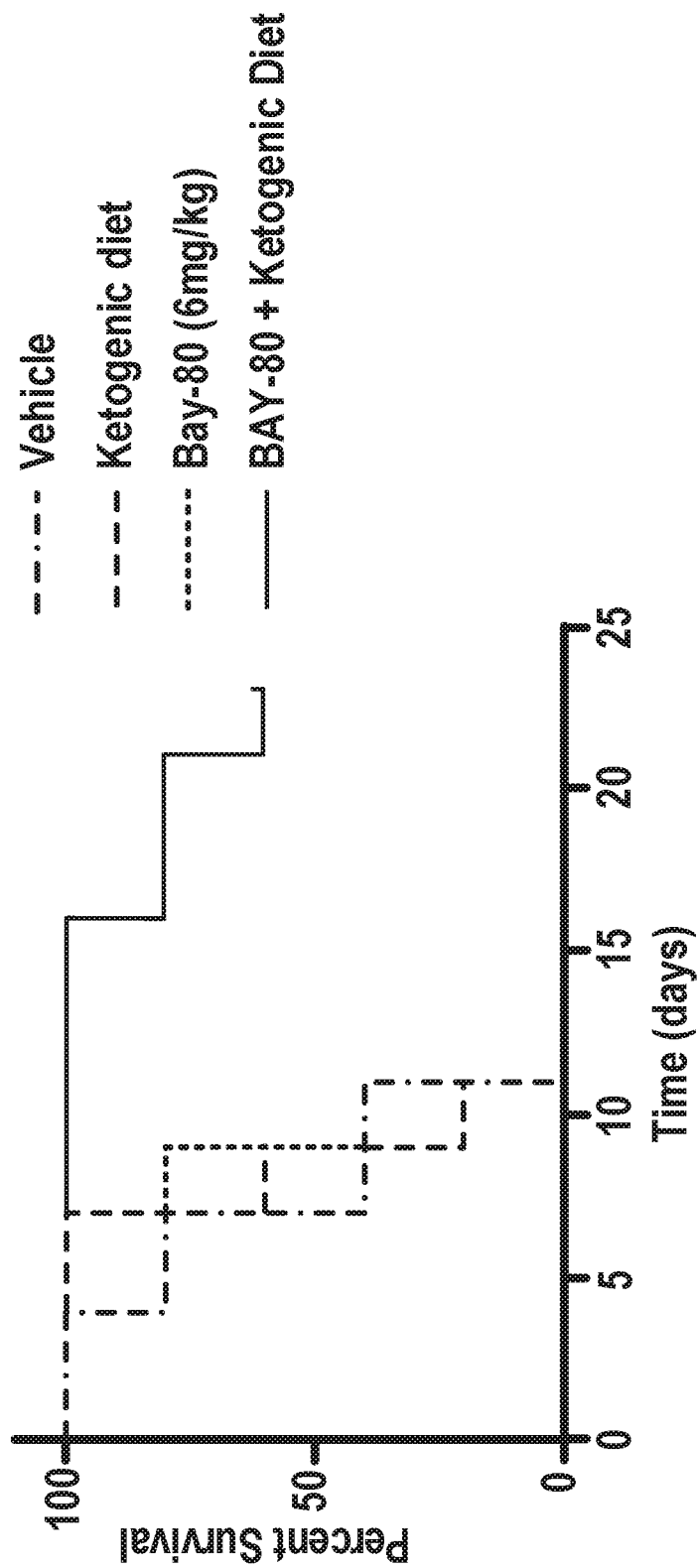
FIG. 10A-10E illustrate the impact of Capanilisib with or without ketogenic diet upon growth of orthotopic Kras-Tp53-Pdx-Cre (KPC) K8082 tumor model grown in the flank of wildtype c57/bl6 mice.
Figure 10B:
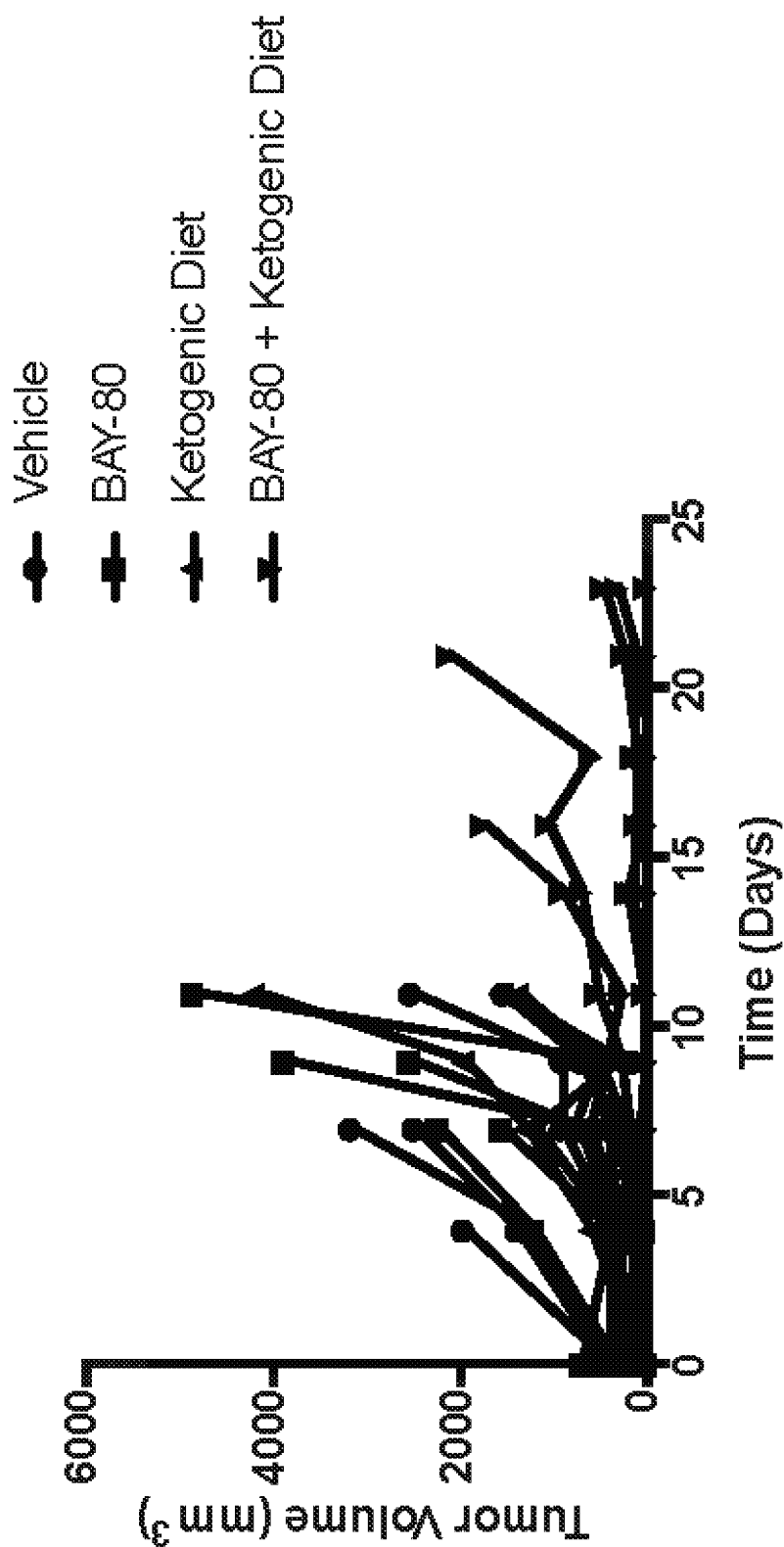
Figure 10C:
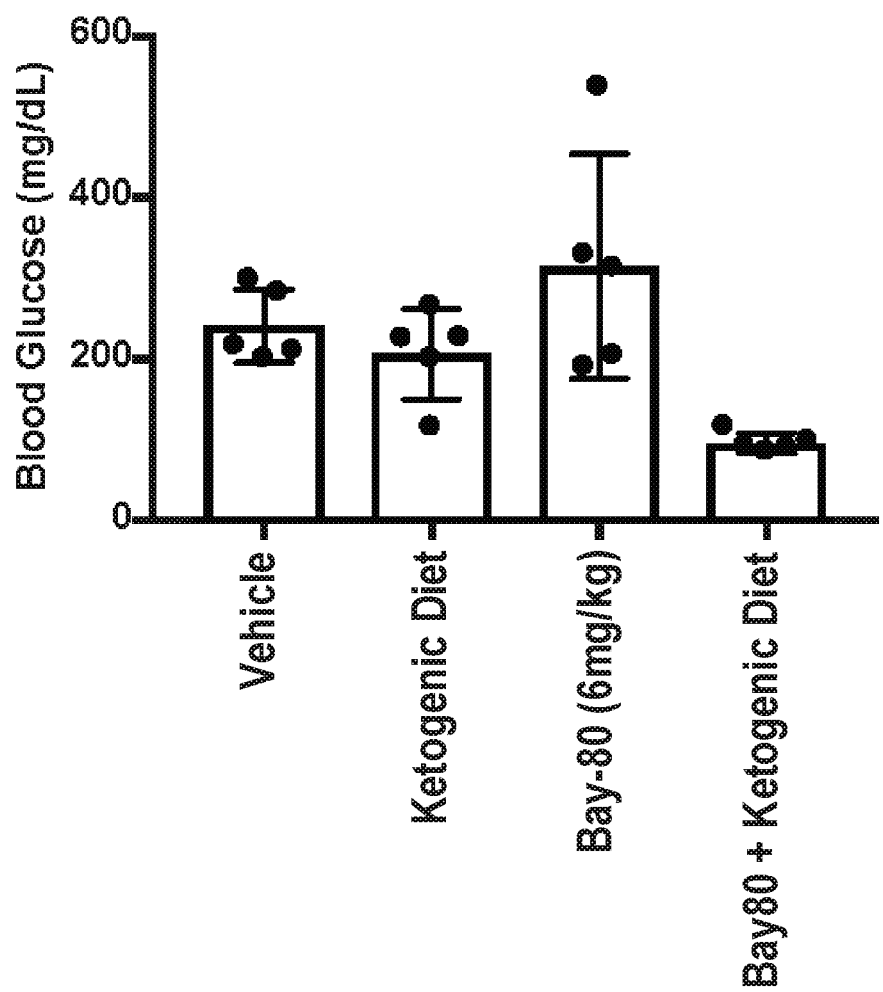
Figure 10D:
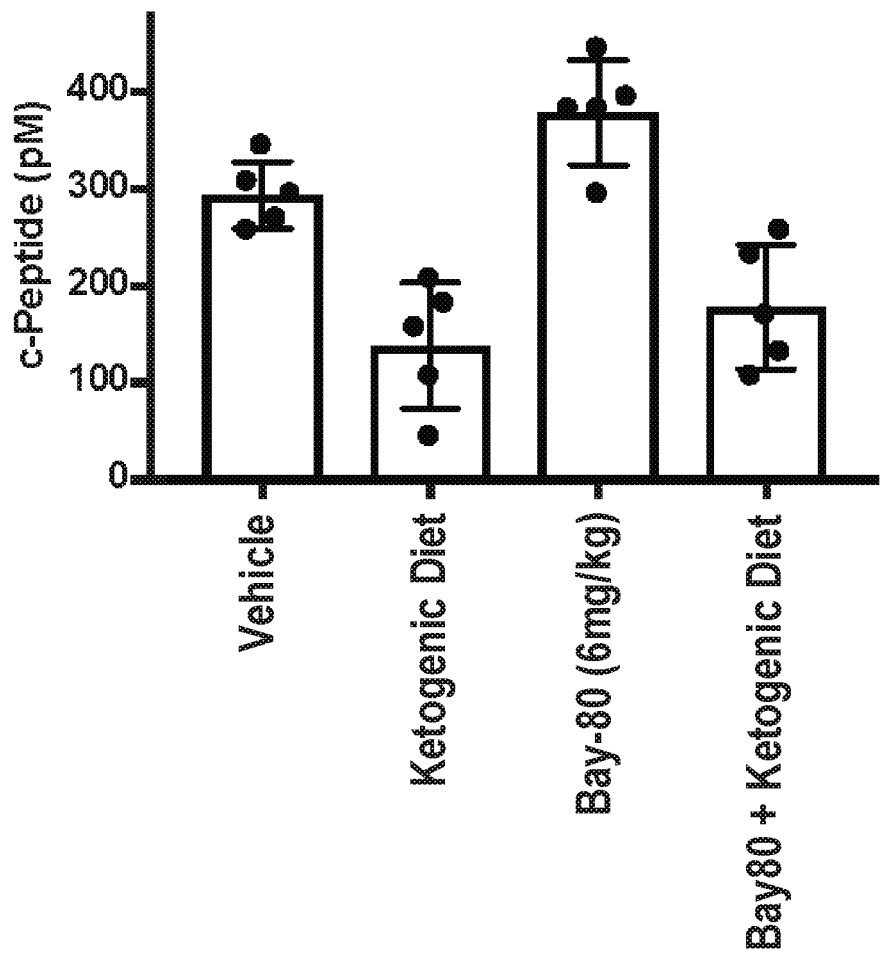
Figure 10E:
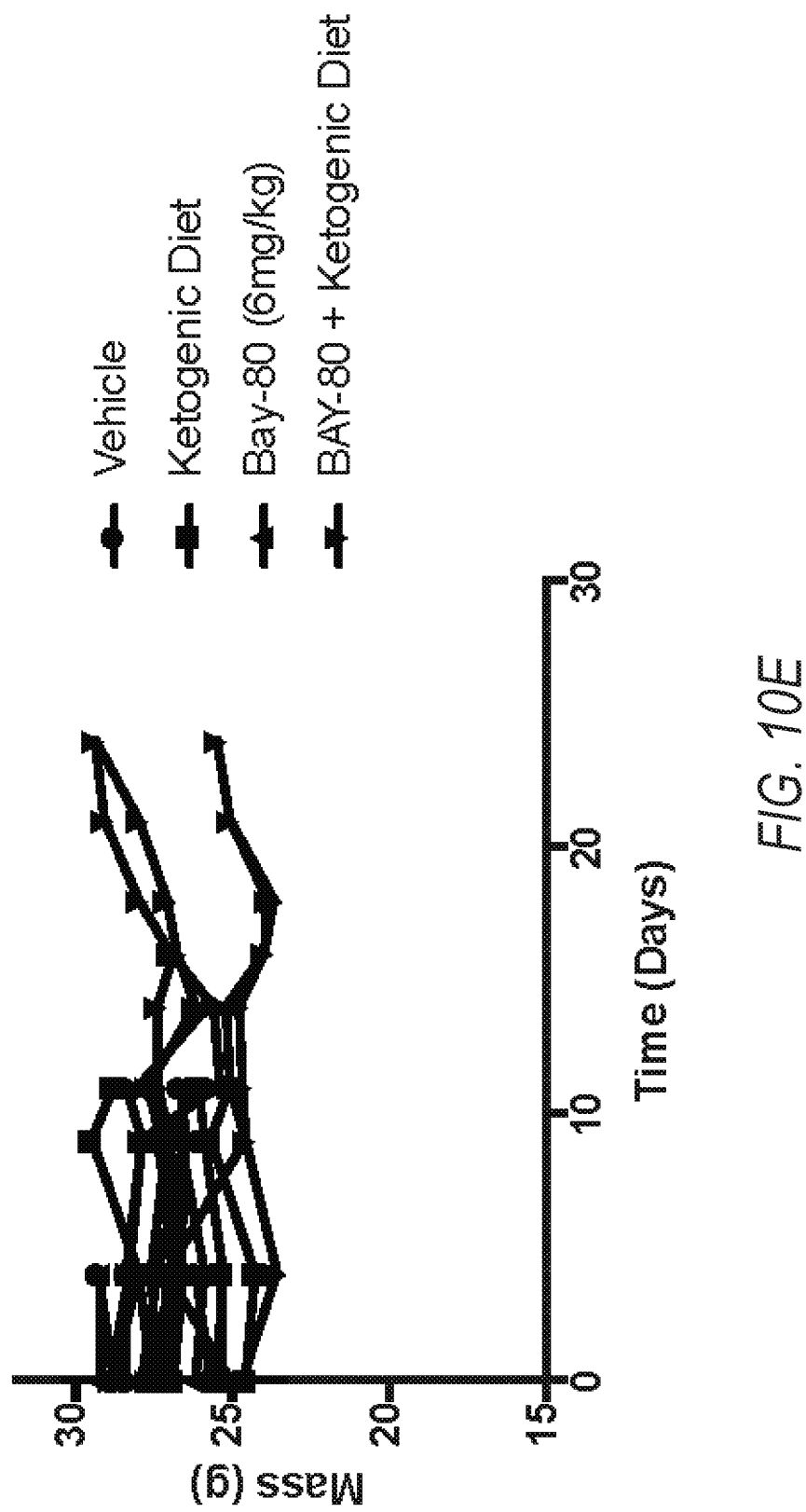
Figure 11A:
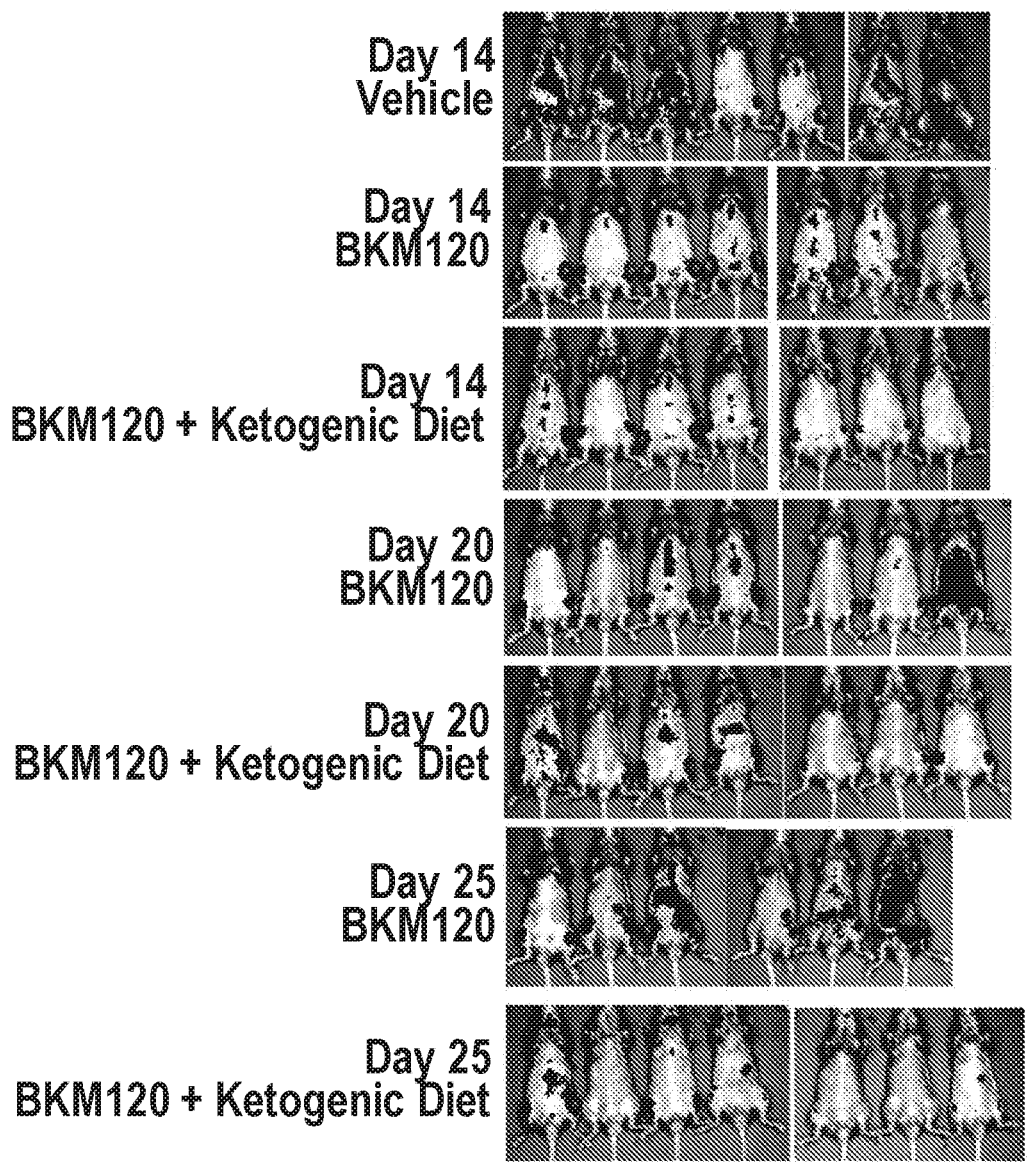
FIG. 11A-11F demonstrate the impact of BKM120/Ketogenic combination on a syngeneic model of AML.
Figure 11B:
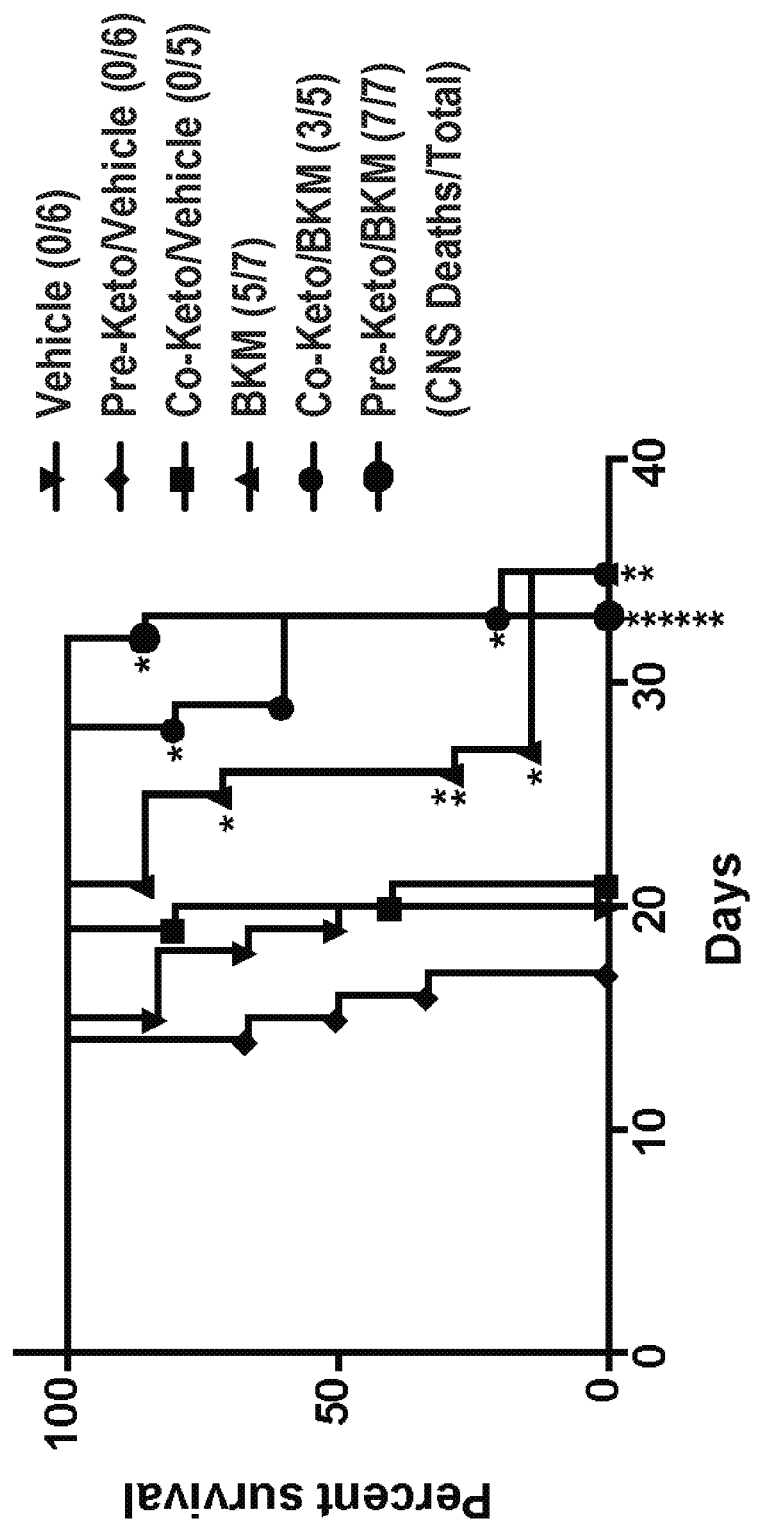
Figure 11C:
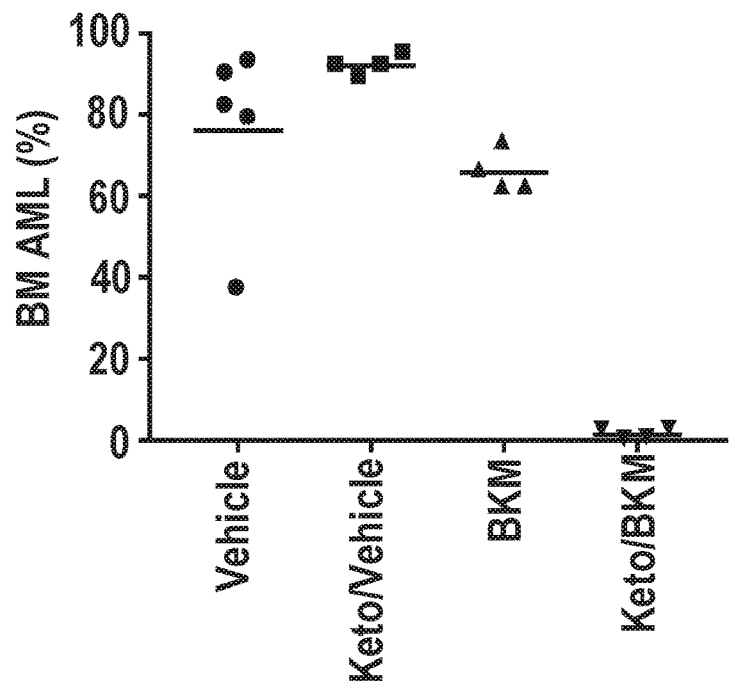
Figure 11D:
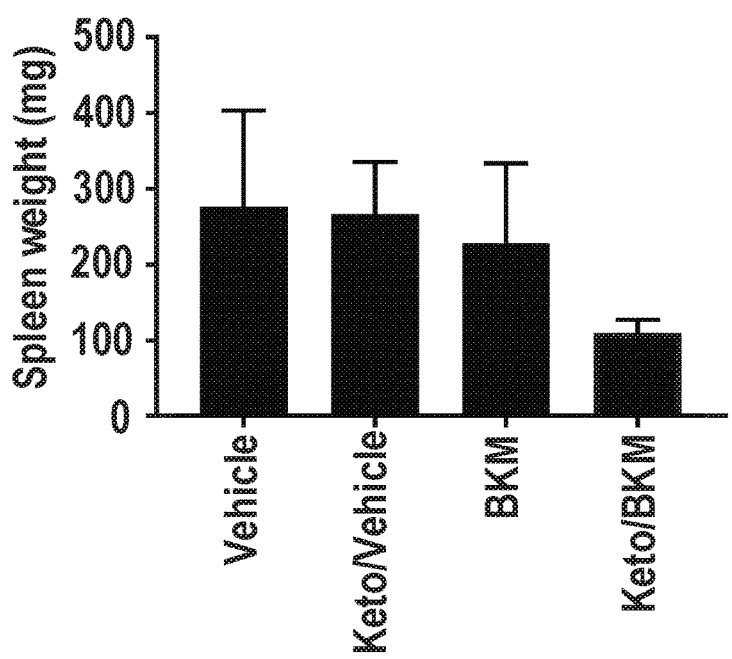
Figure 11E:
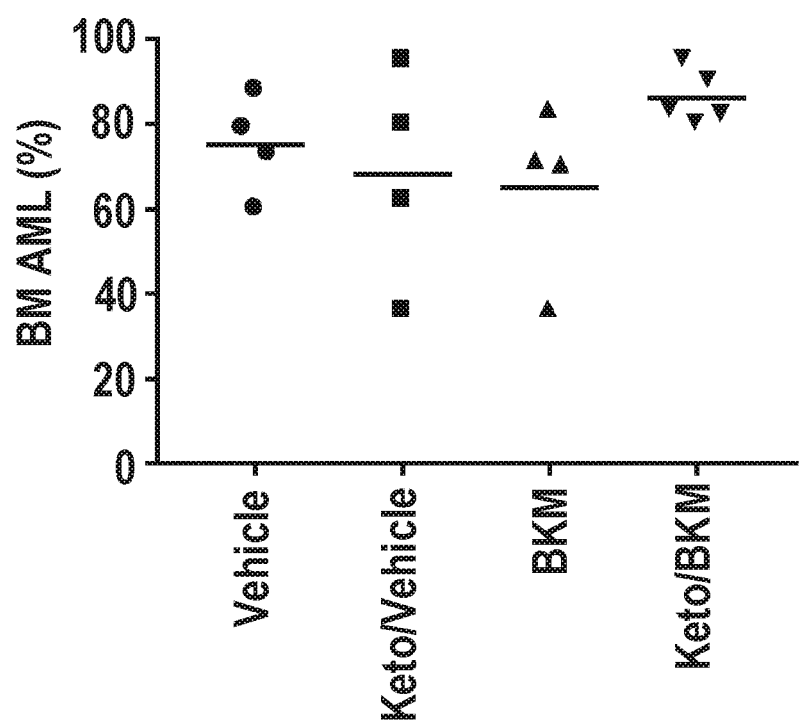
Figure 11F:
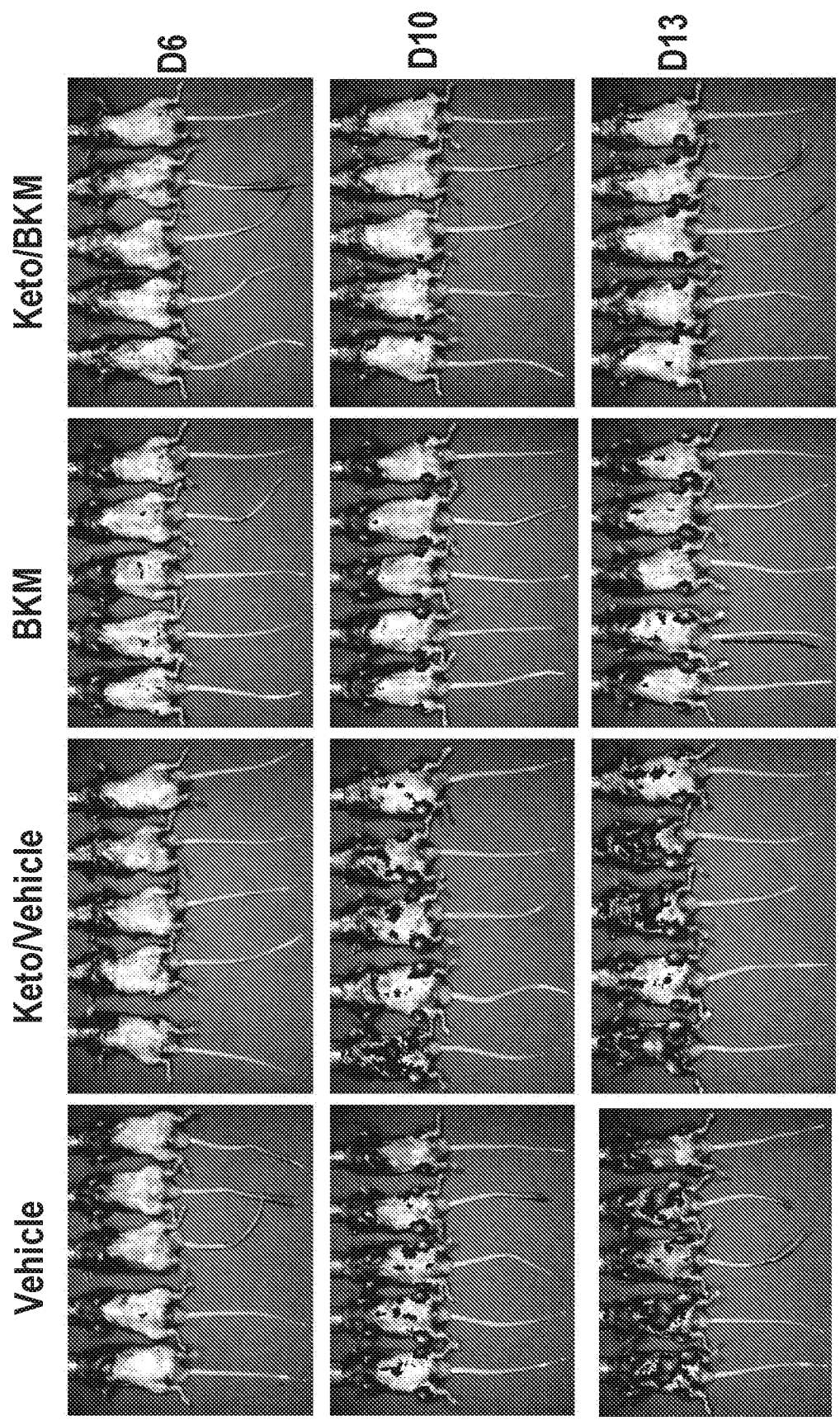

To further test whether the improved response to PI3K inhibitors while on a ketogenic diet is a consequence of lowering blood insulin levels, the inventors attempted to "rescue" the PI3K reactivation using exogenous insulin. A cohort of the mice bearing Pik3ca mutant breast allografts were treated with the combination of a ketogenic diet and BYL-719, and then given 0.4 mU of insulin 15 minutes after each dose of PI3K inhibitor (FIG. 4B). The addition of insulin dramatically reduced the therapeutic benefit of supplementing PI3K inhibitor therapy with a ketogenic diet, the addition of insulin also rescued tumor growth in allografted KPC tumors (FIG. 8H). It should be noted that the combination of the ketogenic diet, insulin, and BYL-719 was not well-tolerated in young mice so that ethical endpoints were reached due to weight loss in the KPC tumors after only one week of treatment.

Together these data demonstrate modulation of glucose metabolism improves responses to PI3K inhibitors by reducing blood insulin and the consequent ability of insulin to activate the insulin receptor in tumors. As demonstrated herein, modulation of glucose metabolism improves responses to PI3K inhibitors in tumors with a wide range of genetic aberrations. Therapeutic benefit was observed in patient-derived xenograft for advanced endometrial adenocarcinoma (harboring a PTEN deletion and PIK3CA mutation) and bladder cancer (FGFR Amplified) as well as syngeneic allograft for Pik3ca mutant breast cancer and MLL-AF9 driven Acute Myeloid Leukemia (FIG. 4C, FIGS. 9A-9E, FIGS. 10A-10E, FIGS. 11A-11E).

Modulation of glucose metabolism improved drug efficacy with an array of agents that target the PI3K pathway in addition to BKM120 and BYL719, including the pan PI3K inhibitor GDC-0941, the PI3K-β sparing compound GDC-0032, the mTOR/PI3K dual inhibitor GDC-0980, and the recently approved PI3K-α/δ inhibitor Copanlisib (FIG. 5). In some cases, the ketogenic diet alone had variable effects in different tumor models indicating that the dietary changes themselves were insufficient to cause the tumor responses observed across the murine models. In some instances, such as the AML model, the ketogenic diet alone accelerated disease progression suggesting that this diet may be detrimental for some cancer patients when used in isolation.

Figure 4D:
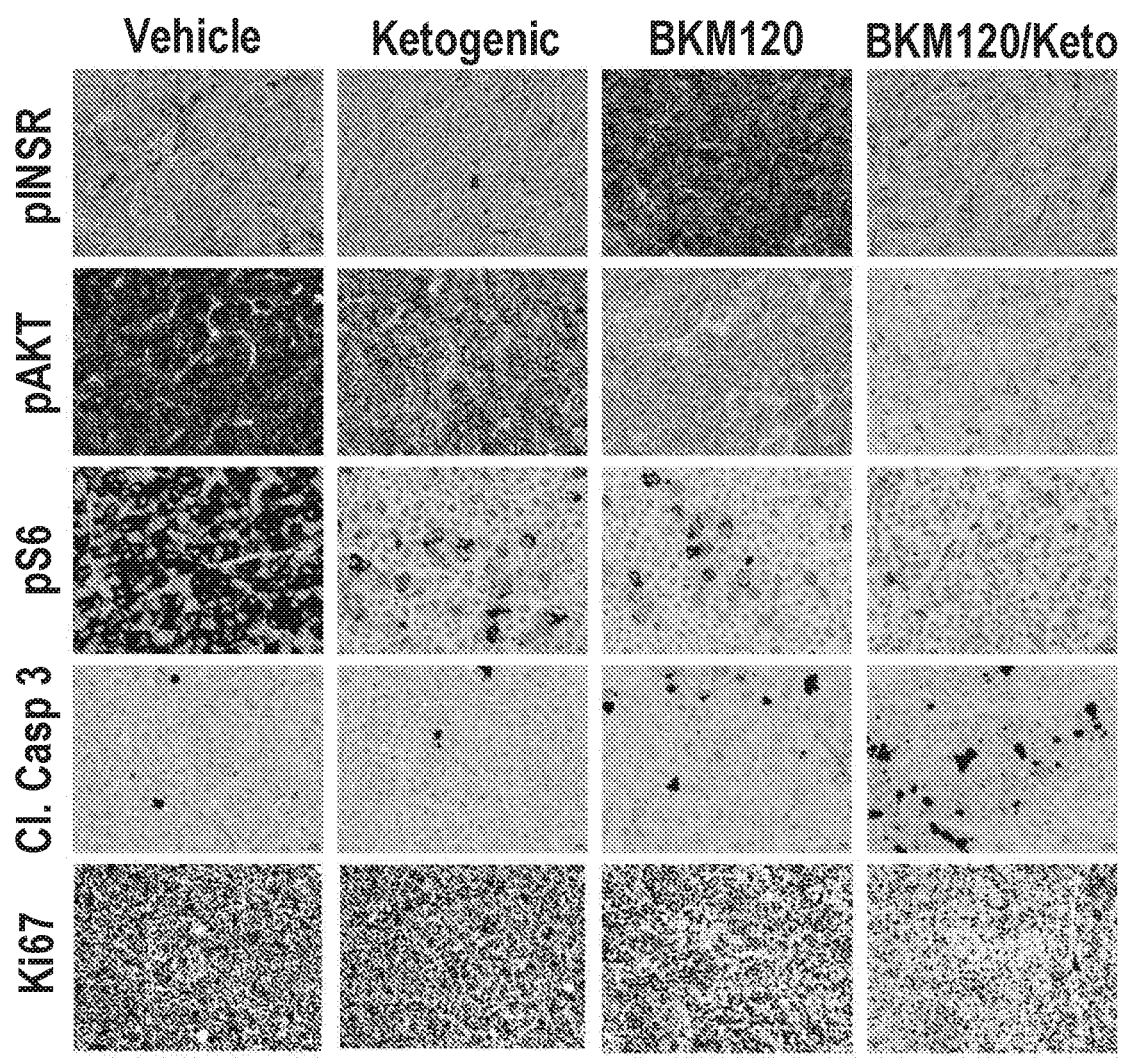
Figure 4E:
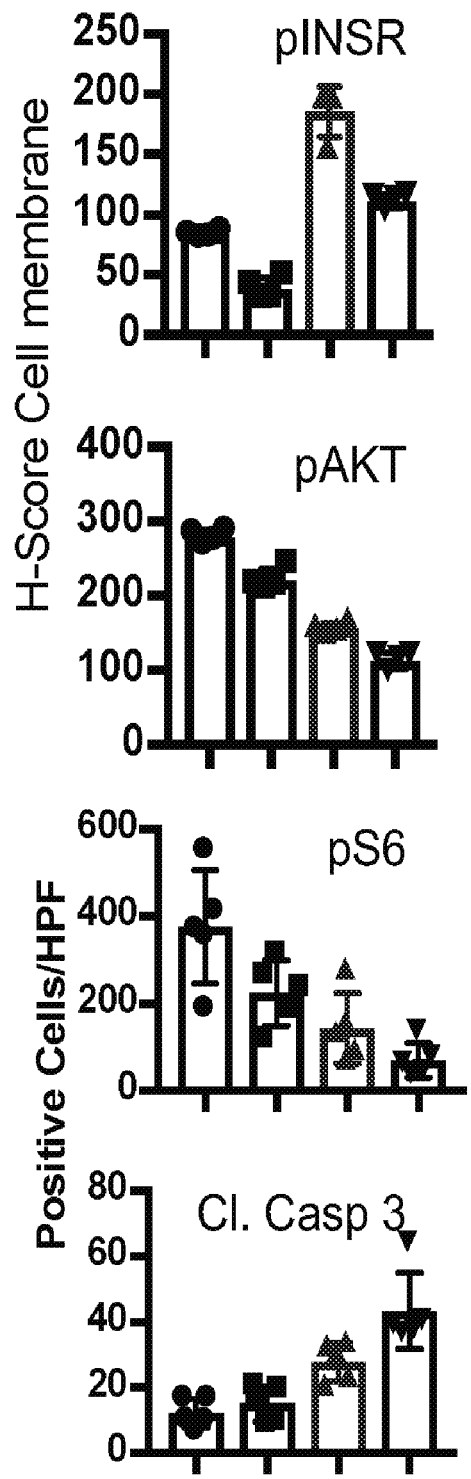

The data shown herein indicates that insulin feedback is limiting the efficacy of PI3K inhibition in various hematological malignancies and sold tumors. By reducing the systemic insulin response, the addition of the ketogenic diet to BKM120 reduced immunohistochemical markers of insulin signaling compared to tumors from mice treated with BKM120 alone in PTEN/PIK3CA mutant endometrial PDX tumors. In these exemplary tumors, the ketogenic diet enhanced the ability of BKM120 to reduce levels of phosphorylated insulin receptor, phosphorylated AKT and phosphorylated S6 and this reduction in signaling correlated with decreased levels of proliferation as shown by Ki67 staining, and increased levels of apoptosis as indicated by cleaved caspase 3 staining (FIG. 4D-E).

While these data do not exclude insulin-independent effects of combining PI3K inhibition with anti-glycemic therapy, they demonstrate this modulation of glucose metabolism significantly increases the therapeutic efficacy of these pathway inhibitors. In light of these results, it may also be important to think about how common clinical practices such as IV glucose administration, glucocorticoid use, or providing patients with glucose-laden nutritional supplements may impact therapeutic responses. Therapeutic agents that target this critical oncogenic pathway should be paired with strategies such as administration of modulators of glucose metabolism or ketogenic diet to limit this self-defeating systemic feedback.

Example 6: Multiple Approaches to Target Glucose/Insulin Feedback

This Example illustrates the in vivo impact of multiple approaches to concurrently target glucose/insulin feedback.

Figure 12A:
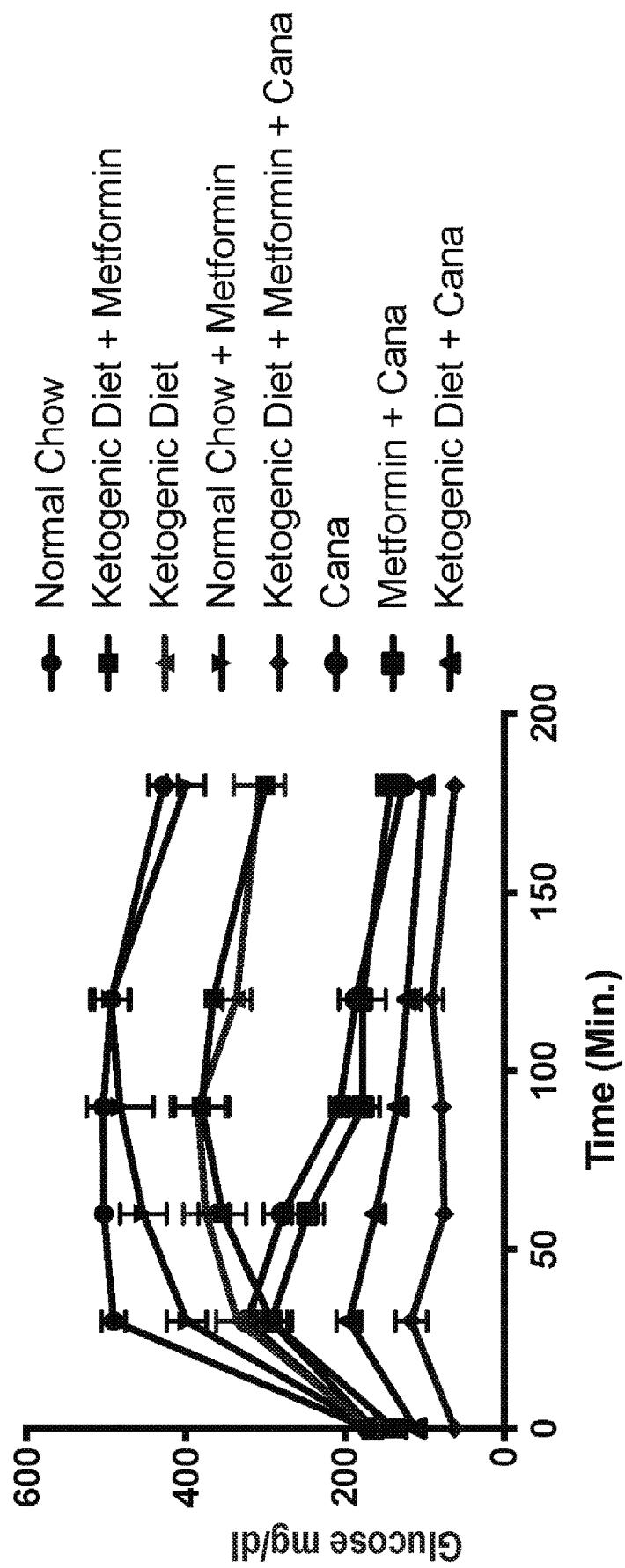
FIG. 12A-12C illustrate the in vivo impact of multiple approaches to targeting glucose/insulin feedback concurrently.
Figure 12B:
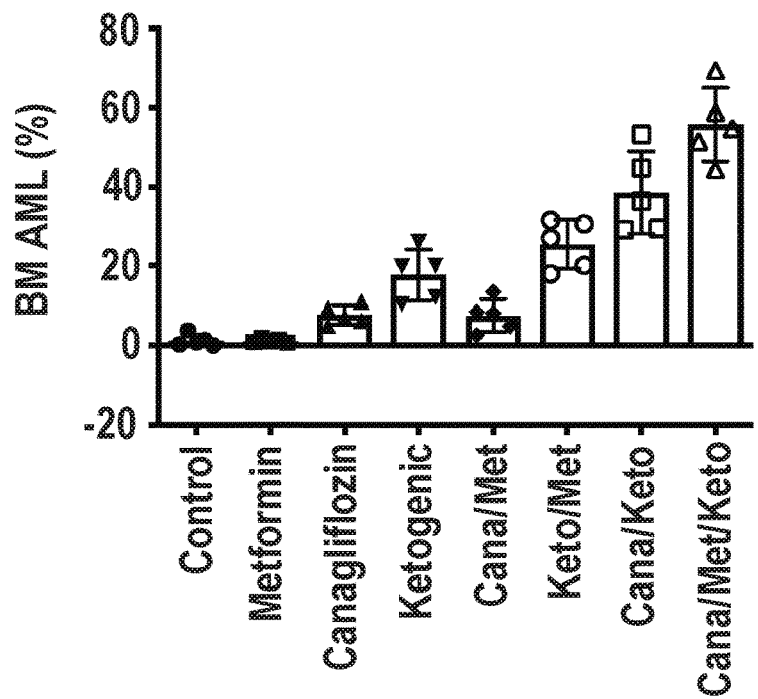
Figure 12C:
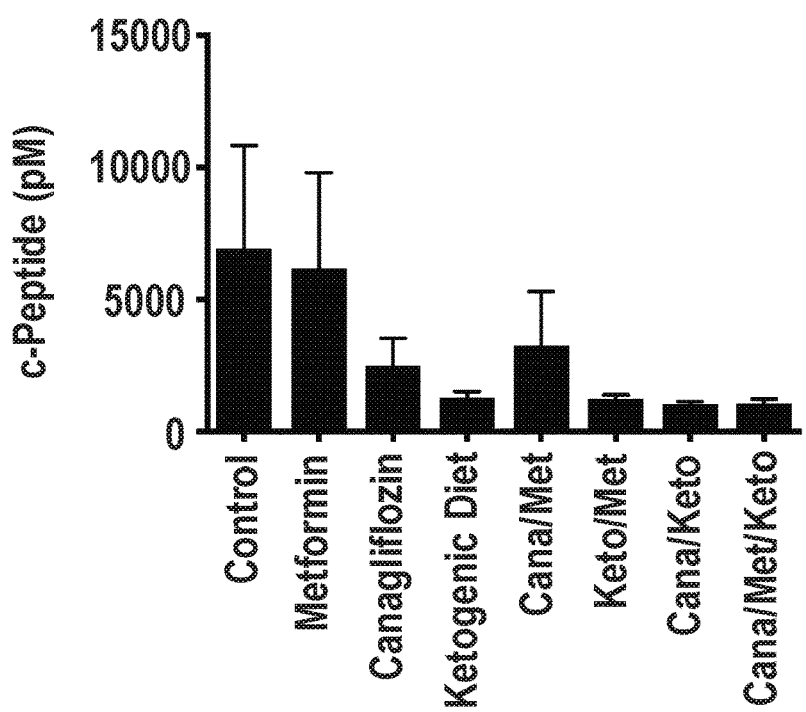

FIG. 12A-12C graphically illustrate blood glucose, ketone, and c-peptide levels in wildtype c57/b16 mice baring syngeneic K8484 KPC allografted tumors after treatment with a single dose of BKM120 with metformin pretreatment, SGLT2-inhibitor (SGLT2i) pretreatment, a ketogenic diet alone, or combinations of such treatments (N=4/arm). These data demonstrate that combining these approaches can have an added effect in controlling glucose/insulin feedback and can increase treatment efficacy by profoundly enhancing the response of the systemic metabolism to PI3K inhibition.

Example 7: Methods

Mice Procurement and Treatment

All animal studies were conducted following IACUC approved animal protocols (#2013-0116) at Weill Cornell Medicine and (AC-AAAQ5405) at Columbia University. Mice were maintained in temperature- and humidity-controlled specific pathogen-free conditions on a 12-hour light/dark cycle and received a normal chow diet (PicoLab Rodent 20 5053 lab Diet St. Louis, MO) or ketogenic diet (Thermo-Fisher AlN-76A) with free access to drinking water. Diets were composed as indicated in Table 3.

TABLE 3

Ketogenic Diet compared to a Normal Diet

|  | Normal Diet | Ketogenic Diet |
| --- | --- | --- |
| Protein | 21% | 8.6% |
| Fat | 11.3% | 75.1% |
| Fiber | 4.6% | 4.8% |
| Ash | 7% | 3.0% |
| Carbohydrate | 62% | 3.2% |

For solid tumor studies, Nude (genotype) and C57/BL6 mice were purchased at 8 weeks of age from Jackson laboratories (Bar Harbor, ME). They were injected with $0.5-1\times10^6$ cells in a 1:1 mix of growth media and matrigel (Trevigen, #3433-005-R1) and tumors were allowed to grow to a minimum diameter of 0.6 cm prior to the initiation of treatment. Tumors that did not meet this criteria at the time of treatment initiation were not utilized for experimentation.

For AML studies, 10-12 weeks old male C57BL/6J mice were used for MLL-AF9 Ds-Red AML study (Approved protocol AC-AAAQ5405). For pre-treatment study with MLL-AF9 Ds-Red cells, keto and Keto/BKM group mice were given a ketogenic diet for 10 days prior to injection with MLL-AF9 Ds-Red cells ($2\times10^5$ per mouse in 200 ul) via lateral tail vein. The day after iv injection, the mice were given 0.5% carboxymethyl cellulose (CMC) as vehicle control or BKM120 (37.5 mg/kg) by oral gavage for two weeks (5 out of 7 days). The mice were euthanized after two-week treatment to check the bone marrow for AML progress. The tumor progress was also monitored via IVIS spectrum machine.

For co-current treatment studies with MLL-AF9 Ds-Red cells, the mice were injected with MLL-AF9 Ds-Red cells ($2\times10^5$ per mouse in 200 ul) via lateral tail vein. The day after iv injection, the mice were given vehicle or BKM120 (37.5 mg/kg) by oral gavage for two weeks. The Keto or Keto/BKM group were changed to a ketogenic diet on the same day. The mice were euthanized after two-week treatment to check the bone marrow for AML progress.

To check if Keto/BKM treatment affects the AML engraftment, Keto and Keto/BKM group mice were given a ketogenic diet for 10 days, then treated with vehicle or BKM120 by oral gavage for two weeks. The mice were then injected with MLL-AF9 Ds-Red cells ($2\times10^5$ per mouse in 200 ul) vial lateral tail vein. Two weeks after the iv injection, the mice were euthanized to check the bone marrow for AML burden.

The survival study, pre-treatment study, and co-current treatment were conducted at the same time. The mice were treated with vehicle or BKM120 (5 out of 7 days) until spontaneous death, or mice were euthanized when they appeared to be very sick (reduced spontaneous activity, unkempt coat, and dehydrated appearance), achieved body weight loss over 20%, or demonstrated signs of limb paralysis. To check if Keto/BKM treatment affects the bone marrow cell population, C57BL/6J mice were treated with 8 doses of vehicle or BKM120 in 9 days. The mice were euthanized, and one femur and tibia were removed from each mouse. The bone marrow cells were flushed with PBS (2% FBS). The red blood cells were lysed with ACK lysis buffer (Invitrogen).

Antibodies used for flow cytometry were as follows: CD34 (RAM34) from eBioscience, c-Kit (2B8), Sca-1 (D7), CD3a (145-2C11), B220 (RA3-6B2), CD150 (TC-15-12F2.2), CD49b (DX5) and CD48 (HM48-1) from Biolegend. The 'lineage cocktail' included CD3, CD4, Gr-1, Mac-1 (CD11b), B220, and Terr-119. DAPI was used to exclude dead cells.

Compounds

GDC-0032, MK2206, BEZ235, BKM-120, GDC-0941, GDC-0980, and Canagliflozin were all procured from medchem express (Monmouth Junction, NJ) and given via oral gavage in 100 ul. Metformin was procured from Sigma Aldrich (St. Louis, MO). Bay-80 6946 and OSI-906 came from Sellechem catalogue #S2802 and #S1091 respectively. The targeting information for these compounds is displayed in Table 4. IC50 data was obtained from the Selleck Chem website (Selleckchem.com). The canagliflozin was administered 60 minutes before the PI3K pathway inhibitors so that its optimal efficacy lined up with the peak glucose levels. Mice treated with metformin were pretreated for 10 days prior to BKM120 treatment. Ketogenic diet was initiated at the time of initial PI3K inhibitor treatment unless otherwise stated. Doxycycline was procured from Sigma (St.

Louis, Missouri) catalogue number D3072-1ML and administered via intraperitoneal injection once daily at a dose of 3 mg/kg.

TABLE 4

Exemplary Pathway Inhibitors

| Compound Name | Compound ID | Targets of compound | IC50 of primary target |
|---|---|---|---|
| Buparlisib | BKM-120 | p110α/β/δ/γ | 52 nM |
| Dactolisib | BEZ-235 | p110α/γ/δ/β mTOR | 4 nM |
| Apelisib | BYL-719 | p110 α | 5 nM |
| MK2206 | MK2206 | AKT1/2/3 | 8 nM |
| Taselisib | GDC-0032 | PI3Kα/γ | 0.29 nM |
| Pictilisib | GDC-0941 | p110α/δ/β/γ | 3 nM |
| Apitolisib | GDC-0980 | PI3Kα/β/δ/γ mTOR | 5 nM |
| Copanilisib | BAY-80-6946 | PI3Kα/β/γ/δ | 0.5 nM |
| Linsitinib | OSI-906 | IGF1R/INSR | 35 nM |
| Conagliflozin | TA 7284 | SGLT-2 | 2.2 nM |

Cell Lines

Murine pancreas cell lines were kindly gifted by Dr. Kenneth Olive, Columbia University. Murine breast lines were kindly gifted by Dr. Ramon Parsons, Mount Sinai School of Medicine. PDX Models were derived by the Englander Institute of Precision Medicine. Cell lines HEK293, HCC-38, MDA-MB-468, PC-3, BT-549 were purchased from ATCC and grown in DMEM supplemented with 10% FBS and 1% Pen/Strep. HCT-116 and DLD-1 isogenic lines with and without PTEN deletion were kindly provided by the Laboratory of Todd Waldman. A chart of cells/organoids used is provided in Table 5, with known oncogenic alterations as described in publications cited above or as available from the ATCC (see website at atcc.org/~/media/PDFs/Culture %20Guides/Cell_Lines_by-_Gene_Mutation.ashx).

TABLE 5

Exemplary Cell Lines

| Cell/Organoid Line | Source | Tissue of Origin (Species) | Known Alterations in oncogenic Pathways |
|---|---|---|---|
| K8484 | Kenneth Olive (Columbia University) | Pancreas (Mouse) | KRAS (G12D) TP53 (H172R) |
| K8082 | Kenneth Olive (Columbia University) | Pancreas (Mouse) | KRAS (G12D) TP53 (H172R) |
| ES-278 | Ramon Parsons (Mount Sinai) | Mammary Gland (Mouse) | PIK3CA (H1047R) MYC |
| ES-272 | Ramon Parsons (Mount Sinai) | Mammary Gland (Mouse) | PIK3CA (H1047R) |
| MLL-AF9 | Mukherjee Lab Columbia University | AML | |
| Patient A | Englander Institute for Precision Medicine | Endometrial | PTEN Deletion PIK3CA (H1047R) |
| Patient B | Englander Institute for Precision Medicine | Endometrial | PTEN Deletion PIK3CA (H1047R) |
| Patient C | Englander Institute for Precision Medicine | Bladder | FGFR Amplification |
| MDA-MB-468 | ATCC | Breast (Human) | PTEN, RB1, SMAD4, TP53 |
| BT-549 | ATCC | Breast (Human) | PTEN, RB1, TP53 |
| PC-3 | ATCC | | PTEN, TP53 |
| HCC-38 | ATCC | Breast (Human) | TP53, CDKN2A, |
| DLD-1 Neo | Todd Waldman (Georgetown University) | Colon (Human) | APC, PIK3CA, RAS, TP53, |
| DLD-1 PTEN KO | Todd Waldman (Georgetown University) | Colon (Human) | APC, PIK3CA, RAS, TP53, PTEN* |
| HCT116 Neo | Todd Waldman (Georgetown University) | Colon (Human) | CDKN2A, CTNNB1, PIK3CA, RAS |
| HCT116 PTEN KO | Todd Waldman (Georgetown University) | Colon (Human) | CDKN2A, CTNNB1, PIK3CA, RAS, PTEN* |

Signaling Assays

For signaling assays, cells were washed 1× in PBS and placed in starvation media (−FBS) for 6-18 hours depending upon cell line and treated 1 hour prior to harvesting with PI3K inhibitors as indicated alone or in combination with insulin 10 minutes prior to harvesting. Three-dimensional culture and dose response experiments of patient derived organoids were run as previously described. In brief, ~1000 cells were plated in 10 ul of 1:1 matrigel to culture media in 96 well angiogenesis plates and allowed to solidify for 30 min at 37 degrees before 70 ul of culture media was added. Organoids were then treated in triplicate in a log scale dose response and CellTiter-Glo assay (Promega) was run at 96 hours to determine the $IC_{50}$ values. Proliferation assays in two-dimensional culture were performed as indicated in FIG. legends. Knockdown of insulin receptor was achieved using a doxycycline inducible shRNA strategy. For generation of miR-E shRNAs, 97-mer oligonucleotides were purchased (IDT Ultramers) coding for predicted shRNAs using an siRNA predictional tool Splash RNA (see website at splashrna.mskcc.org/).

Oligonucleotides were PCR amplified using the primers miRE-Xho-fw (5'-TGAACTCGAGAAGGTATAT-TGCTGTTGACAGTGAGCG-3', SEQ ID NO:1) and miRE-Eco-rev (5'-TGAACTCGAGAAGGTATAT-TGCTGTTGACAGT GAGCG-3', SEQ ID NO:2). PCR products were purified and both PCR product and LT3GEPIR vectors (Fellmann, C. et al. An optimized microRNA backbone for effective single-copy RNAi. Cell Rep 5, 1704-1713) were double digested with EcoRI-HF and XhoHI. PCR product and vector backbone were ligated and transformed in Stbl3 competent cells and grown at 320 overnight. Colonies were screened using the primer miRE-fwd (5'-TGTTTGAATGAGGCTTCAGTAC-3', SEQ ID NO:3).

```
Renilla (SEQ ID NO: 4):
TGCTGTTGACAGTGAGCGCAGGAATTATAATGCTTATCTATAGTGA
AGCCACAGATGTATAGATAAGCATTATAATTCCTATGCCTACTGCC
TCGGA INSR4 (SEQ ID NO: 5):
TGCTGTTGACAGTGAGCGCGGGGTTCATGCTGTTCTACAATAGTGA
AGCCACAGATGTATTGTAGAACAGCATGAACCCCATGCCTACTGCC
TCGGA
```

Immunoblotting

Cell lysates were prepared in 1×CST Cell Lysis Buffer #9803, (Danvers MA). Total protein concentration was evaluated with the BCA kit (Pierce) 23227). The lysates were run out on 4-20% Tris-Glycine Gels (ThermoFisher, Carlsbad CA). Primary antibodies against pAKT473, pAKT308, pS6, pTYR, AKT, and S6 were procured from Cell Signaling (Danvers, MA), and were used overnight 1:1000 in 5% bovine serum albumin. Actin and tubulin antibodies came from Sigma Aldrich and were used at 1:5,000 in 5% Milk. All these antibodies were visualized with HRP conjugated secondary antibodies from Jackson Immuno at 1:5000 in 5% milk.

Immunohistochemistry

Tumor sections (3 m) were antigen retrieved with 10 mmol/L citrate acid, 0.05% Tween 20, pH6.0, and incubated with antibodies as indicated (Ki67 (Abcam, ab16667) 1:500; cleaved caspase-3 (Asp175; SA1E; Cell Signaling Technology, 9664) 1:200; phospho-INSR (Tyr 1162; Thermo Fisher #AHR0271) 1:100; phospho-AKT (Ser473; Cell Signaling Technology, 8101) 1:20; and phospho-S6 ribosomal protein (Ser235/236; Cell Signaling Technology, 2211) 1:300).

Blood Measurements

For assessment of blood glucose 10 ul of blood was taken from the tail of mice prior to treatment (time 0) and then again at the indicated time points (15, 30, 60, 90, 120, 180 minutes) using a OneTouch Ultra Glucometer. At endpoint >100 ul of blood was drawn from the mice into EDTA tubes (Sarstedt #16.444). Blood was centrifuged (10,000×g for 10 min at 4° C.), and plasma was stored at −20° C. Plasma O-hydroxybutyrate, triglyceride (Stanbio Laboratory, Boerne, TX), Serum Insulin, and c-Peptide (APLCO Diagnostics, Salem, NH) levels were quantified by ELISA.

FDG-PET

Male c57/b16 mice (n=4/arm) bearing orthotopic pancreatic adenocarcinoma allografts were injected with 200-250 µCi [$^{89}$Zr]liposomes (3-4 µmol lipid) in 200-250 µL PBS solution into the tail vein. At the time of peak blood insulin feedback 90 minutes post BKM120 injection animals were anesthetized and scans were then performed using an Inveon PET/CT scanner (Siemens Healthcare Global). Whole body PET scans were performed recording a minimum of 50 million coincident events, with duration of 10 min. The energy and coincidence timing windows were 350-750 keV and 6 ns. The data was normalized to correct for non-uniformity of response of the PET, dead-time count losses, positron branching ratio, and physical decay to the time of injection. The counting rates in the reconstructed images were converted to activity concentrations (percentage injected dose [% ID] per gram of tissue) by use of a system calibration factor derived from the imaging of a phantom containing $^{89}$Zr. Images were analyzed using ASIPro VM™ software (Concorde Micro-systems). Quantification of activity concentration was done by averaging the maximum values in at least 5 ranges of interest (ROIs) drawn on adjacent slices of the pancreatic tumors.

Metabolomics

Metabolites were extracted from cells or tissues using 80% methanol. Each sample was transferred to a pre-cooled (dry ice) 2 mL homogenization tube containing a single stainless-steel bead (5 mm). Pre-cooled 80% methanol (1 mL) was added to each sample and homogenization was performed using the Qiagen TissueLyser II. Samples were then centrifuged at 4° C. for 15 minutes at 14,000 rpm. The supernatants were extracted and normalized based on tissue weight. Targeted LC/MS analyses were performed on a Q Exactive Orbitrap mass spectrometer (Thermo Scientific) coupled to a Vanquish UPLC system (Thermo Scientific). The Q Exactive operated in polarity-switching mode. A Sequant ZIC-HILIC column (2.1 mm i.d.×150 mm, Merck) was used for separation of metabolites. Flow rate was 150 L/min. Buffers consisted of 100% acetonitrile for A, and 0.1% $NH_4OH$/20 mM $CH_3COONH_4$ in water for B. Gradient ran from 85% to 30% A in 20 min followed by a wash with 30% A and re-equilibration at 85% A. Metabolites were identified on the basis of exact mass within 5 ppm and standard retention times. Relative metabolite quantitation was performed based on peak area for each metabolite. All data analysis was done using scripts written in-house.

REFERENCES

1 Kandoth, C. et al. Mutational landscape and significance across 12 major cancer types. *Nature* 502, 333-339, doi:10.1038/nature12634 (2013).

2 Millis, S. Z., Ikeda, S., Reddy, S., Gatalica, Z. & Kurzrock, R. Landscape of Phosphatidylinositol-3-Kinase Pathway Alterations Across 19784 Diverse Solid Tumors. *JAMA Oncol* 2, 1565-1573, doi:10.1001/jamaoncol.2016.0891 (2016).

3 Massacesi, C. et al. PI3K inhibitors as new cancer therapeutics: implications for clinical trial design. *Onco Targets Ther* 9, 203-210, doi:10.2147/OTT.S89967 (2016).

4 Mayer, I. A. et al. A Phase Ib Study of Alpelisib (BYL719), a PI3Kalpha-Specific Inhibitor, with Letrozole in ER+/HER2− Metastatic Breast Cancer. *Clin Cancer Res* 23, 26-34, doi:10.1158/1078-0432.CCR-16-0134 (2017).

5 Bendell, J. C. et al. Phase I, dose-escalation study of BKM120, an oral pan-Class I PI3K inhibitor, in patients with advanced solid tumors. *J Clin Oncol* 30, 282-290, doi:10.1200/JCO.2011.36.1360 (2012).

6 Juric, D. et al. Phase I Dose-Escalation Study of Taselisib, an Oral PI3K Inhibitor, in Patients with Advanced Solid Tumors. *Cancer Discov* 7, 704-715, doi:10.1158/2159-8290.CD-16-1080 (2017).

7 Patnaik, A. et al. First-in-human phase I study of copanlisib (BAY 80-6946), an intravenous pan-class I phosphatidylinositol 3-kinase inhibitor, in patients with advanced solid tumors and non-Hodgkin's lymphomas. *Ann Oncol* 27, 1928-1940, doi:10.1093/annonc/mdw282 (2016).

8 Gallagher, E. J. et al. Inhibiting PI3K reduces mammary tumor growth and induces hyperglycemia in a mouse model of insulin resistance and hyperinsulinemia. *Oncogene* 31, 3213-3222, doi:10.1038/onc.2011.495 (2012).

9 Hopkins, B. D., Goncalves, M. D. & Cantley, L. C. Obesity and Cancer Mechanisms: Cancer Metabolism. *J Clin Oncol* 34, 4277-4283, doi:10.1200/JCO.2016.67.9712 (2016).

10 Fruman, D. A. et al. The PI3K Pathway in Human Disease. *Cell* 170, 605-635, doi:10.1016/j.cell.2017.07.029 (2017).

11 Belardi, V., Gallagher, E. J., Novosyadlyy, R. & LeRoith, D. Insulin and IGFs in obesity-related breast cancer. *J*

12 Gallagher, E. J. & LeRoith, D. Minireview: IGF, Insulin, and Cancer. *Endocrinology* 152, 2546-2551, doi:10.1210/en.2011-0231 (2011).

13 Klil-Drori, A. J., Azoulay, L. & Pollak, M. N. Cancer, obesity, diabetes, and antidiabetic drugs: is the fog clearing? *Nat Rev Clin Oncol* 14, 85-99, doi:10.1038/nrclinonc.2016.120 (2017).

14 Ma, J. et al. A prospective study of plasma C-peptide and colorectal cancer risk in men. *J Natl Cancer Inst* 96, 546-553 (2004).

15 Xu, J. et al. Association between markers of glucose metabolism and risk of colorectal cancer. BMJ Open 6, e011430, doi:10.1136/bmjopen-2016-011430 (2016).

16 Ma, J. et al. Prediagnostic body-mass index, plasma C-peptide concentration, and prostate cancer-specific mortality in men with prostate cancer: a long-term survival analysis. *Lancet Oncol* 9, 1039-1047, doi:10.1016/S1470-2045(08)70235-3 (2008).

17 Olive, K. P. et al. Inhibition of Hedgehog signaling enhances delivery of chemotherapy in a mouse model of pancreatic cancer. *Science* 324, 1457-1461, doi:10.1126/science.1171362 (2009).

18 Pauli, C. et al. Personalized In Vitro and In Vivo Cancer Models to Guide Precision Medicine. *Cancer Discov* 7, 462-477, doi:10.1158/2159-8290.CD-16-1154 (2017).

19 Komoroski, B. et al. Dapagliflozin, a novel, selective SGLT2 inhibitor, improved glycemic control over 2 weeks in patients with type 2 diabetes mellitus. *Clin Pharmacol Ther* 85, 513-519, doi:10.1038/clpt.2008.250 (2009).

20 Demin, O., Jr., Yakovleva, T., Kolobkov, D. & Demin, O. Analysis of the efficacy of SGLT2 inhibitors using semi-mechanistic model. *Front Pharmacol* 5, 218, doi:10.3389/fphar.2014.00218 (2014).

21 Pollak, M. Metformin and other biguanides in oncology: advancing the research agenda. *Cancer prevention research* 3, 1060-1065, doi:10.1158/1940-6207.CAPR-10-0175 (2010).

22 Pollak, M. Potential applications for biguanides in oncology. *J Clin Invest* 123, 3693-3700, doi:10.1172/JCI67232 (2013).

23 Saura, C. et al. Phase Ib study of Buparlisib plus Trastuzumab in patients with HER2-positive advanced or metastatic breast cancer that has progressed on Trastuzumab-based therapy. *Clin Cancer Res* 20, 1935-1945, doi:10.1158/1078-0432.CCR-13-1070 (2014).

24 Juvekar, A. et al. Combining a PI3K inhibitor with a PARP inhibitor provides an effective therapy for BRCA1-related breast cancer. *Cancer Discov* 2, 1048-1063, doi:10.1158/2159-8290.CD-11-0336 (2012).

25 Puchalska, P. & Crawford, P. A. Multi-dimensional Roles of Ketone Bodies in Fuel Metabolism, Signaling, and Therapeutics. *Cell Metab* 25, 262-284, doi:10.1016/j.cmet.2016.12.022 (2017).

26 Sampaio, L. P. Ketogenic diet for epilepsy treatment. *Arq Neuropsiquiatr* 74, 842-848, doi:10.1590/0004-282X20160116 (2016).

27 Xia, J., Sinelnikov, I. V., Han, B. & Wishart, D. S. MetaboAnalyst 3.0—making metabolomics more meaningful. *Nucleic Acids Res* 43, W251-257, doi:10.1093/nar/gkv380 (2015).

28 Xia, J. & Wishart, D. S. Using MetaboAnalyst 3.0 for Comprehensive Metabolomics Data Analysis. *Curr Protoc Bioinformatics* 55, 14 10 11-14 10 91, doi:10.1002/cpbi.11 (2016).

29 Xia, J. & Wishart, D. S. MetPA: a web-based metabolomics tool for pathway analysis and visualization. *Bioinformatics* 26, 2342-2344, doi:10.1093/bioinformatics/btq418 (2010).

30 Xia, J. & Wishart, D. S. Metabolomic data processing, analysis, and interpretation using MetaboAnalyst. *Curr Protoc Bioinformatics* Chapter 14, Unit 14 10, doi:10.1002/0471250953.bi1410s34 (2011).

31 Douris, N. et al. Adaptive changes in amino acid metabolism permit normal longevity in mice consuming a low-carbohydrate ketogenic diet. *Biochim Biophys Acta* 1852, 2056-2065, doi:10.1016/j.bbadis.2015.07.009 (2015).

32 Pauli, C. et al. An emerging role for cytopathology in precision oncology. *Cancer Cytopathol* 124, 167-173, doi:10.1002/cncy.21647 (2016).

33 Lee, C., Kim, J. S. & Waldman, T. PTEN gene targeting reveals a radiation-induced size checkpoint in human cancer cells. *Cancer Res* 64, 6906-6914, doi:10.1158/0008-5472.CAN-04-1767 (2004).

34 Pelossof, R. et al. Prediction of potent shRNAs with a sequential classification algorithm. *Nat Biotechnol* 35, 350-353, doi:10.1038/nbt.3807 (2017).

35 Fellmann, C. et al. An optimized microRNA backbone for effective single-copy RNAi. *Cell Rep* 5, 1704-1713, doi:10.1016/j.celrep.2013.11.020 (2013).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:

1. A method of treating a disease or disorder associated with PI3K signaling, comprising administering to a subject in need thereof an effective amount of a modulator of glucose metabolism; and administering to the subject an effective amount of a pathway inhibitor of the insulin-receptor/PI3K/AKT/mTOR pathway.
2. The method of statement 1, wherein the modulator of glucose metabolism is a glucose-uptake inhibitor, optionally selected from the group consisting of a sodium-glucose-linked transport protein 1 (SGLT1) inhibitor, a sodium-glucose-linked transport protein 2 (SGLT2) inhibitor, or a dual SGLT1/SGLT2 inhibitor.
3. The method of statement 2, wherein the glucose-uptake inhibitor is selected from the group consisting of dapagliflozin, empagliflozin, canagliflozin, ipragliflozin, tofogliflozin, sergliflozin etabonate, remogliflozin etabonate, ertugliflozin, sotagliflozin, and conagliflozin.
4. The method of statement 1, wherein the modulator of glucose metabolism is metformin.
5. The method of statement 1, wherein the modulator of glucose metabolism is an insulin receptor/IGF1 receptor inhibitor, wherein optionally the insulin receptor/IGF1 receptor inhibitor is linsitinib (OSI-906).
6. The method of any of statements 1-5, wherein the pathway inhibitor is capable of inhibiting one or more kinases selected from the group consisting of INSR/IGFR, PI3K, AKT, and mTOR.

7. The method of statement 6, wherein the pathway inhibitor is selected from the group consisting of idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, apelisib, MK2206, and linsitinib (OSI-906).

8. The method of any of statements 1-7, wherein the disease or disorder is associated with PI3K signaling is a cancer or cell-proliferative disorder, a metabolic disorder, a neurodegenerative disease, or an inflammatory disease.

9. The method of any of statements 1-8, wherein the disease or disorder associated with PI3K signaling is a neurodegenerative disease, optionally brain trauma, spinal cord trauma, trauma to the peripheral nervous system, Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffman disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, and prion diseases (including Creutzfeldt-Jakob, Gerstmann-Straussler-Scheinker disease, Kuru and fatal familial insomnia, age-related dementia, vascular dementia, diffuse white matter disease (Binswanger's disease), dementia of endocrine or metabolic origin, dementia of head trauma and diffuse brain damage, dementia pugilistica or frontal lobe dementia, neurodegenerative disorders resulting from cerebral ischemia or infraction including embolic occlusion and thrombotic occlusion as well as intracranial hemorrhage of any type, intracranial and intravertebral lesions, hereditary cerebral angiopathy, hereditary amyloid, Down's syndrome, macroglobulinemia, secondary familial Mediterranean fever, Muckle-Wells syndrome, multiple myeloma, pancreatic-related amyloidosis, cardiac-related amyloidosis, chronic hemodialysis arthropathy, Finnish amyloidosis, Iowa amyloidosis, or a combination thereof.

10. The method of any of statements 1-8, wherein the disease or disorder associated with PI3K signaling is an inflammatory disorder, optionally Type II diabetes, insulin resistance cardiovascular disease, arrhythmia, atherosclerosis, coronary artery disease, hypertriglyceridemia, dyslipidemia, retinopathy, nephropathy, neuropathy, obesity, and macular edema, ileitis, ulcerative colitis, Barrett's syndrome, or Crohn's disease.

11. The method of any of statements 1-8, wherein the disease or disorder associated with PI3K signaling is a metabolic disease, optionally Type II diabetes, insulin resistance cardiovascular disease, arrhythmia, atherosclerosis, coronary artery disease, hypertriglyceridemia, dyslipidemia, retinopathy, nephropathy, neuropathy, obesity, or macular edema.

12. The method of any of statements 1-10 or 11, wherein the subject consumes or is administered a ketogenic diet during treatment.

13. A method of treating a disease or disorder associated with PI3K signaling, comprising administering an effective amount of at least one pathway inhibitor of at least one kinase in the insulin-receptor/PI3K/AKT/mTOR pathway, wherein the subject consumes or is administered a ketogenic diet during treatment.

14. The method of any of the preceding statements, which disrupts systemic glucose homeostasis and improves efficacy of pathway-inhibitor treatment compared to pathway inhibitor alone.

15. Use of a modulator of glucose metabolism and/or an inhibitor of the insulin-receptor/PI3K/AKT/mTOR pathway for treating a disease or disorder associated with PI3K signaling in a subject.

16. The use of statement 15 combined with use of a ketogenic diet by the subject.

17. A pharmaceutical composition comprising a modulator of glucose metabolism and a pathway inhibitor that inhibits at least one kinase in the insulin-receptor/PI3K/AKT/mTOR pathway.

18. The pharmaceutical composition of statement 17, wherein the modulator of glucose metabolism is a glucose-uptake inhibitor, a sodium-glucose-linked transport protein 1 (SGLT1) inhibitor, a sodium-glucose-linked transport protein 2 (SGLT2) inhibitor, or a dual SGLT1/SGLT2 inhibitor.

19. The pharmaceutical composition of statement 17 or 18, wherein the glucose-uptake inhibitor is selected from the group consisting of dapagliflozin, empagliflozin, canagliflozin, ipragliflozin, tofogliflozin, sergliflozin etabonate, remogliflozin etabonate, ertugliflozin, sotagliflozin, and conagliflozin.

20. The pharmaceutical composition of statement 17, 18, or 19, wherein the modulator of glucose metabolism is metformin.

21. The pharmaceutical composition of statement 17-19 or 20, wherein the modulator of glucose metabolism is an insulin receptor/IGF1 receptor inhibitor, wherein optionally the insulin receptor/IGF1 receptor inhibitor is linsitinib (OSI-906).

22. The pharmaceutical composition of any of statement 17-20 or 21, wherein the pathway inhibitor is capable of inhibiting one or more kinases selected from the group consisting of INSR/IGFR, PI3K, AKT, and mTOR.

23. The pharmaceutical composition of statement 17-21 or 22, wherein the pathway inhibitor is selected from the group consisting of idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, apelisib, MK2206, and linsitinib (OSI-906).

24. A method of inhibiting cell proliferation or a cell-proliferative disease, comprising administering to a subject in need thereof an effective amount of a glucose-uptake inhibitor; and administering to the subject an effective amount of a PI3K inhibitor.

25. The method of statement 24, wherein the glucose-uptake inhibitor is selected from the group consisting of dapagliflozin, empagliflozin, canagliflozin, ipragliflozin, tofogliflozin, sergliflozin etabonate, remogliflozin etabonate, ertugliflozin, sotagliflozin, and conagliflozin.

26. The method of statement 24 or 25, wherein the PI3K inhibitor is selected from the group consisting of idelalisib, copanlisib, buparlisib (BKM120), alpelisib (BYL719), taselisib (GDC-0032), pictilisib (GDC-0941), apitolisib (GDC-0980), serabelisib (TAK-117), dactolisib, MK2206, linsitinib (OSI-906), and apelisib.

27. The method of any of statements 24-25 or 26, wherein the inhibition of cell proliferation or cell-proliferative disease is enhanced compared to administration of the PI3K inhibitor without a glucose-uptake inhibitor.

The specific compositions and methods described herein are representative, exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a drug" or "an inhibitor" includes a plurality of such compounds, or drugs, or inhibitors, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed is:

1. A method of improving the efficacy of a PI3K inhibitor in a treatment of a patient with a cancer that is pancreatic, breast, endometrial, bladder, leukemia, lung, or liver cancer the method comprising administering to the patient a PI3K inhibitor selected from copanlisib, buparlisib, alpelisib, taselisib, pictilisib or serabelisib in combination with a ketogenic diet that reduces serum insulin levels thereby improving the efficacy of the PI3K inhibitor wherein the ketogenic diet comprises at least 80% of fat and protein by weight.

2. The method of claim 1, wherein the PI3K inhibitor is alpelisib, taselisib, or serabelisib.

3. The method of claim 1, further comprising administering at least one modulator of glucose metabolism.

4. The method of claim 3, wherein the at least one modulator of glucose metabolism is a sodium-glucose-linked transport protein 1 (SGLT1) inhibitor, a sodium-glucose-linked transport protein 2 (SGLT2) inhibitor, or a dual SGLT1/SGLT2 inhibitor.

5. The method of claim 3, wherein the at least one modulator of glucose metabolism is dapagliflozin, empagliflozin, canagliflozin, ipragliflozin, tofogliflozin, sergliflozin etabonate, remogliflozin etabonate, ertugliflozin, or sotagliflozin.

6. The method of claim 3, wherein the at least one modulator of glucose metabolism is a sodium-glucose-linked transport protein 2 (SGLT2) inhibitor.

7. The method of claim 3, wherein the at least one modulator of glucose metabolism is metformin.

8. The method of claim 1, wherein the patient is on the ketogenic diet before and during the administering of the copanlisib, buparlisib, alpelisib, taselisib, pictilisib or serabelisib.

9. The method of claim 1, wherein the patient is on the ketogenic diet before the administering of the copanlisib, buparlisib, alpelisib, taselisib, pictilisib or serabelisib.

10. The method of claim 1, wherein the patient is on the ketogenic diet during the administering of the copanlisib, buparlisib, alpelisib, taselisib, pictilisib or serabelisib.

11. The method of claim 1, wherein the ketogenic diet comprises a 2.5:1 to a 3:1 ratio of grams of fat to grams of carbohydrate and protein combined.

12. The method of claim 1, wherein the ketogenic diet comprises at most 10% of carbohydrate.

13. The method of claim 1, wherein the ketogenic diet comprises about 90% of calories from fat and about 10% of calories from carbohydrate and protein combined.

14. The method of claim 1, wherein the cancer is lung cancer.

15. The method of claim 1, wherein the cancer is liver cancer.

16. The method of claim 1, wherein the cancer is pancreatic cancer.

17. The method of claim 1, wherein the cancer is endometrial cancer.

18. The method of claim 1, wherein the cancer is bladder cancer.

19. The method of claim 1, wherein the cancer is leukemia.

20. The method of claim 1, wherein the cancer is breast cancer.

21. The method of claim 1, wherein the cancer comprises one or more of a PIK3CA mutation and a PIK3R1 mutation.

22. The method of claim 1, wherein the cancer comprises a PTEN alteration.

23. The method of claim 1, wherein the cancer comprises a PTEN deletion.

24. The method of claim 1, wherein the PI3K inhibitor inhibits one or more of p110-α, p110-β, p110-γ, p110-δ, p85-α, p85-β, p55-γ, p150, p101, p87, PI3K-C2α, PI3K-C2β, PI3K-C2γ, and Vps34.

25. The method of claim 1, wherein the PI3K inhibitor is serabelisib.

26. The method of claim 25, further comprising administering at least one modulator of glucose metabolism.

27. The method of claim 25, wherein the cancer is endometrial cancer.

28. The method of claim 25, wherein the cancer is breast cancer.

29. The method of claim 25, wherein the method further comprises administering an mTOR inhibitor.

30. The method of claim 1, wherein the method further comprises administering an mTOR inhibitor.

31. The method of claim 1, wherein improving the efficacy of the PI3K inhibitor comprises reducing a level of PI3K signaling.

32. The method of claim 1, wherein improving the efficacy of the PI3K inhibitor comprises one or more of reducing a level of phosphorylated AKT (pAKT) and reducing a level of phosphorylated S6 (pS6).

33. The method of claim 1, wherein the method comprises measuring the serum insulin by ELISA or by a level of c-peptide.

34. The method of claim 1, wherein the ketogenic diet reduces a marker of insulin signaling compared to treatment with the PI3K inhibitor without administration of the ketogenic diet.

35. The method of claim 34, wherein the marker of insulin signaling is phosphorylated insulin receptor (pINSR).

36. The method of claim 1, wherein the ketogenic diet reduces cell proliferation compared to treatment with the PI3K inhibitor without administration of the ketogenic diet.

37. The method of claim 36, wherein the ketogenic diet reduces Ki67 levels or increases levels of apoptosis.

38. The method of claim 1, wherein an effective amount of the PI3K inhibitor when in combination with the ketogenic diet is lower than an effective amount of the PI3K inhibitor without the ketogenic diet.

39. The method of claim 38, wherein the effective amount of the PI3K inhibitor in combination with the ketogenic diet is less than about 90% of the effective amount of the PI3K inhibitor without the ketogenic diet.

40. The method of claim 1, wherein the ketogenic diet comprises about 2% to about 5% of carbohydrates.

* * * * *